US012577231B2

(12) United States Patent
Tinworth et al.

(10) Patent No.: US 12,577,231 B2
(45) Date of Patent: Mar. 17, 2026

(54) ANDROGEN RECEPTOR PROTACS

(71) Applicant: GlaxoSmithKline Intellectual Property Development Limited, Stevenage (GB)

(72) Inventors: Christopher Patrick Tinworth, Stevenage (GB); Laura Trulli, Madrid (ES)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 19/254,759

(22) Filed: Jun. 30, 2025

(65) Prior Publication Data

US 2026/0001865 A1 Jan. 1, 2026

Related U.S. Application Data

(63) Continuation of application No. PCT/EP2024/076364, filed on Sep. 20, 2024.

(30) Foreign Application Priority Data

Sep. 22, 2023 (EP) .................................... 23382956

(51) Int. Cl.
*C07D 401/14* (2006.01)
*A61P 35/00* (2006.01)
*C07D 405/14* (2006.01)
*C07D 471/04* (2006.01)
*C07D 487/04* (2006.01)

(52) U.S. Cl.
CPC ............ *C07D 401/14* (2013.01); *A61P 35/00* (2018.01); *C07D 405/14* (2013.01); *C07D 471/04* (2013.01); *C07D 487/04* (2013.01)

(58) Field of Classification Search
CPC .. C07D 401/14; C07D 405/14; C07D 471/04; C07D 487/04; A61P 35/00
See application file for complete search history.

(56) References Cited

U.S. PATENT DOCUMENTS

2025/0205344 A1* 6/2025 Bamborough ....... C07D 471/10

FOREIGN PATENT DOCUMENTS

| | | | |
|---|---|---|---|
| WO | WO-2018144649 | A1 | 8/2018 |
| WO | WO-2022069520 | A1 | 4/2022 |
| WO | WO-2022087125 | A1 | 4/2022 |
| WO | WO-2022262782 | A1 | 12/2022 |
| WO | WO-2023180388 | A1 | 9/2023 |

OTHER PUBLICATIONS

Co-Pending U.S. Appl. No. 18/849,815, filed Mar. 9, 2024, 506 Pages.

Huber P. R., et al., "Prostate Specific Antigen. Experimental and Clinical Observations," Scandinavian Journal of Urology and Nephrology Supplementum, 1987, vol. 104, pp. 33-39(1 Page Abstract Only).

International Search Report and Written Opinion for International Application No. PCT/EP2024/076364, mailed Dec. 4, 2024, 12 Pages.

Noble R.L., "The Development of Prostatic Adenocarcinoma in Nb Rats Following Prolonged Sex Hormone Administration," Cancer Research, Jun. 1977, vol. 37, pp. 1929-1933.

Roberts T., et al., "Adenocarcinoma of Prostate in Year-old Body-builder," Sep. 27, 1986, vol. 328(8509), pp. 742.

Wilson J., et al., "Long-Term Consequences of Castration in Men: Lessons from the Skoptzy and the Eunuchs of the Chinese and Ottoman Courts," The Journal of Clinical Endocrinology & Metabolism, 1999, vol. 18(12), pp. 4324-4331.

* cited by examiner

*Primary Examiner* — Timothy R Rozof
(74) *Attorney, Agent, or Firm* — Eric Myers; Nicole Ginanni

(57) ABSTRACT

Certain Androgen receptor PROTAC (PROteolysis TArgeting Chimera) compounds contain a series of 2,4-dioxotetrahydropyrimidinyl derivatives that bind cereblon. The PROTAC compounds may be viewed as being comprised of an androgen receptor binding moieties, a linker and a cereblon binding moiety or degron. Medical uses of these PROTAC compounds are also disclosed.

28 Claims, 2 Drawing Sheets

ANDROGEN RECEPTOR PROTACS

CROSS REFERENCE TO RELATED APPLICATIONS

The present application is a continuation of International Application No. PCT/EP2024/076364, filed Sep. 20, 2024, the contents of which are herein incorporated by reference in their entirety, and claims priority to European Patent Application No. 23382956.3, filed Sep. 22, 2023, the contents of which are herein incorporated by reference in their entirety.

FIELD OF THE INVENTION

The present invention provides Androgen receptor PROTACs containing a series of 2,4-dioxotetrahydropyrimidinyl derivatives that bind cereblon. Medical uses of these PROTACS are also disclosed.

BACKGROUND TO THE INVENTION

The Ubiquitin Proteosome Pathway System (UPS) is a pathway for degrading regulatory proteins as well as misfolded or abnormal proteins. It achieves this by post translational modification of substrate proteins by the covalent attachment of ubiquitin. The covalent attachment of ubiquitin to specific protein substrates is achieved through the action of E3 ubiquitin ligases. Over 500 E3 ubiquitin ligases are known. One such E3 ubiquitin ligase is Cereblon. Cereblon (CRBN) forms a complex with damaged DNA binding protein 1 (DDB1), Cullin-4A (CUL4A), and regulator of cullins 1 (ROC1). This complex recognises naturally occurring protein substrates and catalyses the addition of ubiquitin, targeting the substrates for destruction.

The PROTAC (PROteolysis TArgeting Chimera) approach hijacks the UPS to degrade proteins that would not normally be substrates. PROTAC compounds are compounds that are typically comprised of three parts, a portion dedicated to binding to the target protein (target binding moiety), a portion binding to an E3 ligase capable of recruiting the complex capable of ubiquitinating the target protein (degron), and a linker connecting the two portions. Upon binding to a target, the PROTAC generates a ternary complex of all of the components needed to ubiquitinate the target, leading to ubiquitination and subsequently degradation of the target.

Cereblon is a molecular target of immunomodulatory agents such as thalidomide, lenalidomide, and pomalidomide. These agents have been widely used as E3 ligase binding moieties in PROTAC compounds. WO2022069520 discloses compounds that are said to be cereblon binding moieties.

Androgens mostly exert their biological effects via binding to the Androgen Receptor (AR). In the absence of androgens, AR is bound to Heat Shock Protein 90 (Hsp90) in the cytosol in such a way as to mask the Nuclear Localisation Signal (NLS). When an androgen binds AR, this induces a conformational change leading to the release of Hsp90, exposing the NLS. The AR then translocates into the nucleus where it acts as a transcription factor (Endocrin Rev. 1987, 8(1): 1-28; Mol Endocrinol. 2002, 16(10), 2181-7).

Androgens have long been known to be associated with prostate carcinogenesis. The evidence for this comes from several sources. First, androgens induce prostate cancer in rodent animal models (Noble, Cancer Res., 37, 1929-1933 (1977)). Second, men receiving androgens in the form of anabolic steroids have a higher incidence of prostate cancer (Roberts and Essenhigh, Lancet, 2, 742 (1986)) and prostate cancer does not develop following castration (Wilson and Roehrborn, J Clin Endrocrin Metab, 84, 4324-4331, 1999). Finally, and most convincingly, the only effective treatment available for advanced prostate cancer is withdrawal of androgens and is referred to as androgen ablation therapy (ABT) or androgen depravation therapy (ADT) or chemical castration. However, most patients develop resistance to these treatments and the disease progresses (Huber et al., 1987, Scan J Urol 104, 33-39).

Castration resistant prostate cancer cells have undergone changes to enable them to survive under castration levels of androgen. These mechanisms include AR overexpression, changes to androgen biosynthesis, the expression of constitutively active AR splice variants, changes to androgen cofactors and the expression of mutated versions of the AR. For example, gain of function mutations in the ligand binding domain of the AR such as L702H, W742C, W742L, H875Y and T878A can change ligand binding affinity, which results in increased sensitivity to steroid ligands or the conversion of anti-androgens to agonists. The T878A mutation is associated with resistance to abiraterone acetate and hydroxyflutamide. The L702H mutation is associated with receptor promiscuity, that is increased AR sensitivity to glucocorticoids.

AR is therefore a critical driver of tumorigenesis in prostate cancer, including castration resistant prostate cancer and its elimination should lead to therapeutically beneficial response.

In addition to their role in prostate cancer, androgens also play a role in other diseases. One example is ovarian cancer where elevated levels of androgens are associated with an increased risk of developing ovarian cancer (Helzlsouer et al., JAMA 274, 1926-1930 (1995), Edmondson et al., Br J Cancer 86, 879-885 (2002)). Indeed, AR is detected in the majority of ovarian cancers (Risch, J. Natl. Cancer Inst., 90, 1774-1786, 1998, Rao and Slotman, Endocr Rev., 12, 14-26, 1991, Clinton and Hua, Crit Rev Oncol., Hematol., 25, 1-9, 1997)).

SUMMARY OF THE INVENTION

In a first aspect, the invention provides a compound of formula (I), a tautomer of a compound of formula (I), or a salt thereof:

(I)

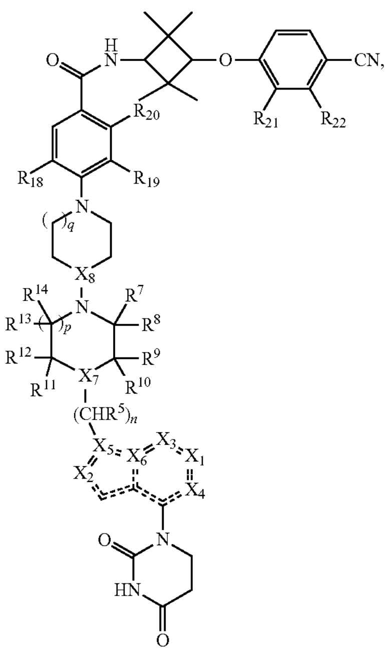

wherein:

$X_1$ is N or C—$R^1$, wherein $R^1$ is selected from the group consisting of H, halo, $C_{1-4}$alkyl, $C_{1-4}$haloalkyl, $C_{1-4}$alkoxy and —$CONR^3R^4$;

$R^3$, $R^4$ and $R^5$ are independently selected from H or $C_{1-4}$alkyl;

$X_4$ is C—$R^2$ or N, wherein $R^2$ is selected from the group consisting of H, halo, $C_{1-3}$alkyl, $C_{1-3}$haloalkyl and $C_{1-3}$alkoxy;

$X_2$ and $X_3$ are independently selected from N or CH;

$X_6$ and $X_5$ are independently selected from N or C, wherein when $X_6$ is N, $X_5$ is C;

n, p, q and r are independently 0 or 1;

$X_7$ is $CR^6$;

$R^6$, $R^7$, $R^8$, $R^9$, $R^{10}$, $R^{11}$, $R^{12}$, $R^{13}$ and $R^{14}$ are independently selected from H or halo;

$X_8$ is $CR^{15}R^{16}$;

and wherein either a) $R^{15}$ and $R^{16}$ together with the carbon atom to which they are attached join together to form a cyclobutyl ring; or b) $R^{15}$ is —$(CHR^{17})$—, $R^{16}$ is H, OH or a halo, and $R^{17}$ is H or halo;

$R^{18}$, $R^{19}$ and $R^{20}$ are independently H, halo or $C_{1-3}$haloalkyl;

and wherein either i) $R^{22}$ is selected from the group consisting of halo and —$OR^{23}$; and $R^{21}$ is independently H or methyl, wherein $R^2$ is $C_{1-3}$alkyl; or ii) $R^{21}$ and $R^{22}$ together with the phenyl to which they are attached join together to form a bicyclic ring selected from the group consisting of:

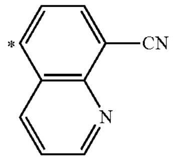

and

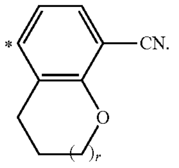

wherein the asterisks indicate the point of attachment to the oxygen atom.

For the avoidance of doubt, the double dotted lines in the 5,6-bicyclic ring structure describe an aromatic structure.

Compounds of formula (I) are "PROTACs". The "components" of a PROTAC will be described further herein. Pharmaceutical compositions and medical uses of Androgen Receptor PROTACs are also provided.

DESCRIPTION OF DRAWINGS/FIGURES

DETAILED DESCRIPTION OF THE INVENTION

Definitions

Figure 1:
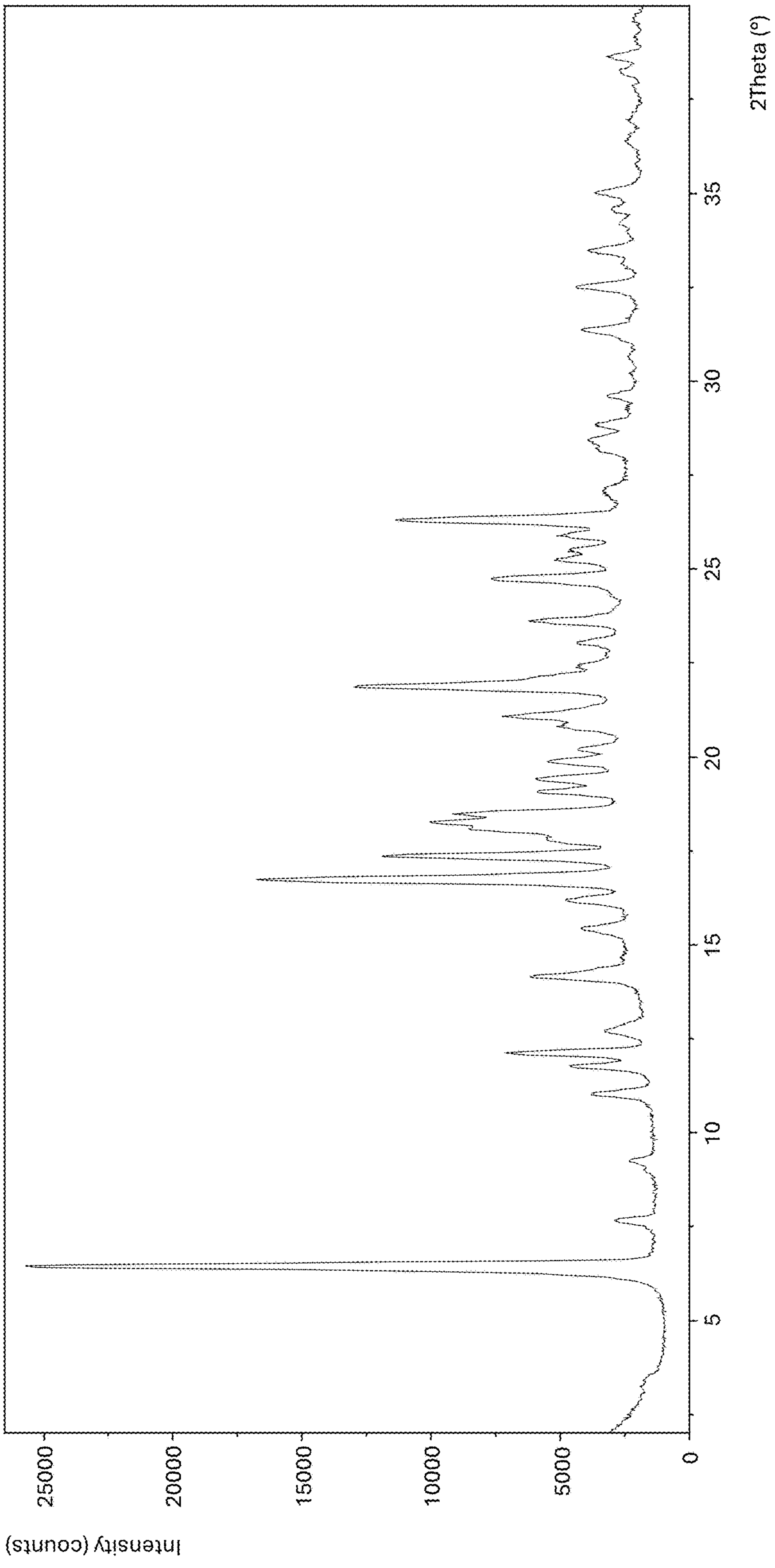
FIG. 1 is an X ray crystal diffractogram of a crystalline form of N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide free base.

The term "alkyl" refers to a monovalent, saturated hydrocarbon radical, straight or branched, having the specified number of carbon atoms. For example, the term "$C_{1-4}$ alkyl" refers to an alkyl group having 1 to 4 carbon atoms. Exemplary groups include, but are not limited to, methyl, ethyl, propyl (n-propyl and isopropyl) and butyl (n-butyl, sec-butyl, isobutyl and tert-butyl).

The term "alkoxy" refers to an —O-alkyl group, i.e. an alkyl group which is attached through an oxygen linking atom, wherein "alkyl" is defined above. For example, the term "$C_{1-4}$ alkoxy" refers to an alkoxy group having 1 to 4 carbon atoms. Exemplary groups include, but are not limited to, methoxy, ethoxy, n-propoxy, isopropoxy, n-butoxy, s-butoxy, isobutoxy, and t-butoxy.

The terms "halogen" and "halo" represent chloro, fluoro, bromo, or iodo substituents.

The term "haloalkyl" "is intended to mean a radical having one or more halogen atoms, which may be the same or different, at one or more carbon atoms of an alkyl group, where"alkyl" is defined above. Exemplary groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

STATEMENT OF THE INVENTION

In a first aspect, the invention provides a compound of formula (I), a tautomer of a compound of formula (I), or a salt thereof:

(I)

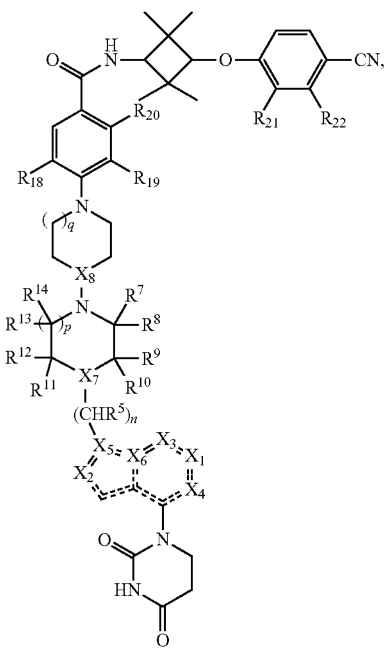

wherein:

$X_1$ is N or C—$R^1$ wherein $R^1$ is selected from the group consisting of H, halo, $C_{1-4}$alkyl, $C_{1-4}$haloalkyl, $C_{1-4}$alkoxy and —$CONR^3R^4$;

$R^3$, $R^4$ and $R^5$ are independently selected from H or $C_{1-4}$alkyl;

$X_4$ is C—$R^2$ or N wherein $R^2$ is selected from the group consisting of H, halo, $C_{1-3}$alkyl, $C_{1-3}$haloalkyl and $C_{1-3}$alkoxy;

$X_2$ and $X_3$ are independently selected from N or CH;

$X_6$ and $X_5$ are independently selected from N or C, wherein when $X_6$ is N, $X_5$ is C;

n, p, q and r are independently 0 or 1;

$X_7$ is $CR^6$;

$R^6$, $R^7$, $R^8$, $R^9$, $R^{10}$, $R^{11}$, $R^{12}$, $R^{13}$ and $R^{14}$ are independently selected from H or halo;

$X_8$ is $CR^{15}R^{16}$;

and wherein either a) $R^{15}$ and $R^{16}$ together with the carbon atom to which they are attached join together to form a cyclobutyl ring; or b) $R^{15}$ is —$(CHR^{17})$—, $R^{16}$ is H, OH or a halo, and $R^{17}$ is H or halo;

$R^{18}$, $R^{19}$ and $R^{20}$ are independently H, halo or $C_{1-3}$haloalkyl;

and wherein either i) $R^{22}$ is selected from the group consisting of halo and —$OR^{23}$ and $R^{21}$ is independently H or methyl, wherein $R^2$ is $C_{1-3}$alkyl; or ii) $R^{21}$ and $R^{22}$ together with the phenyl to which they are attached join together to form a bicyclic ring selected from the group consisting of:

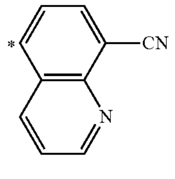

and

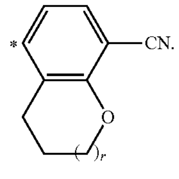

wherein the asterisks indicate the point of attachment to the oxygen atom.

The PROTAC compounds of the invention may be viewed as being comprised of an androgen receptor binding moieties, a linker and a cereblon binding moiety or degron. However, it must be appreciated that these are not discrete moieties and impact upon one another due to the conformation adopted by the compound as a whole. For example, it is possible that a portion of the compound that is designated as a linker, may in fact bind to either the androgen receptor or to cereblon, depending upon the conformation of the compound as a whole. Conversely, it is possible that a part of the cereblon binding moiety may not in fact be involved in binding cereblon due to the conformation of the compound as a whole. The skilled person will appreciate that the designation of a part of the molecule as a linker, cereblon binder or androgen receptor binding moiety is simply for convenience and is not intended to limit the function of these portions of the compounds.

Degron

The compound of formula (I) comprises a degron capable of binding the E3 ligase, cereblon. The degron has the structure set out below as formula (II).

Also disclosed is a degron of formula (II), a tautomer of a compound of formula (II), or a salt thereof:

(II)

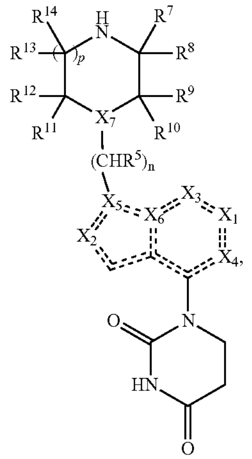

wherein:

$X_1$ is N or C—$R^1$, wherein $R^1$ is selected from the group consisting of H, halo, $C_{1-4}$alkyl, $C_{1-4}$haloalkyl, $C_{1-4}$alkoxy and —$CONR^3R^4$;

$R^3$, $R^4$ and $R^5$ are independently selected from H or $C_{1-4}$alkyl;

$X_4$ is C—$R^2$ or N, wherein $R^2$ is selected from the group consisting of H, halo, $C_{1-3}$alkyl, $C_{1-3}$haloalkyl and $C_{1-3}$alkoxy;

$X_2$ and $X_3$ are independently selected from N or CH;

$X_6$ and $X_5$ are independently selected from N or C, wherein when $X_6$ is N, $X_5$ is C;

n and p are independently 0 or 1;

$X_7$ is $CR^6$; and $R^6$, $R^7$, $R^8$, $R^9$, $R^{10}$, $R^{11}$, $R^{12}$, $R^{13}$ and $R^{14}$ are independently selected from H or halo.

In one embodiment of the degron of formula (II), the compound of formula (I), or a tautomer or salt thereof, $X_5$ is N and $X_6$ is C. In certain embodiments in which $X_5$ is N and $X_6$ is C, $X_2$ is additionally N.

In one embodiment of the degron of formula (II), the compound of formula (I), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_6$ is C and $X_1$ is C—$R^1$.

In a more particular embodiment of the degron of formula (II), the compound of formula (I), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$.

In one embodiment of the degron of formula (II), the compound of formula (I), or a tautomer or salt thereof, $R^1$ is selected from H, halo, and $C_{1-4}$haloalkyl. In a more particular embodiment, $R^1$ is H, halogen or —$CF_3$. In a more particular embodiment, $R^1$ is H, fluoro, chloro, or —$CF_3$. In a further embodiment, $R^1$ is H.

In one embodiment of the degron of formula (II), the compound of formula (I), or a tautomer or salt thereof, $R^2$ is H, fluoro, chloro or $CF_3$. In one embodiment, $R^2$ is H or fluoro.

In a more particular embodiment of the degron of formula (II), the compound of formula (I), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a more particular embodiment of the degron of formula (II), the compound of formula (I), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is CH; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is CH; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In one embodiment of the degron of formula (II), the compound of formula (I), or a tautomer or salt thereof $X_5$, $X_2$ and $X_4$ are each N, $X_3$ is CH, $X_6$ is C and $X_1$ is CH.

In a more particular embodiment of the degron of formula (II), the compound of formula (I), or a tautomer or salt thereof $X_5$ is N, $X_2$ and $X_3$ are each CH, $X_6$ is C, $X_1$ is C—$R^1$ wherein $R^1$ is H or fluoro, and $X_4$ is CH.

In a more particular embodiment of the degron of formula (II), the compound of formula (I), or a tautomer or salt thereof $X_5$ and $X_2$ are each N, $X_3$ is CH, $X_6$ is C, $X_1$ is C—$R^1$ wherein $R^1$ is H or fluoro and $X_4$ is CH.

In one embodiment of the degron of formula (II), the compound of formula (I), or a tautomer or salt thereof, n is 0.

In one embodiment of the degron of formula (II), the compound of formula (I), or a tautomer or salt thereof wherein n is 1, $R^5$ is H or methyl. In a more particular embodiment, $R^5$ is H.

In one embodiment of the degron of formula (II), the compound of formula (I), or a tautomer or salt thereof, $R^6$ is H.

In one embodiment of the degron of formula (II), the compound of formula (I), or a tautomer or salt thereof, p is 1. In another embodiment, p is 0.

In one embodiment of the degron of formula (II), the compound of formula (I), or a tautomer or salt thereof, $R^7$, $R^8$, $R^9$, $R^{10}$, $R^{11}$, $R^{12}$, $R^{13}$ and $R^{14}$ are independently selected from H or fluoro. In another embodiment, $R^{10}$ is H or halo and $R^7$, $R^8$, $R^9$, $R^{11}$, $R^{12}$, $R^1$ and $R^{14}$ are each H. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is fluoro and $R^7$, $R^8$, $R^9$, $R^{11}$, $R^{12}$, $R^{13}$ and $R^{14}$ are each H. In an alternative embodiment, $R^7$, $R^8$, $R^9$, $R^{10}$, $R^{11}$, $R^{12}$, $R^{13}$ and $R^{14}$ are each H.

Androgen Receptor Binding Moiety

Compounds binding the androgen receptor are well known in the art. In one embodiment, the androgen receptor binding moiety has the structure of formula (III)

(III)

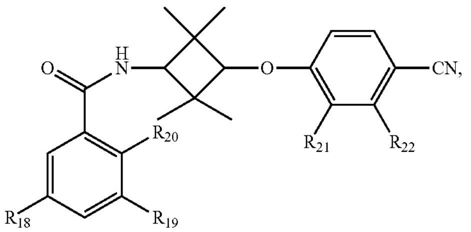

wherein:

$R^{11}$, $R^{19}$ and $R^{20}$ are independently H, halo or $C_{1-3}$haloalkyl; and either a) $R^{22}$ is selected from the group consisting of halo and —$OR^{23}$ and $R^{21}$ is independently H or methyl, wherein $R^{23}$ is $C_{1-3}$alkyl; or b) $R^{21}$ and $R^{22}$ together with the phenyl to which they are attached join together to form a bicyclic ring selected from the group consisting of:

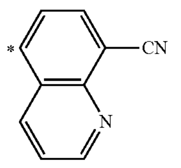
and
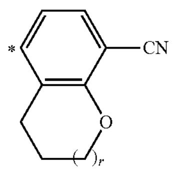

wherein the asterisks indicate the point of attachment to the oxygen atom; and r is 0 or 1.

The androgen receptor binding moiety of formula (III) can bind to certain mutated versions of the androgen receptor. Protacs containing the androgen receptor binding moiety of formula (III) exhibit activity in the dual mutant (T878A/L702H) Androgen Receptor Degradation Assay and in the Androgen Receptor Degradation-Imaging Assay which demonstrates the ability to degrade Androgen Receptor mutations seen in the human prostate cancer cell lines (MDA-PCa-2b (AR T878A/L702H), LNCaP (AR T878A), VCaP (AR wild type and amplified) and 22RV1 (AR H875Y). In addition, the examples demonstrate the ability of the compound N-((1r,3r)-3-((8-cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide (Example 20) to degrade overexpressed mutant forms L702H, H875Y W742C W742L F877L, T878A and T878A/H875Y) of the Androgen Receptor in A549 cell lines. In view of the above, PROTACs containing the androgen receptor binding moiety of formula (III) and in particular the compound of example 20 are expected to be useful for the treatment of prostate cancer, including castration-resistant prostate cancer.

In one embodiment of the androgen receptor binder of formula (III), the compound of formula (I), or a tautomer or salt thereof, $R^{18}$, $R^{19}$ and $R^{20}$ are each independently H or halo. In a more particular embodiment, $R^{18}$, $R^{19}$ and $R^{20}$ are each independently H or fluoro. In one embodiment, $R^{18}$ is halo, and $R^{19}$ and $R^{20}$ are each independently H or halo. In one embodiment, $R^{18}$ is fluoro or chloro, and $R^{19}$ and $R^{20}$ are each independently H or fluoro. In one embodiment, $R^{18}$ is fluoro, and $R^{19}$ and $R^{20}$ are each independently H.

In one embodiment of the androgen receptor binder of formula (III), the compound of formula (I), or a tautomer or salt thereof:

$R^{18}$ is fluoro, and $R^{19}$ and $R^{20}$ are each H; or
$R^{18}$ is chloro, and $R^{19}$ and $R^{20}$ are each H; or
$R^{18}$ and $R^{20}$ are each fluoro, and $R^{19}$ is H; or
$R^{18}$ and $R^{19}$ are each fluoro, and $R^{20}$ is H.

In one embodiment, the androgen receptor binding moiety has the structure of formula (IIIa):

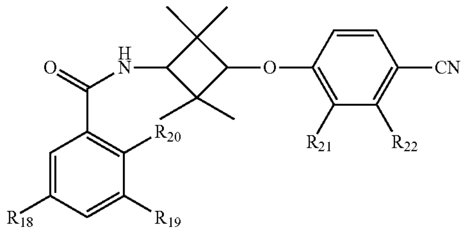

wherein:

$R^{18}$, $R^{19}$ and $R^{20}$ are independently H, halo or $C_{1-3}$haloalkyl; and $R^{21}$ is selected from the group consisting of halo and —$OR^{23}$;

$R^{22}$ is independently H or methyl; and $R^{23}$ is $C_{1-3}$alkyl.

In one embodiment of the androgen receptor binder of formula (IIIa), the compound of formula (I), or a tautomer or salt thereof, $R^{21}$ is H.

In one embodiment of the androgen receptor binder of formula (IIIa), the compound of formula (I), or a tautomer or salt thereof, $R^{22}$ is selected from the group consisting of chloro, methoxy and ethoxy. In one embodiment, $R^{22}$ is chloro. In an alternative embodiment, $R^{22}$ is methoxy.

In one embodiment of the androgen receptor binder of formula (IIIa), the compound of formula (I), or a tautomer or salt thereof:

$R^{18}$ is fluoro, and $R^{19}$ and $R^{20}$ are each H; or
$R^{18}$ is choro, and $R^{19}$ and $R^{20}$ are each H; or
$R^{18}$ and $R^{20}$ are each fluoro, and $R^{19}$ is H; or
$R^{18}$ and $R^{19}$ are each fluoro, and $R^{20}$ is H.

In an alternative embodiment, the androgen receptor binding moiety has the structure of formula (IIIb):

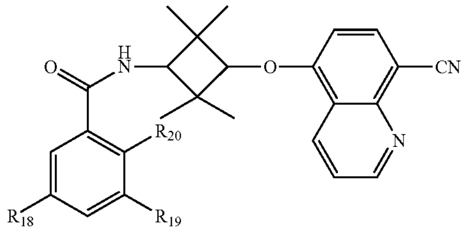

wherein $R^{18}$, $R^{19}$ and $R^{20}$ are independently H, halo or $C_{1-3}$haloalkyl.

In one embodiment of the androgen receptor binder of formula (IIIb), the compound of formula (I), or a tautomer or salt thereof:

$R^{18}$ is fluoro, and $R^{19}$ and $R^{20}$ are each H; or
$R^{18}$ is chloro, and $R^{19}$ and $R^{20}$ are each H; or
$R^{18}$ and $R^{20}$ are each fluoro, and $R^{19}$ is H; or
$R^{18}$ and $R^{19}$ are each fluoro, and $R^{20}$ is H.

In an alternative embodiment, the androgen receptor binding moiety has the structure of formula (IIIc):

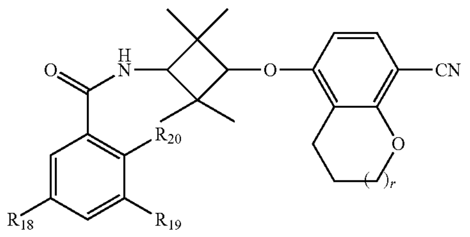

wherein:

$R^{18}$, $R^{19}$ and $R^{20}$ are independently H, halo or $C_{1-3}$haloalkyl; and r is 0 or 1.

In one embodiment of the androgen receptor binder of formula (IIIc), the compound of formula (I), or a tautomer or salt thereof, r is 0. In another embodiment, r is 1.

In one embodiment of the androgen receptor binder of formula (IIIc), the compound of formula (I), or a tautomer or salt thereof:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

Linker

The androgen receptor binding moiety of formula (III), (IIIa), (IIIb), (IIIc) is linked to the cereblon binding moiety by a group of formula (IV):

(IV)

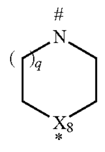

wherein * represents the point of attachment to the cereblon binder of formula (II) and #represents the point of attachment to the androgen binding moiety of formulae (III), (IIIa), (IIIb) or (IIIc);

q is 0 or 1;

$X_8$ is $CR^{15}R^{16}$;

and wherein either a) $R^{15}$ and $R^{16}$ together with the carbon atom to which they are attached join together to form a cyclobutyl ring; or b) $R^{15}$ is —($CHR^{17}$)—, $R^{16}$ is H, OH or a halo and $R^{17}$ is H or halo.

In one embodiment of the linker of formula (IV), the compound of formula (I), or a tautomer or salt thereof q is 1. In an alternative embodiment, q is 0.

In one embodiment, the linker has the structure of formula (IVa):

(IVa)

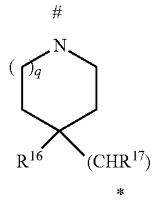

wherein * represents the point of attachment to the cereblon binder of formula (II) and #represents the point of attachment to the androgen binding moiety of formulae (III), (IIIa), (IIIb) or (IIIc);

q is 0 or 1;

$R^{16}$ is H, OH or halo; and $R^{17}$ is H or halo.

In one embodiment of the linker of formula (IV), the compound of formula (I), or a tautomer or salt thereof $R^{16}$ is H.

In one embodiment of the linker of formula (IV), the compound of formula (I), or a tautomer or salt thereof $R^{17}$ is H.

In one embodiment of the linker of formula (Na), the compound of formula (I), or a tautomer or salt thereof q is 1. In an alternative embodiment, q is 0.

PROTACs

Compounds of formula (I) are PROTACS.

In one embodiment, the invention provides a PROTAC comprising the degron of formula (II), the androgen receptor binding moiety of formula (III), and the linker of formula (Na). Such a PROTAC is a compound of formula (VII).

In one embodiment, the invention provides a compound of formula (VII), a tautomer of a compound of formula (VII), or a salt thereof:

(VII)

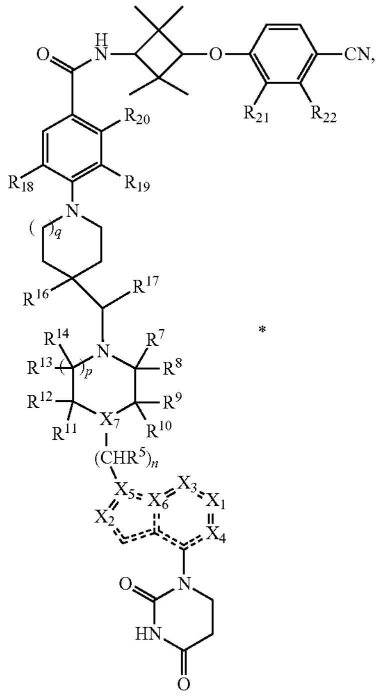

wherein:

$X_1$ is N or C—$R^1$, wherein $R^1$ is selected from the group consisting of H, halo, $C_{1-4}$alkyl, $C_{1-4}$haloalkyl, $C_{1-4}$alkoxy and —$CONR^3R^4$;

$R^3$, $R^4$ and $R^5$ are independently selected from H or $C_{1-4}$alkyl;

$X_4$ is C—$R^2$ or N, wherein $R^2$ is selected from the group consisting of H, halo, $C_{1-3}$alkyl, $C_{1-3}$haloalkyl and $C_{1-3}$alkoxy;

$X_2$ and $X_3$ are independently selected from N or CH;

$X_6$ and $X_5$ are independently selected from N or C, wherein when $X_6$ is N, $X_5$ is C;

n, p, q and r are independently 0 or 1;

$X_7$ is $CR^6$;

$R^6$, $R^7$, $R^8$, $R^9$, $R^{10}$, $R^{11}$, $R^{12}$, $R^{13}$ and $R^{14}$ are independently selected from H or halo;

$R^{16}$ is H, OH or halo;

$R^{17}$ is H or halo;

$R^{18}$, $R^{19}$ and $R^{20}$ are independently H, halo or $C_{1-3}$haloalkyl;

and wherein either iii) $R^{22}$ is selected from the group consisting of halo and —$OR^{23}$; and $R^{21}$ is independently H or methyl, wherein $R^{23}$ is $C_{1-3}$alkyl; or iv) $R^{21}$ and $R^{22}$ together with the phenyl to which they are attached join together to form a bicyclic ring selected from the group consisting of:

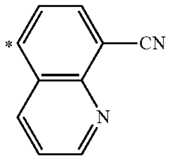 and 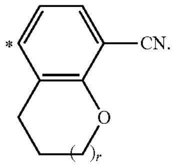

wherein the asterisks indicate the point of attachment to the oxygen atom.

In one embodiment of the compound of formula (VII), or a tautomer or salt thereof, $X_5$ is N and $X_6$ is C. In certain embodiments in which $X_5$ is N and $X_6$ is C, $X_2$ is additionally N.

In one embodiment of the compound of formula (VII), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_6$ is C and $X_1$ is C—$R^1$.

In a more particular embodiment of the compound of formula (VII), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$.

In one embodiment of the compound of formula (VII), or a tautomer or salt thereof, $R^1$ is selected from H, halo, and $C_{1-4}$haloalkyl. In a more particular embodiment, $R^1$ is H, halogen or —$CF_3$. In a more particular embodiment, $R^1$ is H, fluoro, chloro, or —$CF_3$. In a further embodiment, $R^1$ is H.

In one embodiment of the compound of formula (VII), or a tautomer or salt thereof, $R^2$ is H, fluoro, chloro or $CF_3$. In one embodiment, $R^2$ is H or fluoro.

In a more particular embodiment of the compound of formula (VII), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a more particular embodiment of compound of formula (VII), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is CH; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is CH; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In one embodiment of the compound of formula (VII), or a tautomer or salt thereof $X_5$, $X_2$ and $X_4$ are each N, $X_3$ is CH, $X_6$ is C and $X_1$ is CH.

In a more particular embodiment of the compound of formula (VII), or a tautomer or salt thereof $X_5$ is N, $X_2$ and $X_3$ are each CH, $X_6$ is C, $X_1$ is C—$R^1$ wherein $R^1$ is H or fluoro, and $X_4$ is CH.

In a more particular embodiment of the compound of formula (VII), or a tautomer or salt thereof $X_5$ and $X_2$ are each N, $X_3$ is CH, $X_6$ is C, $X_1$ is C—$R^1$ wherein $R^1$ is H or fluoro and $X_4$ is CH.

In one embodiment of the compound of formula (VII), or a tautomer or salt thereof, n is 0.

In one embodiment of the compound of formula (VII), or a tautomer or salt thereof wherein n is 1, $R^5$ is H or methyl. In a more particular embodiment, $R^5$ is H.

In one embodiment of the compound of formula (VII), or a tautomer or salt thereof, $R^6$ is H.

In one embodiment of the compound of formula (VII), or a tautomer or salt thereof, p is 1. In another embodiment, p is 0.

In one embodiment of the compound of formula (VII), or a tautomer or salt thereof, $R^7$, $R^8$, $R^9$, $R^{10}$, $R^{11}$, $R^{12}$, $R^{13}$ and $R^{14}$ are independently selected from H or fluoro. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is fluoro and $R^7$, $R^8$, $R^9$, $R^{11}$, $R^{12}$, $R^{13}$ and $R^{14}$ are each H. In an alternative embodiment, $R^7$, $R^8$, $R^9$, $R^{10}$, $R^{11}$, $R^{12}$, $R^{13}$ and $R^{14}$ are each H.

In one embodiment of the compound of formula (VII), or a tautomer or salt thereof, $R^{18}$, $R^{19}$ and $R^{20}$ are each independently H or halo. In a more particular embodiment, $R^{18}$, $R^{19}$ and $R^{20}$ are each independently H or fluoro. In one embodiment, $R^{18}$ is halo, and $R^{19}$ and $R^{20}$ are each independently H or halo. In one embodiment, $R^{18}$ is fluoro or chloro, and $R^{19}$ and $R^{20}$ are each independently H or fluoro. In one embodiment, $R^{18}$ is fluoro, and $R^{19}$ and $R^{20}$ are each independently H.

In one embodiment of the compound of formula (VII), or a tautomer or salt thereof:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

In one embodiment of the compound of formula (VII), or a tautomer or salt thereof $R^{16}$ is H.

In one embodiment of the compound of formula (VII), or a tautomer or salt thereof $R^{17}$ is H.

In one embodiment of the compound of formula (VII), or a tautomer or salt thereof q is 1. In an alternative embodiment, q is 0.

In another embodiment, the invention provides a compound of formula (V), a tautomer of a compound of formula (V), or a salt thereof:

(V)

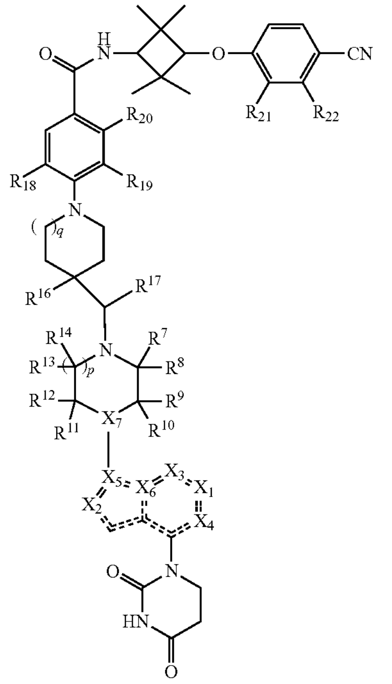

wherein:

$X_1$ is N or C—$R^1$ wherein $R^1$ is selected from the group consisting of H, halo, and $C_{1-4}$haloalkyl;

$X_4$ is C—$R^2$ or N wherein $R^2$ is selected from the group consisting of H, halo and $C_{1-3}$haloalkyl;

$X_2$ and $X_3$ are independently selected from N or CH;

$X_6$ and $X_5$ are independently selected from N or C, wherein when $X_6$ is N, $X_5$ is C;

p and q are independently 0 or 1;

$X_7$ is $CR^6$;

$R^6$, $R^7$, $R^8$, $R^9$, $R^{10}$, $R^{11}$, $R^{12}$, $R^{13}$, $R^{14}$ and $R^{17}$ are independently selected from H or halo;

$R^{16}$ is H, OH or halo;

$R^{18}$, $R^{19}$ and $R^{20}$ are independently H, halo or $C_{1-3}$haloalkyl;

$R^{22}$ is selected from the group consisting of halo and $OR^{23}$ $R^{21}$ is independently H or methyl, and $R^{23}$ is $C_{1-3}$alkyl.

In one embodiment of the compound of formula (V), or a tautomer or salt thereof, $X_5$ is N and $X_6$ is C. In certain embodiments in which $X_5$ is N and $X_6$ is C, $X_2$ is additionally N.

In one embodiment of the compound of formula (V), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_6$ is C and $X_1$ is C—$R^1$.

In a more particular embodiment of the compound of formula (V), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$.

In one embodiment of the compound of formula (V), or a tautomer or salt thereof, $R^1$ is H, halo or —$CF_3$. In a more particular embodiment, $R^1$ is H, fluoro, choro, or —$CF_3$.

In one embodiment of the compound of formula (V), or a tautomer or salt thereof, $R^2$ is H, fluoro, chloro or $CF_3$. In one embodiment, $R^2$ is H or fluoro.

In one embodiment of the compound of formula (V), or a tautomer or salt thereof:

$X_5$ is N, $X_2$ and $X_3$ are each CH, $X_5$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a particular embodiment of the compound of formula (V), or a tautomer or a salt thereof: $X_5$, $X_2$ and $X_4$ are each N, $X_1$ and $X_3$ are each CH and $X_5$ is C.

In a more particular embodiment of the compound of formula (V), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is CH; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is CH; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a more particular embodiment of the compound of formula (V), or a tautomer or salt thereof, $X_5$ is N, $X_2$ and $X_3$ are each CH, $X_6$ is C, $X_1$ is C—$R^1$ wherein $R^1$ is H or fluoro, and $X_4$ is CH.

In one embodiment of the compound of formula (V), or a tautomer or salt thereof, $X_5$ and $X_2$ are each N, $X_3$ is CH, $X_6$ is C, $X_1$ is C—$R^1$ wherein $R^1$ is H or fluoro and $X_4$ is CH.

In one embodiment of the compound of formula (V), or a tautomer or salt thereof, $R^6$ is H.

In one embodiment of the compound of formula (V), or a tautomer or salt thereof, p is 1. In another embodiment, p is 0.

In one embodiment of the compound of formula (V), or a tautomer or salt thereof, $R^7$, $R^8$, $R^9$, $R^{10}$, $R^{11}$, $R^{12}$, $R^{13}$ and $R^{14}$ are independently selected from H or fluoro. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is fluoro and $R^7$, $R^8$, $R^9$, $R^{11}$, $R^{12}$, $R^{13}$ and $R^{14}$ are each H. In an alternative embodiment, $R^7$, $R^8$, $R^9$, $R^{10}$, $R^{11}$, $R^{12}$, $R^{13}$ and $R^{14}$ are each H.

In one embodiment of the compound of formula (V), or a tautomer or salt thereof, $R^{22}$ is selected from the group consisting of chloro, methoxy and ethoxy. In one embodiment, $R^{22}$ is chloro. In an alternative embodiment, $R^{22}$ is methoxy.

In one embodiment of the compound of formula (V), or a tautomer or salt thereof, $R^{21}$ is H.

In one embodiment of the compound of formula (V), or a tautomer or salt thereof:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

In a particular embodiment of the compound of formula (V), or a tautomer or a salt thereof: $X_5$, $X_2$ and $X_4$ are each N, $X_1$ and $X_3$ are each CH, $X_6$ is C, $X_7$ CH, $R^7$, $R^8$, $R^9$, $R^{10}$, $R^{11}$, $R^{12}$, $R^{13}$, and $R^{14}$ are each H, p is 0, $R^{16}$ and $R^{17}$ are each H, $R^{18}$ is F, $R^{19}$, $R^{20}$ and $R^{21}$ are each H and $R^{22}$ is methoxy.

In one embodiment, the invention provides a compound of formula (VI), a tautomer of a compound of formula (VI), or a salt thereof:

(VI)

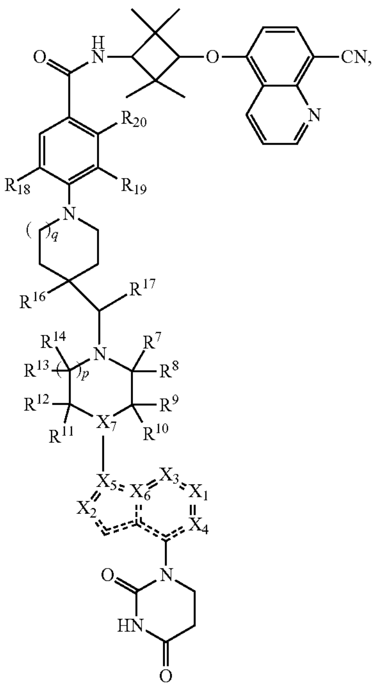

wherein:

$X_1$ is N or C—$R^1$ wherein $R^1$ is selected from the group consisting of H, halo, and $C_{1-4}$haloalkyl;

$X_4$ is C—$R^2$ or N wherein $R^2$ is selected from the group consisting of H, halo and $C_{1-3}$haloalkyl;

$X_2$ and $X_3$ are independently selected from N or CH;

$X_6$ and $X_5$ are independently selected from N or C, wherein when $X_6$ is N, $X_5$ is C;

p and q are independently 0 or 1;

$X_7$ is $CR^6$;

$R^6$, $R^7$, $R^8$, $R^9$, $R^{10}$, $R^{11}$, $R^{12}$, $R^{13}$, $R^{14}$ and $R^{17}$ are independently selected from H or halo;

$R^{16}$ is H, OH or halo;

$R^{18}$, $R^{19}$ and $R^{20}$ are independently H, halo or $C_{1-3}$haloalkyl.

In one embodiment of the compound of formula (VI), or a tautomer or salt thereof, $X_5$ is N and $X_6$ is C. In certain embodiments in which $X_5$ is N and $X_6$ is C, $X_2$ is additionally N.

In one embodiment of the compound of formula (VI), or a tautomer or salt thereof:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_6$ is C and $X_1$ is C—$R^1$.

In a more particular embodiment of the compound of formula (VI), or a tautomer or salt thereof:

$X_5$ is N, $X_2$ and $X_3$ are each CH, $X_6$ is C, $X_1$ is C—$R^1$ and 4 is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$.

In one embodiment of the compound of formula (VI), or a tautomer or salt thereof, $R^1$ is H, halo or —$CF_3$. In a more particular embodiment, $R^1$ is H, fluoro, chloro, or —$CF_3$.

In one embodiment of the compound of formula (VI), or a tautomer or salt thereof, $R^2$ is H, fluoro, chloro or $CF_3$. In one embodiment, $R^2$ is H or fluoro.

In one embodiment of the compound of formula (VI), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is C—$R^2$ wherein $R^2$ is H or fluoro; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a more particular embodiment of the compound of formula (VI), or a tautomer or salt thereof:

$X_5$ is N, $X_2$ and $X_3$ are each CH, $X_6$ is C, $X_1$ is C—$R^1$ wherein $R^1$ is H, fluoro, chloro or —$CF_3$, and $X_4$ is CH; or $X_5$ and $X_2$ are each N, $X_3$ is CH, $X_6$ is C, $X_1$ is C—$R^1$ wherein $R^1$ is H, fluoro, chloro or —$CF_3$, and $X_4$ is CH; or $X_5$ and $X_4$ are each N, $X_2$ and $X_3$ are each CH, $X_6$ is C and $X_1$ is CH; or $X_5$, $X_2$ and $X_3$ are each N, $X_6$ is C, $X_1$ is C—$R^1$ and $X_4$ is CH; or $X_5$, $X_2$ and $X_4$ are each N, $X_3$ is CH, $X_6$ is C and $X_1$ is CH.

In a more particular embodiment of the compound of formula (VI), or a tautomer or salt thereof, $X_5$ is N, $X_2$ and $X_3$ are each CH, $X_6$ is C, $X_1$ is C—$R^1$ wherein $R^1$ is H or fluoro, and $X_4$ is CH.

In one embodiment of the compound of formula (VI), or a tautomer or salt thereof, $X_5$ and $X_2$ are each N, $X_3$ is CH, $X_6$ is C, $X_1$ is C—$R^1$ wherein $R^1$ is H or fluoro and $X_4$ is CH.

In one embodiment of the compound of formula (VI), or a tautomer or salt thereof, $R^6$ is H.

In one embodiment of the compound of formula (VI), or a tautomer or salt thereof, p is 1. In another embodiment, p is 0.

In one embodiment of the compound of formula (VI), or a tautomer or salt thereof, $R^7$, $R^8$, $R^9$, $R^{10}$, $R^{11}$, $R^{12}$, $R^{13}$ and $R^{14}$ are independently selected from H or fluoro. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is H or halo and $R^7$, $R^8$, $R^9$, $R^{11}$, $R^{12}$, $R^{13}$ and $R^{14}$ are each H. In another embodiment, $R^{10}$ is fluoro and $R^7$, $R^8$, $R^9$, $R^{11}$, $R^{12}$, $R^{13}$ and $R^{14}$ are each H. In an alternative embodiment, $R^7$, $R^8$, $R^9$, $R^{10}$, $R^{11}$, $R^{12}$, $R^{13}$ and $R^{14}$ are each H.

In one embodiment of the compound of formula (V), or a tautomer or salt thereof:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

Compounds of formulae (V) or (VI), or a tautomer or salt thereof comprise an androgen receptor binding moiety of formula (III). The androgen receptor binding moiety of formula (III) can bind to certain mutated versions of the androgen receptor including the dual mutant (T878A/L702H) Androgen Receptor. Compounds of formula (V) or (VI), or tautomers or salts thereof are therefore expected to be useful for the treatment of prostate cancer, including castration resistant prostate cancer.

Compounds of formula (I), (V) and (VI) exist in tautomeric forms. The predominant form of these compounds is the lactam form (depicted in the structures). It is to be understood that any reference to a named compound or a structurally depicted compound is intended to encompass all tautomers of such compound.

Because of their use in medicine, salts of PROTACs including the PROTAC of formula (I), (V) and (VI) are preferably pharmaceutically acceptable.

In one embodiment, the invention provides a compound that is N-((1r,3r)-3-((8-cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide or a tautomer, or a pharmaceutically acceptable salt thereof. As demonstrated in the examples, spray dried dispersions of this compound in 1% methylcellulose (aqueous) achieve similar oral exposure in rats to that achieved by administration of the compound in 100% PEG400 (which is typically considered to provide a theoretical maximum exposure) demonstrating that conventional techniques for enhancing bioavailability can be used with this compound. The oral exposure achieved using 30 mg/kg SDD 1:4 API:HPMCAS-LG or SDD 1:3.5:0.5 API:HPMC-AS HG:SLS in 1% methylcellulose (aq.) is evidence of the developability of this compound.

In one embodiment, the invention provides a compound that is N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a tautomer, or a pharmaceutically acceptable salt thereof.

In one embodiment, the invention provides pharmaceutically acceptable salt of a compound that is N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a tautomer thereof, wherein the pharmaceutically acceptable salt is a benzenesulfonate (besylate), ethanesulfonate (esylate), hydrochloride, methanesulfonate (mesylate), naphthalene-1,5-disulfonate (napadisylate), or p-toluenesulfonate (tosylate) salt.

In a more particular embodiment, the invention provides a compound that is a formic acid salt of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a tautomer thereof.

In another embodiment, the invention provides a compound that is N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide free base or a tautomer thereof. In one embodiment, N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide free base thereof, which is in crystalline form.

In one embodiment, the invention provides a crystalline form of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide free base, which crystalline form has an X-ray powder diffraction pattern using CuKα radiation comprising characteristic peaks at 2°theta values of 6.4°±0.2°, 16.7°±0.2° and 17.4°±0.2°.

Pharmaceutically acceptable salts include, amongst others, those described in Berge, J. Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Suitable pharmaceutically acceptable salts include acid addition salts. Such acid addition salts can be formed by reaction of a compound of formula (I), (V), (VI) (which, for example contains a basic amine or other basic functional group) with the appropriate acid, optionally in a suitable solvent such as an organic solvent, to give the salt which can be isolated by a variety of methods, including crystallisation and filtration.

Salts may be prepared in situ during the final isolation and purification of a compound of formula (I), (V) or (VI). If a basic compound of formula (I), (V) or (VI) is isolated as a salt, the corresponding free base form of that compound may be prepared by any suitable method known to the art, including treatment of the salt with an inorganic or organic base.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate. In one embodiment, the pharmaceutically acceptable acid addition salt is a formate salt. In another embodiment, the pharmaceutically acceptable acid addition salt is a benzenesulfonate (besylate), ethanesulfonate (esylate), hydrochloride, methanesulfonate (mesylate), naphthalene-1,5-disulfonate (napadisylate), or p-toluenesulfonate (tosylate) salt.

It will be understood that if a compound of formula (I), V) or (VI) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of formula (I), (V), (VI) are included within the scope of the invention, including sub-stoichiometric salts, for example where a counterion contains more than one acidic proton.

Advantageously, certain compounds of formula (I), (V), (VI) have high levels of in vivo exposure following administration of the compound as a solid dose.

Process for Preparing Compounds

The process to be utilized in the preparation of compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of Formula (II) and (III) are set forth below. All starting material and reagents described in the below general experimental schemes are commercially available or can be prepared by methods known to one skilled in the art. It is noted for completeness that the linker is not typically synthesised as a separate intermediate. Rather, the linker can be synthesised attached to either the compound of formula (III) or (IV), or part of the linker can be synthesised attached to the compound of formula (III) and the other part of linker can be synthesised attached to the compound of formula (IV), by standard techniques in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Scheme 1 provides exemplary processes of synthesis for preparing compounds of formula (II). In General Scheme 1, $X_1$, $X_2$, $X_3$, $X_4$, $X_5$, $X_6$, $X_7$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, n and p are as defined as for formula (Iaa), $PG_1$ and $PG_2$ are suitable protecting groups, L is a suitable leaving group and Hal is Br or I. Compounds of formula (XVIII) may be prepared by methods described in Chemistry—A European Journal (2011), 17(49), 13698-13705.

General Scheme 1
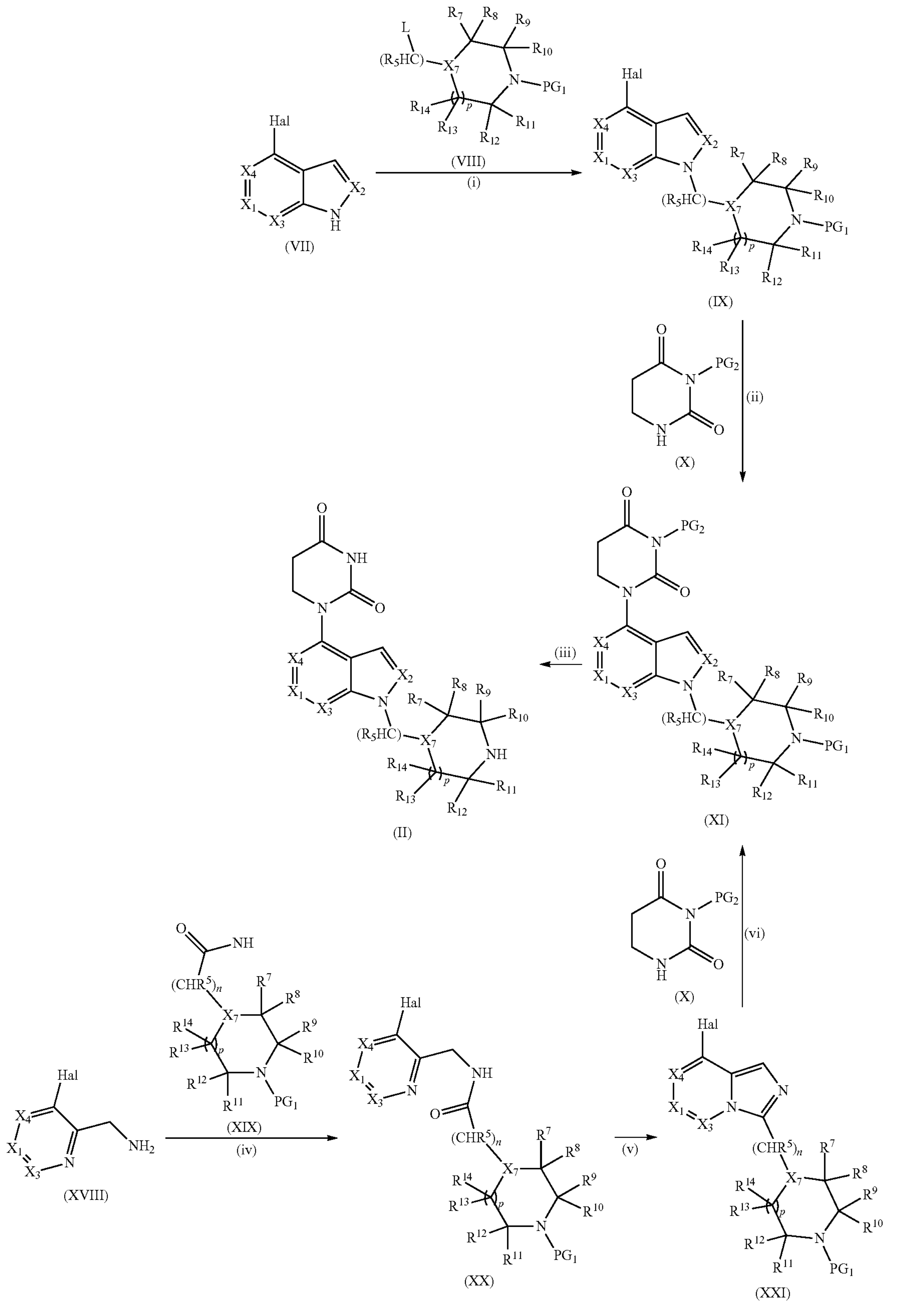

When L is bromo, methylsulfonyloxy or trifluoromethylsulfonyloxy, step (i) may comprise treatment with sodium hydride followed by reaction a compound of formula (VIII). Step (i) may alternatively comprise reaction with a compound of formula (VIII) in the presence of a base such as caesium carbonate.

Steps (ii) and (vi) are amination reactions. The reaction may be catalysed by a palladium catalyst/ligand system such as BrettPhos Pd G3 precatalyst and BrettPhos ligand in the presence of a suitable base such as tribasic potassium phosphate. Alternatively, it may be catalysed by copper(I) iodide in the presence of trans-N,N'-dimethylcyclohexane-1,2-diamine and a suitable base such as potassium carbonate.

Step (iii) is a deprotection reaction. Where $PG_1$ is a tert-butoxycarbonyl group and $PG_2$ is a trimethylsilylethoxymethyl group, deprotection may be effected by treatment with trifluoroacetic acid.

Step (iv) is an amide formation by reaction with an amine in the presence of HATU and a suitable base such as DIPEA or triethylamine.

Step (v) is a two part reaction in which the compound of formula (XX) is treated with phosphorous oxychloride, followed by di-tert-butyl dicarbonate in the presence of a suitable base such as triethylamine.

General Scheme 2 provides exemplary processes of synthesis for preparing compounds of formula (III). In General Scheme 2, $R^{18}$, $R^{19}$, $R^{20}$, $R^{21}$ and $R^{22}$ are as defined as for formula (III) and $PG_3$ and $PG_4$ are suitable protecting groups.

General Scheme 2

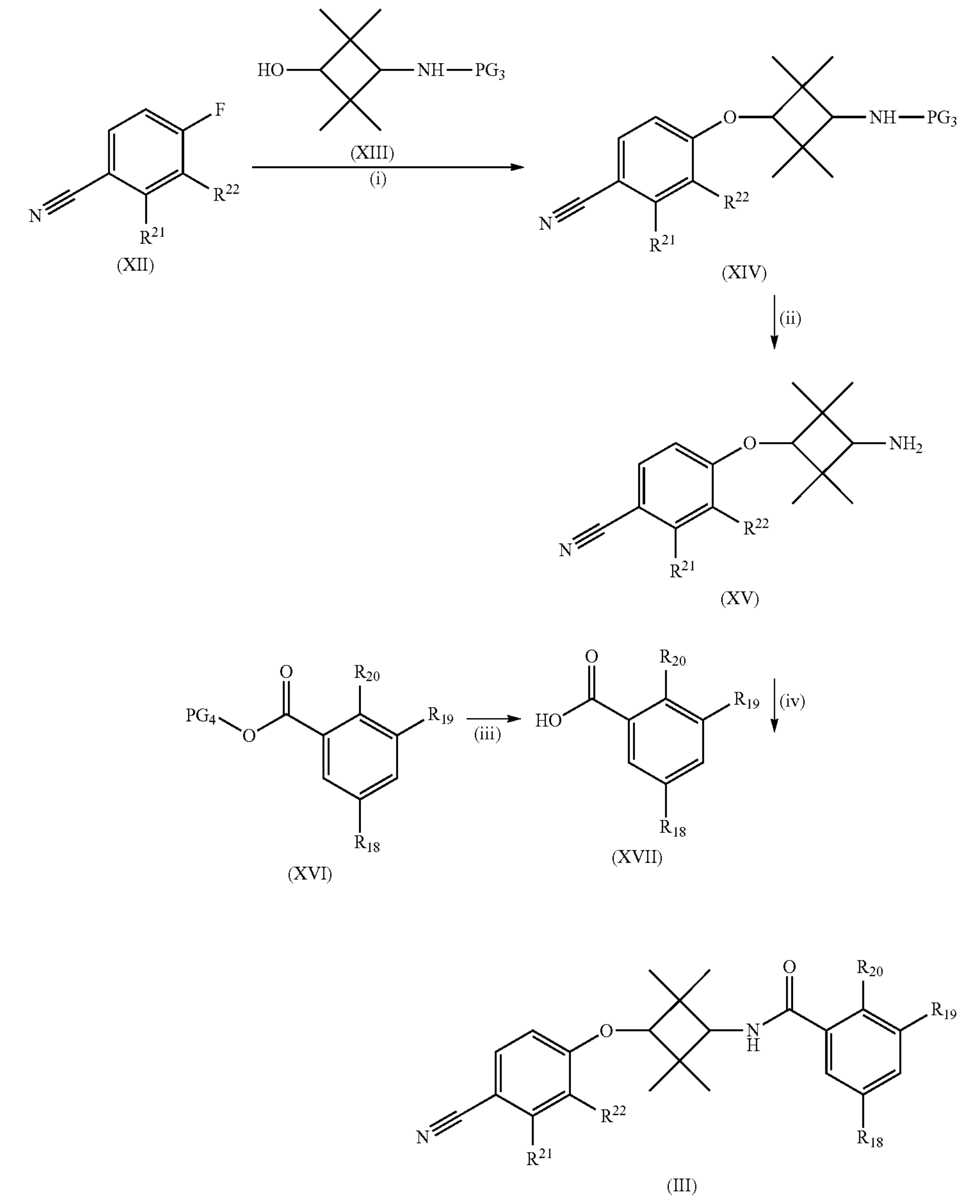

Step (i) treatment of a compound of formula (XII) with sodium hydride or cesium carbonate followed by reaction with a compound of formula (XIII).

Step (ii) is a deprotection reaction. When $PG_3$ is tert-butoxycarbonyl, deprotection may be achieved by treatment with an acid such as HCl or TFA.

Step (iii) is also a deprotection reaction. When $PG_4$ is methyl or ethyl, deprotection may be achieved by treatment with an alkali such as sodium hydroxide. When $PG_4$ is tert-butyl, deprotection may be achieved by treatment with an acid such as TFA.

Step (iv) is an amide formation by reaction with an amine in the presence of HATU and a suitable base such as DIPEA or triethylamine. Alternatively, PyBOP may be used as a reagent in the presence of ethyl (E)-2-cyano-2-(hydroxyimino)acetate and N-methylmorpholine or OxymaPure and DIPEA.

Pharmaceutical Compositions

PROTACs of the invention or pharmaceutically acceptable salts thereof may be administered by any convenient route. In particular embodiments, the PROTAC or pharmaceutically acceptable salt thereof may be administered by orally, parenterally, intranasally or by inhalation. In one embodiment, the PROTAC or pharmaceutically acceptable salt thereof is administered in a pharmaceutical composition. In one embodiment, the PROTAC or pharmaceutically acceptable salt thereof is formulated in a pharmaceutical composition adapted for oral or parenteral administration, or for administration intranasally or by inhalation.

According to one aspect, the invention provides a pharmaceutical composition comprising a PROTAC or pharmaceutically acceptable salt thereof and a pharmaceutically acceptable excipient. According to another aspect, the invention provides a process for the preparation of a pharmaceutical composition comprising admixing a PROTAC or pharmaceutically acceptable salt thereof with a pharmaceutically acceptable excipient.

In certain embodiments, spay dried dispersions of the PROTAC or pharmaceutically acceptable salt thereof can be included in the pharmaceutical composition.

Where the PROTAC or pharmaceutically acceptable salt is N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a pharmaceutically acceptable salt thereof, spray dried dispersions may be included in the pharmaceutical compositions. In one embodiment, the spray dried formulation comprises hypromellose acetate succinate, and in a more particular embodiment it comprises HPMCAS-LG. The ratio of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a pharmaceutically acceptable salt thereof to hypromellose acetate succinate or HPMCAS-LG is in the range 1:2 to 1:4. In a particular embodiment, the ratio of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a pharmaceutically acceptable salt thereof to hypromellose acetate succinate or HPMCAS-LG is 1:2. In another embodiment, the ratio of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a pharmaceutically acceptable salt thereof to hypromellose acetate succinate or HPMCAS-LG is 1:3. In a further embodiment, the ratio of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a pharmaceutically acceptable salt thereof to hypromellose acetate succinate or HPMCAS-LG is 1:4.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for nasal administration can comprise a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the PROTAC or pharmaceutically acceptable salt thereof.

Pharmaceutical formulations adapted for administration by inhalation include fine particle dusts or mists, which may be generated by means of various types of metered, dose pressurized aerosols, nebulizers or insufflators.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations described herein may include other agents conventional in the art having regard to the type of formulation in question, for example those suitable for oral administration may include flavouring agents.

The present invention also provides unitary pharmaceutical compositions in which the PROTAC or pharmaceutically acceptable salt thereof and one or more other therapeutic agent(s) may be administered together. When a PROTAC or pharmaceutically acceptable salt thereof is used in combination with a second therapeutic agent, the dose of each therapeutic agent may differ from the dose of that therapeutic agent when used alone.

Medical Use

Compounds of Formula (I), (V), (VI), or tautomers or pharmaceutically acceptable salts thereof and PROTACs capable of degrading the androgen receptor and are useful in medicine.

Accordingly, in one aspect the invention provides a compound of formula (I), (V), (VI), or a tautomer or a pharmaceutically acceptable salt thereof for use in therapy.

More particularly, compounds of formula (I), (V), (VI), or a tautomer or a pharmaceutically acceptable salt thereof are useful in the treatment of cancer, benign prostatic hyperplasia, ovarian cysts, polycystic ovary syndrome or Kennedy's Disease.

Accordingly, in one aspect, the invention provides a compound of formula (I), (V), (VI), or a tautomer or a pharmaceutically acceptable salt thereof for use in in the treatment of cancer, benign prostatic hyperplasia, ovarian cysts, polycystic ovary syndrome or Kennedy's Disease.

In another embodiment, the invention provides use of a compound of formula (I), (V), (VI), or a tautomer or a pharmaceutically acceptable salt thereof in the manufacture of the medicament for the treatment of cancer, benign prostatic hyperplasia, ovarian cysts, polycystic ovary syndrome or Kennedy's Disease.

In another embodiment, the invention provides a method of treating cancer, benign prostatic hyperplasia, ovarian cysts, polycystic ovary syndrome or Kennedy's Disease in a subject, which method comprises administering to said subject a therapeutically effective amount of a compound of formula (I), (V), (VI), or a tautomer or a pharmaceutically acceptable salt thereof.

Suitably, the subject is a mammal. In a particular embodiment, the subject is human.

In one embodiment, the cancer is selected from prostate cancer, ovarian cancer, breast cancer, endometrial cancer, bladder cancer, pancreatic cancer hepatocellular cancer and salivary gland cancer. In a more particular embodiment, the cancer is selected from prostate cancer or breast cancer.

In one embodiment, the prostate cancer is androgen dependent prostate cancer. In another embodiment, treatment is secondary to androgen ablation therapy. In one embodiment, treatment is secondary to treatment with abiraterone acetate or hydroxyflutamide.

In a more particular embodiment, the prostate cancer is castration resistant prostate cancer. In one embodiment, the prostate cancer is metastatic castration resistant prostate cancer. In another embodiment, the prostate cancer is non-metastatic castration resistant prostate cancer. In one embodiment, the prostate cancer is locally advanced prostate cancer.

In one embodiment, the breast cancer is triple negative breast cancer.

In one particular embodiment, the disorder treated is Kennedy's Disease.

When a compound of a compound of formula (I), (V), (VI), or a tautomer or a pharmaceutically acceptable salt thereof is intended for use in the treatment of cancer, it may be used in combination with one or more additional anti-cancer agents, for example, a PARP inhibitor. Accordingly, in one embodiment, the invention provides a combination of a compound of formula (I), (V), (VI), or a tautomer or a pharmaceutically acceptable salt thereof with an active pharmaceutical ingredient that is an anti-cancer agent, such as a PARP inhibitor.

NUMBERED EMBODIMENTS

Embodiment 1. A compound of formula (I), a tautomer of a compound of formula (I), or a salt thereof (I)

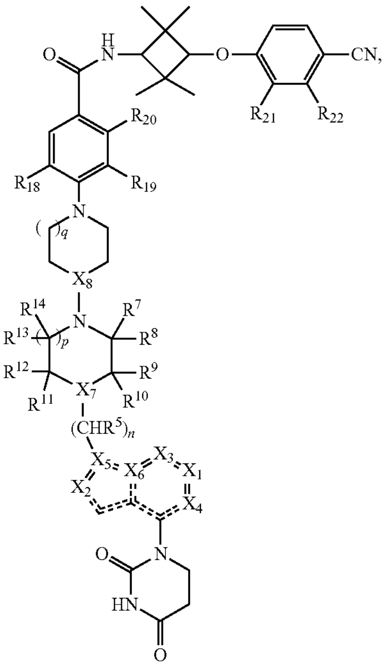

wherein:

$X_1$ is N or C—$R^1$ wherein $R^1$ is selected from the group consisting of H, halo, $C_{1-4}$alkyl, $C_{1-4}$haloalkyl, $C_{1-4}$alkoxy and —$CONR^3R^4$;

$R^3$, $R^4$ and $R^5$ are independently selected from H or $C_{1-4}$alkyl;

$X_4$ is C—$R^2$ or N wherein $R^2$ is selected from the group consisting of H, halo, $C_{1-3}$alkyl, $C_{1-3}$haloalkyl and $C_{1-3}$alkoxy;

$X_2$ and $X_3$ are independently selected from N or CH;

$X_6$ and $X_5$ are independently selected from N or C, wherein when $X_6$ is N, $X_5$ is C;

n, p, q and r are independently 0 or 1;

$X_7$ is $CR^6$;

$R^6$, $R^7$, $R^8$, $R^9$, $R^{10}$, $R^{11}$, $R^{12}$, $R^{13}$ and $R^{14}$ are independently selected from H or halo;

$X_8$ is $CR^{15}R^{16}$ and wherein either a) $R^{15}$ and $R^{16}$ together with the carbon atom to which they are attached join together to form a cyclobutyl ring; or b) $R^{15}$ is —($CHR^{17}$)—, $R^{16}$ is H, OH or a halo, and $R^{17}$ is H or halo;

$R^{18}$, $R^{19}$ and $R^{20}$ are independently H, halo or $C_{1-3}$haloalkyl;

and wherein either i) $R^{22}$ is selected from the group consisting of halo and —$OR^{23}$ and $R^{21}$ is independently H or methyl, wherein $R^{23}$ is $C_{1-3}$alkyl; or ii) $R^{21}$ and $R^{22}$ together with the phenyl to which they are attached join together to form a bicyclic ring selected from the group consisting of:

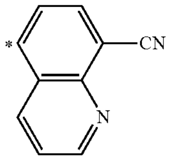 and 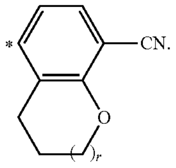

Embodiment 2. A compound of formula (I), a tautomer of a compound of formula (I), or a salt thereof according to embodiment 1, wherein $R^{23}$ is selected from the group consisting of halo and —$OR^{23}$ and $R^{21}$ is independently H or methyl, wherein $R^{23}$ is $C_{1-3}$alkyl.

Embodiment 3. A compound of formula (I), a tautomer of a compound of formula (I), or a salt thereof according to embodiment 1, wherein $R^{21}$ and $R^{22}$ together with the phenyl to which they are attached join together to form a bicyclic ring selected from the group consisting of:

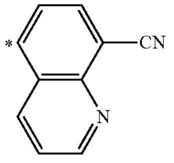 and 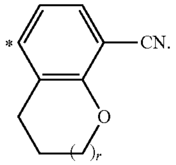

Embodiment 4. A compound of formula (I), a tautomer of a compound of formula (I), or a salt thereof according to embodiment 3, wherein $R^{21}$ and $R^{22}$ together with the phenyl to which they are attached join together to form a bicyclic ring having the following structure:

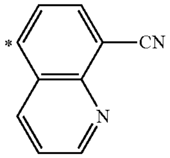

Embodiment 5. A compound of formula (I), a tautomer of a compound of formula (I), or a salt thereof according to any preceding embodiment, wherein $X_8$ is $CR^{15}R^{16}$, wherein $R^{15}$ is —($CHR^{17}$)—, $R^{16}$ is H, OH or a halo and $R^{17}$ is H or halo.

Embodiment 6. A compound of formula (I), a tautomer of a compound of formula (I), or a salt thereof according to any preceding embodiment, wherein:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_6$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_6$ is C and $X_1$ is C—$R^1$.

Embodiment 7. A compound of formula (I), a tautomer of a compound of formula (I), or a salt thereof according to any preceding embodiment, wherein $R^1$ is H, halogen or —$CF_3$.

Embodiment 8. A compound of formula (I), a tautomer of a compound of formula (I), or a salt thereof according to any preceding embodiment, wherein $R^2$ is H or fluoro.

Embodiment 9. A compound of formula (I), a tautomer of a compound of formula (I), or a salt thereof according to any preceding embodiment, wherein n is 0.

Embodiment 10. A compound of formula (I), a tautomer of a compound of formula (I), or a salt thereof according to any preceding embodiment, wherein $R^6$ is H.

Embodiment 11. A compound of formula (I), a tautomer of a compound of formula (I), or a salt thereof according to any preceding embodiment, wherein $R^{10}$ is H or halo and $R^7$, $R^8$, $R^9$, $R^{11}$, $R^{12}$, $R^{13}$ and $R^{14}$ are each H.

Embodiment 12. A compound of formula (I), a tautomer of a compound of formula (I), or a salt thereof according to any preceding embodiment, wherein $R^{18}$, $R^{19}$ and $R^{20}$ are each independently H or halo.

Embodiment 13. A compound of formula (I), a tautomer of a compound of formula (I), or a salt thereof according to embodiment 12, wherein:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

Embodiment 14. A compound of formula (I), a tautomer of a compound of formula (I), or a salt thereof according to any preceding embodiment, wherein:

$R^{22}$ is selected from the group consisting of halo and —$OR^{23}$;

$R^{21}$ is independently H or methyl; and $R^{23}$ is $C_{1-3}$alkyl.

Embodiment 15. A compound of formula (I), a tautomer of a compound of formula (I), or a salt thereof according to embodiment 14, wherein $R^{22}$ is selected from the group consisting of chloro, methoxy and ethoxy.

Embodiment 16. A compound of formula (I), a tautomer of a compound of formula (I), or a salt thereof according to any preceding embodiment, wherein $R^{21}$ is H.

Embodiment 17. A compound of formula (I), a tautomer of a compound of formula (I), or a salt thereof according to any preceding embodiment, wherein $R^{15}$ is —($CHR^{17}$)—, $R^{16}$ is H, OH or a halo, and $R^{17}$ is H or halo.

Embodiment 18. A compound of formula (I), a tautomer of a compound of formula (I), or a salt thereof according to embodiment 17, wherein $R^{16}$ is H.

Embodiment 19. A compound of formula (I), a tautomer of a compound of formula (I), or a salt thereof according to any preceding embodiment, wherein $R^{17}$ is H.

Embodiment 20. A compound of formula (I), a tautomer of a compound of formula (I), or a salt thereof according to any preceding embodiment, wherein q is 1.

Embodiment 21. A compound of formula (I), a tautomer of a compound of formula (I), or a salt thereof according to any one of embodiments 1 to 18, wherein q is 0.

Embodiment 22. A pharmaceutical composition comprising the compound, tautomer or pharmaceutically acceptable salt thereof according to any preceding embodiment and a pharmaceutically acceptable excipient.

Embodiment 23. A compound of formula (I), tautomer or pharmaceutically acceptable salt thereof as defined in any one of embodiments 1 to 21 for use in the treatment of cancer, benign prostatic hyperplasia, ovarian cysts, polycystic ovary syndrome or Kennedy's Disease.

Embodiment 24. Use of the compound, tautomer or pharmaceutically acceptable salt thereof as defined in any one of embodiments 1 to 21, in the manufacture of a medicament for use in the treatment of cancer, benign prostatic hyperplasia, ovarian cysts, polycystic ovary syndrome or Kennedy's Disease.

Embodiment 25. A method of treating a disorder selected from the group consisting of cancer, benign prostatic hyperplasia, ovarian cysts, polycystic ovary syndrome and Kennedy's Disease, comprising administering to a subject a therapeutically effective amount of the compound, tautomer or pharmaceutically acceptable salt thereof as defined in any one of embodiments 1 to 21 or the pharmaceutical composition according to embodiment 22.

EXAMPLES

Abbreviations aq Aqueous
Boc tert-Butoxycarbonyl
CMBP Cyanomethylenetributylphosphorane
DCM Dichloromethane
DIAD Diisopropyl azodicarboxylate
DIPEA N,N-Diisopropylethylamine
DMAc N,N-Dimethylacetamide
DMP Dess-Martin Periodinane
DMAP 4-(Dimethylamino)pyridine
DMF N,N-Dimethylformamide
DMSO Dimethyl sulfoxide
EtOAc Ethyl acetate
EtOH Ethanol
Eq Equivalent(s)
FHT Fixed hold time
g Gram(s)
h Hour(s)
HATU 1-[Bis(dimethylamino)methylene]-1H-1,2,3-triazolo[4,5-b]pyridinium 3-oxide hexafluorophosphate
LCMS Liquid chromatography mass spectrometry
MDAP Mass directed auto-preparative HPLC
MeCN Acetonitrile
MeOH Methanol
min Minute(s)
NMP N-methyl-2-pyrrolidone
NMR Nuclear Magnetic Resonance
Prep HPLC Preparative high-performance liquid chromatography
Rt Retention time
rt Room temperature
TBME tert-Buty methyl ether
TFA Trifluoroacetic acid
THF Tetrahydrofuran
Wt Weight Purification and Characterisation Methods Nuclear Magnetic Resonance (NMR)

NMR spectra were recorded using a Bruker DPX400. Chemical shifts (δ) are reported in parts per million (ppm) relative to tetramethylsilane and coupling constants (J) in Hz. The following abbreviations are used for multiplicities: s=singlet; br. s=broad singlet; d=doublet; t=triplet; q=quartet; spt=septet; m=multiplet; dd=doublet of doublets. If not specifically stated, the NMR experiments were run at 30° C.

Liquid Chromatography Mass Spectroscopy (LCMS)

LCMS was conducted using one of the following methods:

Formic Method A ("Formic A")

LC Conditions

Column: 30 mm×2.1 mm×1.7 μm, or 50 mm×2.1 mm, 1.7 μm CSH C18
Temperature: 40° C.
Injection volume: 0.2 or 0.3 μL
Mobile phases: A=0.1% v/v solution of formic acid in water and B=0.1% v/v solution of formic acid in MeCN Flow rate = 1 mL/min Gradient:

| Time (min) | % A | % B |
|---|---|---|
| 0 | 97 | 3 |
| 1.5 | 3 | 97 |
| 1.9 | 3 | 97 |
| 2.0 | 98 | 2 |

The UV detection was a summed signal from wavelength of 210 nm to 350 nm.

MS Conditions

MS: Waters QDA
Ionisation mode: Alternate-scan Positive and Negative Electrospray
Scan Range: 100 to 1000 AMU
Scan Frequency: 5 hertz Formic Method B ("Formic B")

LC Conditions

Column: Acquity UPLC BEH C18 1.7 μm 3×50 mm
Temperature: 50° C.
Injection volume: 1 μL
Mobile phases: A=0.1% formic acid in water and B=0.1% formic acid in MeCN
Gradient:

| Time (min) | % B | Flow rate (mL/min) |
|---|---|---|
| 0 | 5 | 0.8 |
| 1.4 | 100 | 0.8 |
| 1.9 | 100 | 0.8 |
| 2 | 5 | 0.8 |

The UV detection was a summed signal from wavelength of 210 nm to 500 nm.

MS: Waters SQD
Ionisation mode: Alternate-scan Positive and Negative Electrospray
Scan Range: 100 to 1200 AMU
Scan Frequency: 2.5 Hertz High pH Method A ("High pH A")

LC Conditions

Column: 30 mm×2.1 mm×1.7 μm, or 50 mm×2.1 mm, 1.7 μm CSH C18
Temperature: 40° C.
Injection volume: 0.3 μL
Mobile phases: A=10 mM ammonium bicarbonate in water adjusted to pH 10 with ammonia solution and B=MeCN Flow rate = 1 mL/min Gradient:

| Time (min) | % A | % B |
|---|---|---|
| 0 | 100 | 0 |
| 0.05 | 100 | 0 |
| 1.5 | 3 | 97 |
| 1.9 | 3 | 97 |
| 2 | 100 | 0 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1000 AMU

Scan Frequency: 5 Hertz

High pH Method B ("High pH B")

LC Conditions

Column: 30 mm×2.1 mm×1.7 μm, or 50 mm×2.1 mm, 1.7 μm CSH C18

Temperature: 40° C.

Injection volume: 0.3 μL

Mobile phases: A=10 mM ammonium bicarbonate in water solution and B=MeCN

Flow rate = 1 mL/min

Gradient:

| Time (min) | % A | % B |
|---|---|---|
| 0 | 70 | 30 |
| 0.10 | 70 | 30 |
| 2.00 | 0 | 100 |
| 3.00 | 0 | 100 |

The UV detection was a summed signal from the wavelength of 210 nm to 350 nm.

MS Conditions

MS: Waters QDA

Ionisation mode: Alternate-scan Positive and Negative Electrospray

Scan Range: 100 to 1000 AMU

Scan Frequency: 5 Hertz

High pH Method C ("High pH C")

LC Conditions

Column: XBRIDGE C18 (4.6×50 mm); 3.5 μm

Temperature: 40° C.

Injection volume: 2 μL

Mobile phases: A=5 mM ammonium bicarbonate in water solution and B=MeCN

Flow rate = 1 mL/min

Gradient:

| Time (min) | % A | % B |
|---|---|---|
| 0 | 80 | 20 |
| 0.5 | 80 | 20 |
| 4.0 | 0 | 100 |
| 5.0 | 0 | 100 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1250 AMU

Scan Frequency: 5 Hertz

High pH Method D ("High pH D")

LC Conditions

Column: 30 mm×2.1 mm×1.7 μm, or 50 mm×2.1 mm, 1.7 μm CSH C18

Temperature: 40° C.

Injection volume: 0.3 μL

Mobile phases: A=10 mM ammonium bicarbonate in water solution and B=MeCN

Flow rate = 1 mL/min

Gradient:

| Time (min) | % A | % B |
|---|---|---|
| 0 | 50 | 50 |
| 0.10 | 50 | 50 |
| 2.00 | 0 | 100 |
| 3.00 | 0 | 100 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1000 AMU

Scan Frequency: 5 Hertz

High pH Method E ("High pH E") 10-100 3 Min

LC Conditions

Column: XBRIDGE C18 (4.6×50 mm); 3.5 μm

Temperature: 40° C.

Injection volume: 2 μL

Mobile phases: A=5 mM ammonium bicarbonate in water solution and B=MeCN

Flow rate = 1 mL/min

Gradient:

| Time (min) | % A | % B |
|---|---|---|
| 0 | 90 | 10 |
| 0.5 | 90 | 10 |
| 4.0 | 0 | 100 |
| 5.0 | 0 | 100 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1250 AMU

Scan Frequency: 5 Hertz

High pH Method F ("High pH F")

LC Conditions

Column: XBRIDGE C18 (4.6×50 mm); 3.5 μm

Temperature: 40° C.

Injection volume: 2 μL

Mobile phases: A=5 mM ammonium bicarbonate in water solution and B=MeCN

Flow rate = 1 mL/min

Gradient:

| Time (min) | % A | % B |
|---|---|---|
| 0 | 80 | 20 |
| 0.1 | 80 | 20 |
| 2.5 | 0 | 100 |
| 3.9 | 0 | 100 |
| 4.9 | 80 | 20 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1250 AMU

Scan Frequency: 5 Hertz

High pH Method G ("High pH G")

LC Conditions

Column: XBRIDGE C8 (4.6×50 mm); 3.5 μm

Temperature: 40° C.

Injection volume: 3 μL

Mobile phases: A=10 mM ammonium bicarbonate in water solution and B=MeCN

Flow rate = 1.2 mL/min

Gradient:

| Time (min) | % A | % B |
|---|---|---|
| 0 | 90 | 10 |
| 4.0 | 5 | 95 |
| 5.0 | 5 | 95 |
| 5.5 | 90 | 10 |
| 6.0 | 90 | 10 |

The UV detection was a summed signal from wavelength of 210 nm to 350 nm.

MS Conditions

MS: Waters QDA

Ionisation mode: Alternate-scan Positive and Negative Electrospray

Scan Range: 100 to 1000 AMU

Scan Frequency: 5 Hertz

Mass Directed Auto-Preparative HPLC (MDAP)

MDAP was conducted using one of the following methods:

MDAP Formic

Column: 150 mm×30 mm, 5 μm or 75 mm×30 mm, 5 μm XSelect CSH C18

Mobile Phase A: 0.1% v/v solution of formic acid in Water

Mobile Phase B: 0.1% v/v solution of formic acid in MeCN.

Total Flow Rate: 40 mL/min

Temperature: Ambient

Injection Volume: varied

Instrument Name: Waters MDAP

UV Detection Parameters: 210-350 nm

Gradient: Gradients ranged from 100% A and 0% B to 0% A and 100% B across various lengths of time up to 32 min.

MDAP High pH

Column: 150 mm×30 mm, 5 μm or 100 mm×19 mm, 5 μm or 75 mm×30 mm, 5 μm XSelect CSH C18

Mobile Phase A: 10 mM ammonium bicarbonate in water adjusted to pH 10 with ammonia solution Mobile Phase B: MeCN Total Flow Rate: 40 mL/min Temperature: Ambient Injection Volume: varied Instrument Name: Waters MDAP UV Detection Parameters: 210-350 nm (1.2 nm Resolution; 1 Hz)

Gradient: Gradients ranged from 100% A and 0% B to 0% A and 100% B across various lengths of time up to 32 min.

Preparative HPLC

Prep HPLC was conducted using one of the following methods:

Prep HPLC (Formic)

Column: 100 mm×30 mm, 5 μm or 150 mm×19 mm, 5 μm or 150 mm×50 mm, 5 μm Sunfire

Mobile Phase A: Water (+0.1% formic acid)

Mobile Phase B: MeCN (+0.1% formic acid)

Total Flow Rate: 40 mL/min or 20 mL/min or 100 mL/min

Temperature: Ambient

Injection Volume: varied

Instrument Name: Agilent 1200

UV Detection Parameters: 210-350 nm (1.2 nm Resolution; 1 Hz)

Gradient: Gradients ranged from 80% A and 20% B to 0% A and 100% B across various lengths of time depend on column size.

Prep HPLC (High pH)

Column: 100 mm×30 mm, 5 μm or 150 mm×19 mm, 5 μm or 150 mm×50 mm, 5 μm XBridge

Mobile Phase A: 10 mM ammonium bicarbonate in water adjusted to pH 10 with ammonia (28-30% aq.).

Mobile Phase B: MeCN

Total Flow Rate: 40 mL/min or 20 mL/min or 100 mL/min

Temperature: Ambient

Injection Volume: varied

Instrument Name: Agilent 1200

UV Detection Parameters: 210-350 nm (1.2 nm Resolution; 1 Hz)

Gradient: Gradients ranged from 80% A and 20% B to 0% A and 100% B across various lengths of time depend on column size.

Prep HPLC (HCl)

Column: XSELECT C18 (19×250) mm 5 micron

Mobile Phase A: 0.1% HCL in MQ WATER

Mobile Phase B: MeCN

Total Flow Rate: 12 mL/min

Temperature: Ambient

Injection Volume: 300 μL

Gradient: Gradient ranged from 60% A and 40% B to 0% A and 100% B

Intermediates

Description 1 tert-Butyl 3,4-difluorobenzoate (D1)

To a stirred solution of 3,4-difluorobenzoic acid (2.00 g, 12.7 mmol) in tert-butanol (10 mL) was added DMAP (155 mg, 1.27 mmol) and di-tert-butyl dicarbonate (5.52 g, 25.3 mmol) then the mixture was heated at 60° C. for 24 h. The reaction mixture was diluted with EtOAc (50 mL) and washed sequentially with $NaHCO_3$ (sat. aq., 2×50 mL) and HCl (0.1 M aq., 50 mL). The organic layer was dried using a hydrophobic frit and evaporated in vacuo to give the required product (2.31 g, 85% yield) as a colourless liquid. LCMS (high pH A): Rt=1.34 min, MH+=does not ionise.

Description 2 tert-Butyl 3-fluoro-4-(4-(hydroxymethyl)piperidin-1-yl)benzoate (D2)

To a stirred solution of tert-butyl 3,4-difluorobenzoate (may be prepared as described in Description 1, 1.77 g, 8.26 mmol) in DMSO (16 mL) was added 4-piperidinemethanol (1.05 g, 9.09 mmol) and potassium carbonate (1.71 g, 12.4 mmol) then the mixture was heated at 100° C. for 18 h. The mixture was diluted with EtOAc (50 mL) and water (100 mL), then the phases were separated. The aqueous layer was back-extracted with EtOAc (50 mL), then the organic layers were combined, washed with brine (2×20 mL), dried using a hydrophobic frit and evaporated in vacuo to give the required product (2.60 g, 97% yield) as a yellow oil. LCMS (formic A): Rt=1.19 min, MH+=310.

Description 3 tert-Butyl 3-fluoro-4-(4-formylpiperidin-1-yl)benzoate (D3)

To a stirred solution of tert-butyl 3-fluoro-4-(4-(hydroxymethyl)piperidin-1-yl)benzoate (may be prepared as described in Description 2, 2.60 g, 8.40 mmol) in DCM (30 mL) was added DMP (3.56 g, 8.40 mmol) then the mixture was stirred at rt for 30 min. The reaction was quenched with $NaHCO_3$ (sat. aq.), then the phases were separated. The aqueous layer was back-extracted DCM (2×20 mL), then the combined organics were washed with sodium thiosulfate solution, dried using a hydrophobic frit and evaporated to dryness. The sample was purified by silica chromatography (80 g) using a 0-80% EtOAc/cyclohexane gradient over 12 column volumes. The appropriate fractions were combined and evaporated in vacuo to give the required product (2.55 g, 94% yield) as a pale brown solid. LCMS (formic A): Rt=1.31 min, MH+=308.

Description 4

3-((2-(Trimethylsilyl)ethoxy)methyl)dihydropyrimidine-2,4(1H,3H)-dione (D4)

Dihydropyrimidine-2,4(1H,3H)-dione (50 g×2, 438 mmol) was suspended in DMF (500 mL) and heated to 140° C. until the solution was clear. The reaction mixture was cooled to room temperature and added $Cs_2CO_3$ (214 g, 657 mmol) portion wise over a period of 30 min. The reaction mixture was further cooled to 10° C. and added (2-(chloromethoxy)ethyl)trimethylsilane (29.2 g, 175 mmol) dropwise and then reaction was allowed to stir at room temperature for 48 h. Reaction mixture was filtered under vacuum. Filtrate was diluted with water (2 L) and extracted with EtOAc (2×1 L). The combined organic layers were evaporated under reduced pressure to give crude compound. Crude was purified portion-wise, dissolved in DCM (200 mL) and purified using a 330 g silica column, eluting with 50-100% EtOAc:petroleum ether, and the desired fractions were combined and concentrated in vacuo to give the title compound as a colourless gummy solid (47 g, 187 mmol, 21% yield). GCMS: Rt=4.94 min, M-H$^-$=243.1

Description 5 tert-Butyl 4-(4-bromo-1H-indazol-1-yl)piperidine-1-carboxylate (D5)

4-Bromo-1H-indazole (38 g, 193 mmol) was dissolved in DMF (400 mL). $Cs_2CO_3$ (126 g, 386 mmol) and tert-butyl 4-((methylsulfonyl)oxy)piperidine-1-carboxylate (81 g, 289 mmol) were added, and the reaction mixture heated at 60° C. for 16 h. The reaction mixture was quenched by adding water (500 mL) and extracted with EtOAc (2×500 mL). The combined organic layers were washed with water (250 mL), dried over anhydrous sodium sulfate (3 g) and concentrated under reduced pressure. The crude material was purified on a 330 g silica cartridge using EtOAc in hexane as eluent to give the title compound as an orange gummy solid (29 g, 76 mmol, 40% yield). LCMS (formic A): Rt=1.33 min, M−$^t$Bu$^+$= 324.

Description 6 tert-Butyl 4-(4-(2,4-dioxo-3-((2-(trimethylsilyl)ethoxy)methyl)tetrahydropyrimidin-1(2H)-yl)-1H-indazol-1-yl)piperidine-1-carboxylate (D6)

To a solution of tert-butyl 4-(4-bromo-1H-indazol-1-yl)piperidine-1-carboxylate (may be prepared as described in Description 5; 1 g, 2.63 mmol), 3-((2-(trimethylsilyl)ethoxy)methy)dihydropyrimidine-2,4(1H,3H)-dione (may be prepared as described in Description 4; 0.643 g, 2.63 mmol), (1R,2R)—N1,N2-dimethylcyclohexane-1,2-diamine (0.224 g, 1.578 mmol) and $K_2CO_3$ (0.909 g, 6.57 mmol) in 1,4-dioxane (20 mL) was purged with nitrogen gas for 5 min. Copper(I) iodide (0.100 g, 0.526 mmol) was added and the mixture purged with nitrogen gas for 5 min. The reaction was stirred at 120° C. in a microwave for 3 h. This reaction procedure was repeated for a further 5× batches. The 6× reaction mixtures were filtered through Celite and the filtrate concentrated under reduced pressure. The material was washed with water (100 mL) and dried under vacuum. The material was dissolved in DCM (20 mL) and loaded onto a 120 g silica cartridge and purified using 40% EtOAc in hexane to give the title compound as an orange gummy liquid (4.7 g, 8.46 mmol, 54% yield). LCMS (formic A): Rt=1.31 min, $M-C_6H_{11}^+$=460.

Description 7

1-(1-(Piperidin-4-yl)-1H-indazol-4-yl)dihydropyrimidine-2,4(1H,3H)-dione 2,2,2-trifluoroacetate (D7)

Batch 1 tert-Buty 4-(4-(2,4-dioxo-3-((2-(trimethylsilyl)ethoxy)methyl)tetrahydropyrimidin-1(2H)-yl)-1H-indazol-1-yl)piperidine-1-carboxylate (may be prepared as described in Description 6; 12 g, 22.07 mmol) was dissolved in DCM (15.00 mL). TFA (15 mL) was added and the reaction mixture was stirred at room temperature for 16 h. The reaction mass was evaporated under reduced pressure. The material was dissolved in methanol (50 mL) and then slowly added to 4 M ammonia in MeOH (30 mL) and stirred for 60 min. A white precipitate formed which was concentrated to afford an off-white solid. The solid was dissolved in hot EtOAc (200 mL) and washed with water (100 mL), brine (100 mL), dried over sodium sulfate and concentrated under reduced pressure to afford a solid.

Batch 2 tert-Butyl 4-(4-(2,4-dioxo-3-((2-(trimethylsilyl)ethoxy)methyl)tetrahydropyrimidin-1(2H)-yl)-1H-indazol-1-yl)piperidine-1-carboxylate (may be prepared as described in Description 6; 13 g, 23.91 mmol) was dissolved in DCM (20.00 mL). TFA (20 mL) was added and the reaction mixture was stirred at room temperature for 16 h. The reaction mass was evaporated under reduced pressure. The material was dissolved in methanol (50 mL) and then slowly added to 4 M ammonia in methanol (30 mL) and stirred for 60 min. A white precipitate formed which was concentrated to afford an off-white solid. The solid was dissolved in hot EtOAc (200 mL) and washed with water (100 mL), brine (100 mL), dried over sodium sulfate and concentrated under reduced pressure to afford off a white solid. Batch 1 and Batch 2 were combined and stirred in methanol (150 mL) for 3 h. This was filtered, washed with water (2×100 mL) and dried to give the title compound (10.5 g, 24.52 mmol) as an off white solid. LCMS (formic A): Rt=0.28 min $MH^+$=314

Description 8

4-(4-((4-(4-(2,4-Dioxotetrahydropyrimidin-1(2H)-yl)-1H-indazol-1-yl)piperidin-1-yl)methyl)piperidin-1-yl)-3-fluorobenzoic Acid, Tris-Trifluoroacetic Acid Salt (D8)

To a stirred solution of 1-(1-(piperidin-4-yl)-1H-indazol-4-yl)dihydropyrimidine-2,4(1H,3H)-dione 2,2,2-trifluoroacetate (120 mg, 281 μmol, prepared as described in D7) and tert-butyl 3-fluoro-4-(4-formylpiperidin-1-yl)benzoate (may be prepared as described in Description 3; 104 mg, 337 μmol) in THF (2 mL) and DMF (2 mL) was added sodium triacetoxyborohydride (179 mg, 842 μmol) then the mixture was stirred at room temperature for 3 h. The mixture was diluted with EtOAc (25 mL), water (25 mL) and $NaHCO_3$ (sat. aq., 25 mL), then the phases were separated. The aqueous layer was back-extracted with EtOAc (25 mL), then the organic layers were combined, dried using a hydrophobic frit and evaporated in vacuo. The sample was purified by chromatography on silica (24 g) using a 0-100% EtOAc-cyclohexane gradient over 8 column volumes then a 0-25% ethanol-EtOAc gradient over 8 column volumes. The appropriate fractions were combined and evaporated in vacuo. The sample was directly dissolved in TFA (1.00 mL) then the mixture was stirred at room temperature for 15 min. The mixture was diluted with DCM (10 mL) and concentrated under a stream of nitrogen, diluted again with DCM (10 mL) and concentrated, then diluted with diethyl ether (10 mL) and sonicated resulting in solid precipitation. The suspension was concentrated under a stream of nitrogen then dried under vacuum to give the required product (108 mg, 58% yield over two steps) as a brown solid. LCMS (formic A): Rt=0.56 min, MH+=549.

Description 9

4-((1r,3r)-3-Amino-2,2,4,4-tetramethylcyclobutoxy)-2-chloro-3-methylbenzonitrile Hydrochloride (D9)

To an ice-cooled stirred solution of tert-butyl ((1r,3r)-3-hydroxy-2,2,4,4-tetramethylcyclobutyl)carbamate (1.58 g, 6.49 mmol) in DMF (40.0 mL) was added sodium hydride (307 mg, 60% Wt, 7.67 mmol) then the mixture stirred at 0° C. for 20 min. 2-Chloro-4-fluoro-3-methylbenzonitrile (1.00 g, 5.90 mmol) was added then the mixture stirred at room temperature for 1 h. The mixture was poured into water (200 mL), then extracted with EtOAc (3×100 mL). The organic layers were combined, washed with LiCl (5% aq., 200 mL), dried using a hydrophobic frit and evaporated in vacuo. The sample was dissolved in DCM (10 mL) then treated with HCl (4M in dioxane, 14.7 mL, 59.0 mmol) and the mixture stirred at room temperature for 16 h. The reaction mixture was concentrated in vacuo, then the resulting solid was triturated with diethyl ether (2×25 mL) and dried to give the required product (2.02 g, quantitative yield over two steps) as a white solid. LCMS (high pH A): Rt=1.26 min, MH+=293, 295.

Description 10 tert-Butyl ((1r,3r)-3-(4-cyano-3-ethoxyphenoxy)-2,2,4,4-tetramethylcyclobutyl)carbamate (D10)

To an ice-cooled stirred solution of tert-butyl ((1r,3r)-3-hydroxy-2,2,4,4-tetramethylcyclobutyl)carbamate (253 mg, 1.04 mmol) in DMF (8.0 mL) was added sodium hydride (49.1 mg, 60% Wt, 1.23 mmol) then the mixture stirred at 0° C. for 20 min. A solution of 2-ethoxy-4-fluorobenzonitrile (156 mg, 944 μmol, may be prepared as described in *Tetrahedron Letters,* 2010, 51, 3041-3044) in DMF (1.0 mL) was added then the mixture stirred at room temperature for 1.5 h. The mixture was poured into water (75 mL), then extracted with EtOAc (2×20 mL). The organic layers were combined, washed with LiCl (5% aq.) and brine, dried using a hydrophobic frit and evaporated in vacuo. The sample was dried under high vacuum to give the required product (370 mg, 80% yield, 79/a purity) as a colourless gum which was used directly in the next reaction. LCMS (formic A): Rt=1.41 min, [MH-Boc]+=289.

Description 11

4-((1r,3r)-3-Amino-2,2,4,4-tetramethylcyclobutoxy)-2-ethoxybenzonitrile Hydrochloride (D11)

A solution of tert-butyl ((1r,3r)-3-(4-cyano-3-ethoxyphenoxy)-2,2,4,4-tetramethylcyclobutyl)carbamate (may be prepared as described in Description 10, 370 mg, 79% Wt, 752 μmol) in DCM (2 mL) was treated with HCl (4M in dioxane, 1.5 mL, 6.0 mmol) and the mixture stirred at room temperature for 5 h. The reaction mixture was concentrated in vacuo, then the resulting solid was suspended in diethyl ether (25 mL), filtered under vacuum, washed with further diethyl ether (25 mL) and dried under vacuum to give the required product (222 mg, 84% yield) as a light green solid.

Description 12 tert-Butyl ((1r,3r)-3-(4-cyano-3-methoxy-2-methylphenoxy)-2,2,4,4-tetramethylcyclobutyl)carbamate (D12)

A stirred suspension of 2,4-difluoro-3-methylbenzonitrile (500 mg, 3.27 mmol) and potassium methoxide (252 mg, 3.59 mmol) in 1,4-dioxane (4.5 mL) was heated to 90° C. for 20 h. The mixture was diluted with water and extracted with EtOAc (2×20 mL). The organic layers were combined, washed with brine (10 mL), dried using a hydrophobic frit and evaporated in vacuo. The sample was purified by silica chromatography (24 g) using a 0-25% EtOAc/cyclohexane gradient, then the appropriate fractions were combined and evaporated in vacuo to give crude 4-fluoro-2-methoxy-3-methylbenzonitrile (460 mg). To an ice-cooled stirred solution of tert-butyl ((1r,3r)-3-hydroxy-2,2,4,4-tetramethylcyclobutyl)carbamate (746 mg, 3.06 mmol) in DMF (12 mL) was added sodium hydride, 60% in mineral oil (145 mg, 60% Wt, 3.62 mmol) then the mixture stirred at 0° C. for 20 min. The crude 4-fluoro-2-methoxy-3-methylbenzonitrile (460 mg, 2.79 mmol) in DMF (1.5 mL) was added then the mixture stirred at room temperature for 2 h. The reaction mixture was diluted with water (100 mL) and extracted with EtOAc (2×25 mL). The organic layers were combined, washed sequentially with LiCl (5% aq.) and brine, dried using a hydrophobic frit and evaporated in vacuo. The sample was purified by silica chromatography (24 g) using a 0-20% EtOAc/cyclohexane gradient. The appropriate fractions were combined and evaporated in vacuo to give the required product (338 mg, 24% yield over two steps) as a colourless gum. LCMS (high pH A): Rt=1.44 min, MH−=387.

Description 13

4-((1r,3r)-3-Amino-2,2,4,4-tetramethylcyclobutoxy)-2-methoxy-3-methylbenzonitrile hydrochloride (D13)

A solution of tert-butyl ((1r,3r)-3-(4-cyano-3-methoxy-2-methylphenoxy)-2,2,4,4-tetramethylcyclobutyl)carbamate (may be prepared as described in Description 12, 338 mg, 783 μmol) in DCM (2 mL) was treated with HCl (4M in dioxane, 1.5 mL, 6.0 mmol) then the mixture was stirred at room temperature for 5 h. The reaction mixture was concentrated in vacuo, then the resulting solid was suspended in diethyl ether (25 mL), filtered under vacuum, washed with further diethyl ether (25 mL) and dried under air then vacuum to give the required product (211 mg, 79% yield) as a light green solid. LCMS (high pH A): Rt=1.14 min, MH+=289.

Description 14

5-Fluoro-2-methylquinoline-8-carbonitrile (D14)

Potassium hexacyanoferrate (III) (933 mg, 2.83 mmol), sodium carbonate (150 mg, 1.42 mmol) and palladium diacetate (15.9 mg, 70.8 μmol) were sealed into a vial and placed under an atmosphere of nitrogen. A solution of 8-bromo-5-fluoro-2-methylquinoline (340 mg, 1.42 mmol, may be prepared as described in *J. Med. Chem.* 2017, 60, 1343-1361) in DMAc (12 mL) was added, then the reaction was heated to 120° C. for 4 h. The reaction mixture was diluted with EtOAc, water and $NaHCO_3$ (sat. aq.). The aqueous layer was back-extracted with EtOAc, and the combined organic phases were washed with brine, dried using a hydrophobic frit and evaporated in vacuo. The sample was purified by silica chromatography (24 g) using a 0-35% EtOAc/cyclohexane gradient. The appropriate fractions were combined and evaporated in vacuo to give the required product (117 mg, 44% yield) as a white solid. LCMS (high pH A): Rt=0.95 min, MH+=187.

Description 15 tert-Butyl ((1r,3r)-3-((8-cyano-2-methylquinolin-5-yl)oxy)-2,2,4,4-tetramethylcyclobutyl)carbamate (D15)

To an ice-cooled stirred solution of tert-butyl ((1r,3r)-3-hydroxy-2,2,4,4-tetramethylcyclobutyl)carbamate (168 mg, 691 μmol) in DMF (4 mL) was added sodium hydride, (60% in mineral oil, 32.7 mg, 817 μmol) then the mixture stirred at 0° C. for 20 min. A solution of 5-fluoro-2-methylquinoline-8-carbonitrile (may be prepared as described in Description 14; 117 mg, 628 μmol) in DMF (1 mL) was added then the mixture was stirred at rt for 2 h. The reaction mixture was diluted with water (50 mL) and extracted with EtOAc (2×15 mL). The organic layers were combined, were washed with LiCl (5% aq.), dried using a hydrophobic frit and evaporated in vacuo. The sample was purified by silica chromatography (12 g) using a 0-25% EtOAc/cyclohexane gradient. The appropriate fractions were combined and evaporated in vacuo to give the required product (165 mg, 61% yield) as a white solid. LCMS (high pH A): Rt=1.41 min, MH+=410.

Description 15

5-((1r,3r)-3-Amino-2,2,4,4-tetramethylcyclobutoxy)-2-methylquinoline-8-carbonitrile Hydrochloride (D16)

A solution of tert-butyl ((1r,3r)-3-((8-cyano-2-methylquinolin-5-yl)oxy)-2,2,4,4-tetramethylcyclobutyl)carbamate (may be prepared as described in Description 15, 165 mg, 403 μmol) in 1,4-dioxane (1 mL) and DCM (1 mL) was treated with HCl (4M in dioxane, 1.5 mL, 6.0 mmol) and the mixture stirred at room temperature for 20 h. The reaction mixture was concentrated in vacuo, then the resulting solid was diluted with minimal diethyl ether, causing precipitation. The solid was dried under vacuum to give the required product (174 mg, quantitative yield) as a yellow solid. LCMS (high pH A): Rt=1.09 min, MH+=310.

Description 17

3-Allyl-4-fluoro-2-hydroxybenzonitrile (D17)

A solution of 2-(allyloxy)-4-fluorobenzonitrile (4.23 g, 23.9 mmol, prepared as described in WO2014159959A1) in 1,2-dichlorobenzene (24 mL) was heated to 180° C. for 24 h. The mixture was concentrated under vacuum, then dissolved in DCM and adsorbed onto Florisil. The sample was purified by silica chromatography (120 g) using a 0-30% EtOAc/cyclohexane gradient. The appropriate fractions were combined and evaporated in vacuo to give the required product (2.64 g, 54% yield, 87% purity) as a yellow solid which was used directly in the next reactions. LCMS (formic A): Rt=0.97 min, MH−=176.

Description 18

4-Fluoro-2-hydroxy-3-(3-hydroxypropyl)benzonitrile (D18)

A solution of 3-allyl-4-fluoro-2-hydroxybenzonitrile (may be prepared as described in Description 17, 778 mg, 87% weight, 3.82 mmol) in THF (40 mL) was cooled to 0° C. in an ice bath and borane dimethyl sulfide complex (2.0 M in THF, 2.01 mL, 4.01 mmol) was added. The mixture was stirred at 0° C. and gradually allowed to warm to room temperature over 3 h. The reaction was cooled back to 0° C. and a mixture of hydrogen peroxide (2.0 mL, 30% aq., 20 mmol) and NaOH (2M aq., 3.0 mL, 6.0 mmol) was added and the reaction was stirred at 0° C. for 1 h. The reaction was quenched with sodium thiosulfate (sat. aq., 20 mL). The reaction was acidified to pH ~2 with concentrated HCl and extracted with EtOAc (50 mL, then 2×20 mL). The organic layers were combined, washed twice with brine, dried over magnesium sulfate, filtered and evaporated in vacuo to give the required product (850 mg, 80% yield, 70% purity) as a cloudy yellow oil that was used directly in the next reaction. LCMS (formic A): Rt=0.76 min, MH−=194.2.

Description 19

5-Fluorochromane-8-carbonitrile (D19)

4-Fluoro-2-hydroxy-3-(3-hydroxypropyl)benzonitrile (may be prepared as described in Description 18, 850 mg, 70% weight, 3.05 mmol) and triphenylphosphine (879 mg, 3.35 mmol) were dissolved in THF (20 mL) and cooled to 0° C. DIAD (652 µL, 3.35 mmol) was added dropwise and the reaction was stirred at 0° C. for 2 h. The reaction mixture was concentrated under vacuum, then the sample was purified by silica chromatography (80 g) using a 0-20% EtOAc/cyclohexane gradient. The appropriate fractions were combined and evaporated in vacuo to give the required product (322 mg, 1.8 mmol, 59% yield) as a colourless oil. LCMS (formic A): Rt=0.98 min, MH+=does not ionise.

Description 20 tert-Butyl ((1r,3r)-3-((8-cyanochroman-5-yl)oxy)-2,2,4,4-tetramethylcyclobutyl)carbamate (D20)

To an ice-cooled stirred solution of tert-butyl ((1r,3r)-3-hydroxy-2,2,4,4-tetramethylcyclobutyl)carbamate (486 mg, 2.00 mmol) in DMF (16 mL) was added sodium hydride, (94.5 mg, 60% weight, 2.36 mmol) then the mixture stirred at 0° C. for 20 min. A solution of 5-fluorochromane-8-carbonitrile (322 mg, 1.82 mmol) in DMF (2 mL) was added then the mixture stirred at room temperature for 1.5 h. The mixture was poured into water (100 mL) then extracted with EtOAc (2×50 mL). The organic layers were combined, washed with LiCl (5% aq.) and brine, dried using a hydrophobic frit and evaporated in vacuo. The crude was dried under high vacuum to give the required (794 mg, 1.7 mmol, 93% yield, 85% Purity) as an off-white solid which was used directly in the next reaction. LCMS (high pH A): Rt=1.41 min, MH+=401.

Description 21

5-((1r,3r)-3-Amino-2,2,4,4-tetramethylcyclobutoxy)chromane-8-carbonitrile Hydrochloride (D21)

A solution of tert-butyl ((1r,3r)-3-((8-cyanochroman-5-yl)oxy)-2,2,4,4-tetramethylcyclobutyl)carbamate (may be prepared as described in Description 20, 794 mg, 85% weight, 1.69 mmol) in DCM (5 mL) was treated with HCl (4M in dioxane, 4.21 mL, 16.9 mmol) and the mixture stirred at room temperature for 6 h. The reaction mixture was concentrated in vacuo, then the resulting solid was suspended in diethyl ether (10 mL), filtered under vacuum, washed with further diethyl ether and dried under vacuum to give the required product (566 mg, 89% yield, 89% Purity) as an off-white solid. LCMS (high pH A): Rt=1.10 min, MH+=301.

Description 22

4-Fluoro-2-hydroxy-3-(2-hydroxyethyl)benzonitrile (D22)

A solution of 3-allyl-4-fluoro-2-hydroxybenzonitrile (1.0 g, 5.6 mmol) in methanol (50 mL) and was cooled to −60° C. and treated with ozone gas (generated using Fischer OZ502 ozone generator with compressed air supply) for 50 min. Sodium borohydride (0.32 g, 8.5 mmol) was added, the reaction was allowed to warm to room temperature and stirred for 1 h. The reaction mixture was quenched with HCl (2M aq.), concentrated in vacuo and partitioned between water (20 mL) and EtOAc (20 mL). The aqueous layer was back-extracted with EtOAc (2×20 mL), then the organic layers were combined, washed with brine, dried using a hydrophobic frit and evaporated in vacuo to give the required product (762 mg, 52% yield, 70% Purity) as a yellow gum which was used directly in the next reaction. LCMS (formic A): Rt=0.72 min, MH−=180.

Description 23

4-Fluoro-2,3-dihydrobenzofuran-7-carbonitrile (D23)

4-Fluoro-2-hydroxy-3-(2-hydroxyethyl)benzonitrile (may be prepared as described in Description 22, 762 mg, 70% weight, 2.94 mmol) and triphenylphosphine (849 mg, 3.24 mmol) were dissolved in THF (20 mL) and cooled to 0° C. DIAD (630 µL, 3.24 mmol) was added dropwise and the reaction was stirred at room temperature for 3 h. The reaction mixture was concentrated under vacuum. The sample was purified by silica chromatography (40 g) using a 0-25% EtOAc/cyclohexane gradient. The appropriate fractions were combined and evaporated to give the required product (235 mg, 48% yield) as a white solid. LCMS (formic A): Rt=0.90 min, MH+=does not ionise.

Description 24 tert-Butyl ((1r,3r)-3-((7-cyano-2,3-dihydrobenzofuran-4-yl)oxy)-2,2,4,4-tetramethylcyclobutyl)carbamate (D24)

To an ice-cooled stirred solution of tert-butyl ((1r,3r)-3-hydroxy-2,2,4,4-tetramethylcyclobutyl)carbamate (386 mg, 1.58 mmol) in DMF (12.8 mL) was added sodium hydride (74.9 mg, 60% weight, 1.87 mmol) then the mixture stirred at 0° C. for 20 min. A solution of 4-fluoro-2,3-dihydrobenzofuran-7-carbonitrile (may be prepared as described in Description 23; 235 mg, 1.44 mmol) in DMF (1.60 mL) was added then the mixture stirred at room temperature for 1.5 h. The mixture was poured into water (100 mL), then extracted with EtOAc (2×50 mL). The organic layers were combined, washed with LiCl (5% aq.) and brine, dried using a hydrophobic frit and evaporated in vacuo. The crude was dried under high vacuum give the required product (565 mg, 87% yield, 86% purity) as a white solid that was used directly in the next reaction. LCMS (high pH A): Rt=1.38 min, MH+=387.

Description 25

4-((1r,3r)-3-Amino-2,2,4,4-tetramethylcyclobutoxy)-2,3-dihydrobenzofuran-7-carbonitrile hydrochloride (D25)

A solution of tert-butyl ((1r,3r)-3-((7-cyano-2,3-dihydrobenzofuran-4-yl)oxy)-2,2,4,4-tetramethylcyclobutyl)carbamate (may be prepared as described in Description 24, 565 mg, 86% weight, 1.26 mmol) in DCM (3 mL) was treated with HCl (4M in dioxane, 1.57 mL, 6.29 mmol) and the mixture stirred at room temperature for 6 h. The reaction mixture was concentrated in vacuo, then the resulting solid was suspended in diethyl ether (25 mL), filtered under vacuum, washed with diethyl ether (25 mL) and dried under air and vacuum to give the required product (378 mg, 87% yield) as an off-white solid. LCMS (high pH A): Rt=1.07 min, MH+=287.

Description 26 tert-Butyl (S)-3-(4-bromo-1H-indazol-1-yl)pyrrolidine-1-carboxylate (D26)

tert-Butyl (R)-3-((methylsulfonyl)oxy)pyrrolidine-1-carboxylate (1.35 g, 5.08 mmol), 4-bromo-1H-indazole (1.00 g, 5.08 mmol) and potassium carbonate (1.40 g, 10.2 mmol) were dissolved in DMF (20 mL) and heated to 100° C. for 36 h. The mixture was diluted with EtOAc and washed with $NH_4Cl$ (1M aq.), then the organic layer was dried over sodium sulfate, filtered and concentrated in vacuo. The sample was purified by silica chromatography (50 g) using a 0-50% EtOAc/cyclohexane gradient, then the appropriate fractions were combined and evaporated in vacuo to give the required product (528 mg, 27% yield) as a colourless oil. LCMS (high pH F) Rt=3.98 min, [M-tBu]+=310/312.

Description 27 tert-Butyl (S)-3-(4-(2,4-dioxo-3-((2-(trimethylsilyl)ethoxy)methyl)tetrahydropyrimidin-1(2H)-yl)-1H-indazol-1-yl)pyrrolidine-1-carboxylate (D27)

A vial was charged with tert-butyl (5)-3-(4-bromo-1H-indazol-1-yl)pyrrolidine-1-carboxylate (may be prepared as described in Description 26, 528 mg, 1.4 mmol), 3-((2-(trimethylsilyl)ethoxy)methyl)dihydropyrimidine-2,4(1H,3H)-dione (may be prepared as described in D4, 405 mg, 1.66 mmol), potassium carbonate (398 mg, 2.88 mmol), copper(I) iodide (54.9 mg, 288 μmol), 1,4-dioxane (12 mL) and (1S,2S)—N1,N2-dimethylcyclohexane-1,2-diamine (90.9 μL, 577 μmol). The reaction mixture was sparged with nitrogen, then the vial was sealed and stirred at 140° C. for 18 h. The reaction mixture was cooled to room temperature, then diluted with EtOAc and filtered through Celite. The filtrate was diluted with water, then the phases were separated. The organic layer was washed with water and brine, dried over sodium sulfate and evaporated in vacuo. The sample was purified by silica chromatography (25 g) using a 0-50% EtOAc/cyclohexane gradient, then the appropriate fractions were combined and evaporated in vacuo to give the required product (540 mg, 64% yield) as a white solid. LCMS (formic B): Rt=1.49 min, MH+=530.

Description 28

(S)-1-(1-(Pyrrolidin-3-yl)-1H-indazol-4-yl)dihydropyrimidine-2,4(1H,3H)-dione (D28)

A solution of tert-butyl (5)-3-(4-(2,4-dioxo-3-((2-(trimethylsilyl)ethoxy)methyl)tetrahydropyrimidin-1(2H)-yl)-1H-indazol-1-yl)pyrrolidine-1-carboxylate (may be prepared as described in Description 27, 540 mg, 1.02 mmol) in DCM (10 mL) was cooled to 0° C. then treated with TFA (1.57 mL, 20.4 mmol) and the mixture stirred at room temperature for 2 h. The reaction mixture was concentrated in vacuo, dissolved in methanol (1 mL) then ammonia (7M in methanol, 8.74 mL, 61.2 mmol) was added dropwise. The reaction mixture was concentrated in vacuo, then purified by prep HPLC (high pH). The appropriate fractions were combined and evaporated in vacuo to give the required product (266 mg, 83% yield). LCMS (formic B): Rt=0.55 min, MH+=300.

Description 29

Methyl 3-fluoro-4-(4-(hydroxymethyl)piperidin-1-yl)benzoate (D29)

A mixture of methyl 3,4-difluorobenzoate (2.80 g, 16.3 mmol), piperidin-4-ylmethanol (2.06 g, 17.9 mmol), and potassium carbonate (2.70 g, 19.5 mmol) in DMAc (40 mL) was stirred at 100° C. for 17 h. The reaction was diluted with EtOAc and water, the phases were separated, and the aqueous layer was back-extracted with EtOAc three times. The combined organic layers were dried over anhydrous sodium sulfate and evaporated in vacuo. The sample was purified by silica chromatography (120 g) using a 0-100% EtOAc/cyclohexane gradient, then the appropriate fractions were combined and evaporated in vacuo to give the required product (4.11 g, 93% yield) as a white solid. LCMS (high pH A): Rt=0.96 min, $MH^+$=268.

Description 30

3-Fluoro-4-(4-(hydroxymethyl)piperidin-1-yl)benzoic Acid (D30)

To a stirred solution of methyl 3-fluoro-4-(4-(hydroxymethyl)piperidin-1-yl)benzoate (may be prepared as described in Description 29, 540 mg, 2.02 mmol) in methanol (10 mL) was added NaOH (2M aq., 3.03 mL, 6.06 mmol) then the mixture stirred at room temperature for 16 h. The mixture was diluted with EtOAc (50 mL) and HCl (2M aq., 50 mL), then the phases were separated. The aqueous layer was saturated with solid NaCl and extracted with EtOAc (5×50 mL), then the organic layers were combined, dried using a hydrophobic frit and evaporated in vacuo to give the required product (400 mg, 78% yield) as a white solid. LCMS (high pH A): Rt=0.40 min, $MH^+$=254.

Description 31 tert-Butyl ((1r,3r)-3-(3-chloro-4-cyanophenoxy)-2,2,4,4-tetramethylcyclobutyl)carbamate (D31)

To a stirred solution of tert-butyl ((1r,3r)-3-hydroxy-2,2,4,4-tetramethylcyclobutyl)carbamate (1 g, 4.11 mmol) in DMF (100 mL), cooled in an ice-water bath, was added 60% NaH in mineral oil (0.214 g, 5.34 mmol) and the reaction mixture was stirred for 20 min, then 2-chloro-4-fluorobenzonitrile (0.703 g, 4.52 mmol) was added in small portions (effervescence) and the mixture stirred for 2h, allowing it to warm to room temperature. The mixture was quenched with water (100 ml) and the resulting suspension stirred for 30 min, then the product collected by filtration and washed with water to give a pale yellow solid. The crude was dissolved in DCM and loaded onto a 40 g silica column, then eluted with 0-50% EtOAc/cyclohexane and product-containing fractions evaporated in vacuo to give the title compound as a colourless gum (1.58 g, 4.17 mmol, quantitative yield). LCMS (formic A): Rt=1.49 min, M-$^t$$Bu^+$=323, 325.

Description 32

4-((1r,3r)-3-Amino-2,2,4,4-tetramethylcyclobutoxy)-2-chlorobenzonitrile (D32)

TFA (3 mL, 38.9 mmol) was added to a solution of tertbutyl ((1r,3r)-3-(3-chloro-4-cyanophenoxy)-2,2,4,4-tetramethylcyclobutyl)carbamate (may be prepared as described in Description 31; 1.58 g, 4.17 mmol) in DCM (10 mL) and the mixture was stirred at room temperature for 2 h, then evaporated in vacuo. The gummy residue was stirred in water (20 mL) and HCl (1M aq., 20 mL), giving a dense suspension. The mixture was basified with solid potassium carbonate and extracted with DCM (3×20 mL), the organics dried and evaporated in vacuo to give the title compound as a colourless solid (1.05 g, 3.77 mmol, 90% yield). The sample was used in the next reaction without further purification. LCMS (formic A): Rt=0.64 min, $MH^+$=279, 281.

Description 33

N-((1r,3r)-3-(3-Chloro-4-cyanophenoxy)-2,2,4,4-tetramethylcyclobutyl)-3-fluoro-4-(4-(hydroxymethyl)piperidin-1-yl)benzamide (D33)

To a solution of 3-fluoro-4-(4-(hydroxymethyl)piperidin-1-yl)benzoic acid (may be prepared as described in Description 30, 1.77 g, 6.98 mmol), HATU (3.62 g, 9.52 mmol) and DIPEA (4.42 mL, 25.4 mmol) in DMF (20 mL) was added a solution of 4-((1r,3r)-3-amino-2,2,4,4-tetramethylcyclobutoxy)-2-chlorobenzonitrile hydrochloride (may be prepared as described in D32, 2.00 g, 6.34 mmol) in DMF (10 mL) then the mixture was stirred at room temperature for 3.5 h. The reaction mixture was diluted with EtOAc and then treated with $NH_4Cl$ (sat. aq.) then the phases were separated. The organic phase was washed with further $NH_4Cl$, then the aqueous phases were combined and back-extracted with EtOAc. The organic layers were combined, dried over $Na_2SO_4$, filtered and evaporated in vacuo. The resulting sample was cooled to 0° C. then suspended in DCM. The resulting precipitate was separated by vacuum filtration to give the required product (2.25 g, 66% yield) as a white solid. LCMS (high pH B) Rt=2.28 min, MH+=514

Description 34

N-((1r,3r)-3-(3-Chloro-4-cyanophenoxy)-2,2,4,4-tetramethylcyclobutyl)-3-fluoro-4-(4-formylpiperidin-1-yl)benzamide (D34)

DMP (825 mg, 1.95 mmol) was added to a stirred solution of N-((1r,3r)-3-(3-chloro-4-cyanophenoxy)-2,2,4,4-tetramethylcyclobutyl)-3-fluoro-4-(4-(hydroxymethyl)piperidin-1-yl)benzamide (may be prepared as described in Description 33, 500 mg, 973 μmol) in DCM (10 mL) then the mixture was stirred at room temperature for 1.5 h. The reaction was quenched with $Na_2CO_3$ (10% aq.) and diluted with DCM, then the resulting emulsion was filtered. The filtrate was collected, and the phases were separated. The aqueous layer was back-extracted twice with DCM, then the organic layers were combined, dried over sodium sulfate, filtered and evaporated in vacuo. The sample was purified by silica chromatography (25 g) using a 0-100% EtOAc/cyclohexane gradient, then the appropriate fractions were combined and evaporated in vacuo to give the required product (343 mg, 65% yield) as yellow solid. LCMS (high pH C) Rt: 2.50 min, MH+=513.

Description 35 tert-Butyl (3R,4S)-4-(4-bromo-1H-indazol-1-yl)-3-fluoropiperidine-1-carboxylate (D35)

tert-Butyl (3R,4R)-3-fluoro-4-hydroxypiperidine-1-carboxylate (851 mg, 3.88 mmol) and 4-bromo-1H-indazole (0.425 g, 2.16 mmol) was placed in a vial, then sealed, evacuated and purged with nitrogen three times. Toluene (12.25 mL) was added followed by addition of CMBP (1.13 mL, 4.31 mmol). The mixture was degassed with nitrogen for 5 min, then heated to 95° C. for 15 h. This procedure was duplicated in a second vial. The mixtures were cooled to room temperature, then combined and evaporated in vacuo. The sample was purified by silica chromatography (120 g) using a 0-25% EtOAc/cyclohexane gradient. The appropriate fractions were combined and evaporated in vacuo to give the required product (878 mg, 48% yield) as an orange foam. LCMS (high pH B): Rt=2.26 min, [M-tBu]+=342/344.

Description 36 tert-Butyl (3R,4S)-4-(4-(2,4-dioxo-3-((2-(trimethylsilyl)ethoxy)methyl)tetrahydropyrimidin-1(2H)-yl)-1H-indazol-1-yl)-3-fluoropiperidine-1-carboxylate (D36)

A vial was charged with copper(I) iodide (39.1 mg, 205 μmol), 3-((2-(trimethylsilyl)ethoxy)methyl)dihydropyrimidine-2,4(1H,3H)-dione (may be prepared as described in D4; 289 mg, 1.18 mmol) and potassium carbonate (284 mg, 2.05 mmol), then a solution of tert-butyl (3R,4S)-4-(4-bromo-1H-indazol-1-yl)-3-fluoropiperidine-1-carboxylate (may be prepared as described in Description 35, 0.435 g, 1.03 mmol) in 1,4-diaxane (7.5 mL) was added followed by addition of trans-N,N'-dimethylcyclohexane-1,2-diamine (65.0 μL, 412 μmol). The reaction mixture was sparged with nitrogen, then the mixture was stirred at 140° C. for 14 h. This procedure was duplicated in a second vial. The two reaction mixtures were cooled to room temperature and diluted with EtOAc, then combined and filtered through Celite. The filtrate was diluted with water then the phases were separated. The aqueous layer was back-extracted with EtOAc, then the organic layers were combined, washed twice with water, dried over sodium sulfate and evaporated in vacuo. The sample was purified by silica chromatography (80 g) using a 0-100% EtOAc/cyclohexane gradient, then the appropriate fractions were combined and evaporated in vacuo to give the required product (585 mg, 48% yield) as a white solid. LCMS (high pH B) Rt=2.32 min, M+Na=584.

Description 37

1-(1-((3R,4S)-3-Fluoropiperidin-4-yl)-1H-indazol-4-yl)dihydropyrimidine-2,4(1H,3H)-dione (D37)

To a solution of tert-butyl (3R,4S)-4-(4-(2,4-dioxo-3-((2-(trimethylsilyl)ethoxy)methyl)tetrahydropyrimidin-1(2H)-yl)-1H-indazol-1-yl)-3-fluoropiperidine-1-carboxylate (may be prepared as described in Description 36, 0.580 g, 1.03 mmol) in DCM (8 mL) at 0° C. was added TFA (1.57 mL, 20.7 mmol) dropwise, then the mixture was stirred at room temperature for 1.5 h. The reaction mixture was concentrated in vacuo, then the sample was dissolved in methanol (1 mL) followed by dropwise addition of ammonia (7M in methanol, 8.85 mL, 62.0 mmol) then the mixture was stirred at room temperature for 75 min. The reaction mixture was concentrated in vacuo, then the sample was purified by prep HPLC (high pH) to give the required product (275 mg, 77% yield) as a white solid. LCMS (high pH B) Rt=1.26 min, MH+=332.

Description 38

4-(4-(Hydroxymethyl)piperidin-1-yl)benzoic Acid (D38)

To a suspension of methyl 4-(4-(hydroxymethyl)piperidin-1-yl)benzoate (1.65 g, 6.62 mmol) in methanol (20 mL) was added NaOH (2M aq., 6.62 mL, 13.2 mmol) then the mixture was stirred at room temperature for 22 h, then at 50° C. for 5 h. The reaction mixture was concentrated in vacuo, diluted with EtOAc and water (100 mL) and the mixture acidified with HCl (2M aq.). A precipitate formed that was separated by filtration and dried under air then high vacuum to give the required product (1.45 g, 92% yield) as a white solid. LCMS (formic A): Rt=0.56 min, MH+=236.

Description 39 tert-Butyl ((1r,3r)-3-(4-cyano-3-methoxyphenoxy)-2,2,4,4-tetramethylcyclobutyl)carbamate (D39)

To a stirred solution of 4-fluoro-2-methoxybenzonitrile (30.0 g, 198 mmol) in THF (300 mL) was added NaH (60% Wt, 15.9 g, 397 mmol) at 0° C., then tert-butyl ((1r,3r)-3-hydroxy-2,2,4,4-tetramethylcyclobutyl)carbamate (58.0 g, 238 mmol) was added. The mixture was allowed to warm to room temperature and stirred for 12 h. The reaction mixture was diluted with ice cold water (300 mL) and was extracted with EtOAc (2×400 mL). The organic layers were combined, washed with brine (500 mL), dried over sodium sulfate, filtered and evaporated in vacuo. The sample was purified by silica chromatography using a 0-20% EtOAc/petroleum ether gradient. The appropriate fractions were combined and evaporated in vacuo to give the required product (65 g, 80% yield) as a white solid. LCMS (formic A): Rt=1.33 min, MH+=375.

Description 40

4-((1r,3r)-3-Amino-2,2,4,4-tetramethylcyclobutoxy)-2-methoxybenzonitrile Hydrochloride (D40)

To a stirred solution of tert-butyl ((1r,3r)-3-(4-cyano-3-methoxyphenoxy)-2,2,4,4-tetramethylcyclobutyl)carbamate (may be prepared as described in Description 39, 40.0 g, 107 mmol) in DCM (400 mL) at 0° C. was added HC (4M in dioxane, 107 mL, 427 mmol). then the reaction mixture was stirred at room temperature for 4 h. The reaction mixture was evaporated in vacuo, then triturated with petroleum ether to give the required product (29.0 g, 87% yield) as a white solid. LCMS (formic A): Rt=0.61 min, MH+=275.

Description 41

N-((1r,3r)-3-(4-Cyano-3-methoxyphenoxy)-2,2,4,4-tetramethylcyclobutyl)-4-(4-(hydroxymethyl)piperidin-1-yl)benzamide (D41)

To a stirred solution of 4-((1r,3r)-3-amino-2,2,4,4-tetramethylcyclobutoxy)-2-methoxybenzonitrile hydrochloride (may be prepared as described in Description 40, 300 mg, 965 μmol), 4-(4-(hydroxymethyl)piperidin-1-yl)benzoic acid (may be prepared as described in Description 38, 238 mg, 1.01 mmol) and DIPEA (841 μL, 4.83 mmol) in DCM (5.00 mL) was added HATU (385 mg, 1.01 mmol) then the mixture was stirred at room temperature for 15 min. The mixture was concentrated in vacuo, then the sample was purified by silica chromatography (40 g) using a 0-100% EtOAc/cyclohexane gradient. The appropriate fractions were combined and evaporated in vacuo to give the required product (318 mg, 67% yield) as a white solid. LCMS (high pH A): Rt=1.20 min, MH+=492.

Description 42

N-((1r,3r)-3-(4-Cyano-3-methoxyphenoxy)-2,2,4,4-tetramethylcyclobutyl)-4-(4-formylpiperidin-1-yl)benzamide (D42)

To a stirred solution of N-((1r,3r)-3-(4-cyano-3-methoxyphenoxy)-2,2,4,4-tetramethylcyclobutyl)-4-(4-(hydroxymethyl)piperidin-1-yl)benzamide (may be prepared as described in Description 41, 315 mg, 641 μmol) in DCM (5 mL) was added DMP (326 mg, 769 μmol) then the mixture was stirred at room temperature for 15 min. The reaction mixture was concentrated in vacuo, then the sample was purified by silica chromatography (40 g) using a 0-100% EtOAc/cyclohexane gradient. The appropriate fractions were combined and evaporated in vacuo to give the required product (286 mg, 91% yield) as a brown gum. LCMS (formic A): Rt=1.25 min, MH+=490.

Description 43

N-((1r,3r)-3-(4-Cyano-3-methoxyphenoxy)-2,2,4,4-tetramethylcyclobutyl)-3-fluoro-4-(4-(hydroxymethyl)piperidin-1-yl)benzamide (D43)

To a stirred solution of 3-fluoro-4-(4-(hydroxymethyl)piperidin-1-yl)benzoic acid (may be prepared as described in Description 30, 1.85 g, 7.29 mmol), HATU (4.16 g, 10.9 mmol) and DIPEA (3.77 g, 5.08 mL, 29.2 mmol) in DMF (40 mL) was added 4-((1r,3r)-3-amino-2,2,4,4-tetramethylcyclobutoxy)-2-methoxybenzonitrile hydrochloride (may be prepared as described in Description 40, 2.00 g, 7.29 mmol), then the mixture was stirred at room temperature for 3 h. The reaction mixture was diluted with EtOAc and ammonium chloride (1M aq.), then the phases were separated. The organic layer was dried using sodium sulfate, filtered and concentrated in vacuo. The sample was purified by silica chromatography (80 g) using a 0-80% EtOAc/cyclohexane gradient. The appropriate fractions were combined and evaporated in vacuo to give the required product (3.02 g, 76% yield) as a white solid. LCMS (high pH C): Rt=2.45 min, MH+=510.

Description 44

N-((1r,3r)-3-(4-Cyano-3-methoxyphenoxy)-2,2,4,4-tetramethylcyclobutyl)-3-fluoro-4-(4-formylpiperidin-1-yl)benzamide (D44)

To a solution of N-((1r,3r)-3-(4-cyano-3-methoxyphenoxy)-2,2,4,4-tetramethylcyclobutyl)-3-fluoro-4-(4-(hydroxymethyl)piperidin-1-yl)benzamide (may be prepared as described in Description 43, 785 mg, 1.54 mmol) in DCM (5 mL) at $0^{\alpha}$C was added DMP (784 mg, 1.85 mmol) then the mixture was stirred at room temperature for 2.5h. The reaction mixture was filtered, and the organic layer concentrated in vacuo. The sample was purified by silica chromatography (25 g) using a 0-30% [3:1 EtOAc:ethanol]/cyclohexane gradient. The appropriate fractions were combined and concentrated in vacuo, then the residue was precipitated from DCM and TBME to give the required product (580 mg, 67% yield) as a white solid. LCMS (formic B): Rt=1.44 min, MH+=508.

Description 45 tert-Butyl (3S,4R)-4-(4-bromo-1H-indazol-1-yl)-3-fluoropiperidine-1-carboxylate (D45)

tert-Butyl (3S,4S)-3-fluoro-4-hydroxypiperidine-1-carboxylate (601 mg, 2.74 mmol) and 4-bromo-1H-indazole (300 mg, 1.52 mmol) were placed in a vial, then sealed, evacuated and purged with nitrogen three times. Toluene (9 mL) was added followed by addition of CMBP (800 μL, 3.05 mmol), then the mixture was stirred at 95° C. for 15.5 h. This procedure was duplicated in a second vial. The reaction mixtures were cooled to rt, combined and evaporated in vacuo. The sample was purified by silica chromatography (40 g) using a 0-25% EtOAc/cyclohexane gradient, then the appropriate fractions were combined and evaporated in vacuo to give the required product (556 mg, 43% yield) as a pale yellow foam. LCMS (high pH B): Rt=2.33 min, [M-tBu]+=342/344.

Description 46 tert-Butyl (3S,4R)-4-(4-(2,4-dioxo-3-((2-(trimethylsilyl)ethoxy)methyl)tetrahydropyrimidin-1(2H)-yl)-1H-indazol-1-yl)-3-fluoropiperidine-1-carboxylate (D46)

A vial was charged with copper(I) iodide (35.4 mg, 186 μmol), 3-((2-(trimethylsilyl)ethoxy)methyl)dihydropyrimidine-2,4(1H,3H)-dione (may be prepared as described in D4, 261 mg, 1.07 mmol) and potassium carbonate (257 mg, 1.86 mmol), then a solution of tert-butyl (3S,4R)-4-(4-bromo-1H-indazol-1-yl)-3-fluoropiperidine-1-carboxylate (may be prepared as described in Description 45, 370 mg, 929 μmol) in 1,4-dioxane (7 mL) was added followed by trans-N,N'-dimethylcyclohexane-1,2-diamine (58.6 μL, 372 μmol). The reaction mixture was sparged with nitrogen, then the mixture was stirred at 140° C. for 15 h. This procedure was duplicated in a second vial. The two reaction mixtures were cooled to room temperature and diluted with EtOAc, then combined and filtered through Celite. The filtrate was diluted with water then the phases were separated. The aqueous layer was back-extracted with EtOAc, then the organic layers were combined, washed twice with water, dried over sodium sulfate and evaporated in vacuo. The sample was purified by silica chromatography (80 g) using a 0-40% EtOAc/cyclohexane gradient however this failed to completely separate the product. The appropriate fractions were combined and evaporated in vacuo, then the sample was purified by prep HPLC (high pH). The appropriate fractions were combined and evaporated in vacuo to give the required product (721 mg, 60% yield) as a white solid. LCMS (high pH B): Rt=2.32 min, MH+=does not ionise.

Description 47

1-(1-((3S,4R)-3-Fluoropiperidin-4-yl)-1H-indazol-4-yl)dihydropyrimidine-2,4(1H,3H)-dione (D47)

To a solution of tert-butyl (3S,4R)-4-(4-(2,4-dioxo-3-((2-(trimethylsilyl)ethoxy)methyl)tetrahydropyrimidin-1(2H)-yl)-1H-indazol-1-yl)-3-fluoropiperidine-1-carboxylate (may be prepared as described in Description 46, 0.715 g, 1.27 mmol) in DCM (10 mL) at 0° C. was added TFA (1.94 mL, 25.5 mmol) dropwise, then the mixture was stirred at room temperature for 3.5 h. The reaction mixture was concentrated in vacuo, then the sample was dissolved in methanol (2 mL) and treated with ammonia (7M in methanol, 10.9 mL, 76.4 mmol). The mixture was stirred at room temperature for 1 h, then concentrated in vacuo. The sample was purified by prep HPLC (high pH), then the appropriate fractions were combined and evaporated in vacuo to give the required product (171 mg, 38% yield) as a white solid. LCMS (high pH B): Rt=1.28 min, MH+=332.

Description 48 tert-Butyl ((1r,3r)-3-((8-cyanoquinolin-5-yl)oxy)-2,2,4,4-tetramethylcyclobutyl)carbamate (D48)

To a stirred solution of trans-tert-butyl 3-hydroxy-2,2,4,4-(tetramethyl)cyclobutylcarbamate (1.00 g, 1.00 Eq, 4.11 mmol) and 5-fluoroquinoline-8-carbonitrile (707 mg, 4.11 mmol) in MeCN (20 mL) was added cesium carbonate (3.35 g, 10.3 mmol) then the mixture heated at 100° C. for 5 h. DMF (10 mL) was added to aid solubility, then the mixture was heated at 100° C. for a further 20 h. The mixture was added to water (200 mL), then the solution was extracted with EtOAc (3×100 mL). The organic layers were combined, washed with brine, dried using a hydrophobic frit and evaporated in vacuo. The sample was loaded on florisil and purified on Si (80 g) using a 0-50% EtOAc-cyclohexane gradient over 12 column volumes. The appropriate fractions were combined and evaporated in vacuo to give the desired product (682 mg, 42% yield) as an off-white solid. LCMS (high pH A): Rt=1.33 min, $MH^+$=396.

Description 49

5-((1r,3r)-3-Amino-2,2,4,4-tetramethylcyclobutoxy) quinoline-8-carbonitrile, Dihydrochloride (D49)

To a stirred solution of tert-butyl ((1r,3r)-3-((8-cyanoquinolin-5-yl)oxy)-2,2,4,4-tetramethylcyclobutyl)carbamate (may be prepared as described in Description 48; 680 mg, 1.72 mmol) in DCM (15 mL) was added HCl (4M in dioxane, 4.30 mL, 17.2 mmol) then the mixture stirred at room temperature for 66 h. The reaction mixture was concentrated in vacuo and dried to give the desired product (640 mg, quantitative yield) as a white solid. LCMS (high pH A): Rt=0.97 min, $MH^+$=296.

Description 50

N-((1r,3r)-3-((8-Cyanoquinolin-5-yl)oxy)-2,2,4,4-tetramethylcyclobutyl)-4-(4-(hydroxymethyl)piperidin-1-yl)benzamide (D50)

To a stirred suspension of 4-(4-(hydroxymethyl)piperidin-1-yl)benzoic acid (may be prepared as described in Description 38, 303 mg, 1.29 mmol) and 5-((1r,3r)-3-amino-2,2,4,4-tetramethylcyclobutoxy)quinoline-8-carbonitrile dihydrochloride (may be prepared as described in Description 49; 450 mg, 1.22 mmol, may be prepared as described in D49) in DCM (10 mL) was added DIPEA (1.06 mL, 6.11 mmol) then HATU (488 mg, 1.28 mmol) and the mixture stirred at room temperature for 30 min. The reaction mixture was concentrated in vacuo, then the sample was purified on Si (40 g) using a 0-100% EtOAc/cyclohexane gradient. The appropriate fractions were combined and evaporated in vacuo to give the required product (689 mg, 93% yield, 85% purity) as a white solid which was used directly in the next reaction. LCMS (high pH A): Rt=1.16 min, MH+=513.

Description 51

N-((1r,3r)-3-((8-Cyanoquinolin-5-yl)oxy)-2,2,4,4-tetramethylcyclobutyl)-4-(4-formylpiperidin-1-yl) benzamide (D51)

To a stirred solution of N-((1r,3r)-3-((8-cyanoquinolin-5-yl)oxy)-2,2,4,4-tetramethylcyclobutyl)-4-(4-(hydroxymethyl)piperidin-1-yl)benzamide (may be prepared as described in Description 50, 685 mg, 85% weight, 1.14 mmol) in DCM (15.0 mL) was added DMP (723 mg, 1.70 mmol) then the mixture stirred at room temperature for 20 min. The reaction mixture was concentrated in vacuo, then directly purified on Si (40 g) using a 0-100% EtOAc-cyclohexane gradient over 14 column volumes. The appropriate fractions were combined and evaporated in vacuo to give the required product (581 mg, 100% yield) as a brown solid. LCMS (formic A): Rt=1.21 min, MH+=511.

Description 52

Methyl 3,5-difluo 4-(4-(hydroxymethyl)piperidin-1-yl)benzoate (D52)

A mixture of methyl 3,4,5-trifluorobenzoate (1.19 g, 6.24 mmol), piperidin-4-ylmethanol (790 mg, 6.86 mmol), and potassium carbonate (1.04 g, 7.49 mmol) in DMAc (12 mL) was stirred at 100° C. for 3 h. The reaction was cooled to room temperature and poured into water (100 mL) and EtOAc (30 mL) then the phases were separated. The aqueous layer was back-extracted with EtOAc (2×10 mL), then the organic layers were combined, washed sequentially with LiCl (5% aq.) and brine, dried using a hydrophobic frit and evaporated in vacuo to give the required product (1.74 g, 88% yield) as a light yellow oil. LCMS (high pH A): Rt=1.07 min, MH+=286.

Description 53

3,5-Difluoro-4-(4-(hydroxymethyl)piperidin-1-yl) benzoic Acid (D53)

To a solution of methyl 3,5-difluoro-4-(4-(hydroxymethyl)piperidin-1-yl)benzoate (may be prepared as described in Description 52, 1.74 g, 6.10 mmol) in methanol (6 mL) was added NaOH (2M aq., 6.10 mL, 12.2 mmol) then the mixture was stirred at room temperature for 5 h. The reaction was neutralised with (2M aq., 6 mL), then the resulting precipitate was collected by filtration, washed with water and dried under air and high vacuum to give the required product (1.44 g, 86% yield) as a white solid. LCMS (formic A): Rt=0.87 min, MH+=272.

Description 54

N-((1r,3r)-3-((8-Cyanoquinolin-5-yl)oxy)-2,2,4,4-tetramethylcyclobutyl)-3,5-difluoro-4-(4-(hydroxymethyl)piperidin-1-yl)benzamide (D54)

To a suspension of 3,5-difluoro-4-(4-(hydroxymethyl) piperidin-1-yl)benzoic acid (may be prepared as described in Description 53, 155 mg, 570 μmol) and 5-((1r,3r)-3-amino-2,2,4,4-tetramethylcyclobutoxy)quinoline-8-carbonitrile dihydrochloride (may be prepared as described D49, 200 mg, 543 μmol) in DMF (3 mL) was added DIPEA (473 μL, 2.72 mmol) and HATU (227 mg, 597 μmol), then the reaction mixture was stirred at room temperature for 3 h. The mixture was partitioned between EtOAc (10 mL) and water (30 mL) then the phases were separated. The aqueous layer was back-extracted with EtOAc (10 mL), then the organic layers were combined, washed sequentially with HCl (1M aq., 10 mL) and brine, dried using a hydrophobic frit and evaporated to give the required product (368 mg, 98% yield, 79% purity) as yellow gum which was used directly in the next reaction. LCMS (formic A): Rt=1.25 min, MH+=549.

Description 55

N-((1r,3r)-3-((8-Cyanoquinolin-5-yl)oxy)-2,2,4,4-tetramethylcyclobutyl)-3,5-difluoro-4-(4-formylpiperidin-1-yl)benzamide (D55)

To a stirred solution of N-((1r,3r)-3-((8-cyanoquinolin-5-yl)oxy)-2,2,4,4-tetramethylcyclobutyl)-3,5-difluoro-4-(4-(hydroxymethyl)piperidin-1-yl)benzamide (may be prepared as described in Description 54, 368 mg, 79% weight, 530 μmol) in DCM (4 mL) was added DMP (337 mg, 795 μmol) then the mixture stirred at room temperature for 1 h. The reaction was partitioned between DCM (10 mL) and $NaHCO_3$ (sat. aq., 10 mL), then the aqueous was back-extracted with DCM (2×10 mL). The organic layers were combined, dried using a hydrophobic frit and evaporated in vacuo. The sample was purified by silica chromatography using a 0-100% [3:1 EtOAc:ethanol]/cyclohexane gradient, then the appropriate fractions were combined and evaporated in vacuo to give the required product (303 mg, 78% yield, 75% purity) as a yellow gum which was used directly in the next reaction. LCMS (formic A): Rt=1.35 min, MH+=547.

Description 56

N-((1r,3r)-3-((8-Cyanoquinolin-5-yl)oxy)-2,2,4,4-tetramethylcyclobutyl)-3-fluoro-4(4-(hydroxymethyl)piperidin-1-yl)benzamide (D56)

To a stirred solution of 3-fluoro-4-(4-(hydroxymethyl) piperidin-1-yl)benzoic acid (may be prepared as described in Description 30, 371 mg, 1.46 mmol), 5-((1r,3r)-3-amino-2,2,4,4-tetramethylcyclobutoxy)quinoline-8-carbonitrile dihydrochloride (may be prepared as described in Description 49; 393 mg, 1.33 mmol) and DIPEA (1.16 mL, 6.65 mmol) in DCM (10 mL) was added HATU (556 mg, 1.46 mmol) then the mixture stirred at room temperature for 30 min. The reaction mixture was concentrated in vacuo, then directly purified on by silica chromatography (80 g) using a 0-100% EtOAc/cyclohexane gradient. The appropriate fractions were combined and evaporated in vacuo to give the required product (612 mg, 78% yield) as a white gum. LCMS (high pH A): Rt=1.18 min, $MH^+$=531.

Description 57

N-((1r,3r)-3-((8-Cyanoquinolin-5-yl)oxy)-2,2,4,4-tetramethylcyclobutyl)-3-fluoro-4-(4-formylpiperidin-1-yl)benzamide (D57)

To a solution of N-((1r,3r)-3-((8-cyanoquinolin-5-yl) oxy)-2,2,4,4-tetramethylcyclobutyl)-3-fluoro-4-(4-(hydroxymethyl)piperidin-1-yl)benzamide (may be prepared as described in Description 56, 500 mg, 942 μmol) in DCM (10 mL) at 0° C. was added DMP (480 mg, 1.13 mmol) then the mixture was stirred at room temperature for 1 h. Further DMP (120 mg, 283 μmol) then the mixture was stirred at room temperature for 1.5 h. The reaction mixture was diluted with DCM and washed sequentially with $NaHCO_3$ (sat. aq.), $Na_2CO_3$ (10% aq.) and brine, dried over anhydrous sodium sulfate and concentrated in vacuo. The sample was purified by silica chromatography (12 g) using a 0-50% EtOAc/cyclohexane gradient. The appropriate fractions were combined and evaporated in vacuo to give the required product (358 mg, 68% yield) as a white solid. LCMS (formic A): Rt=1.40 min, MH+=530.

Description 58

Methyl (R)-3-fluoro-4-(3-(hydroxymethyl)pyrrolidin-1-yl)benzoate (D58)

To a solution of methyl 3,4-difluorobenzoate (550 mg, 3.20 mmol) in DMAc (6 mL) was added $K_2CO_3$ (530 mg, 3.83 mmol) and (R)-pyrrolidin-3-ylmethanol (388 mg, 3.83 mmol) then the mixture was stirred at 100° C. for 36 h. The mixture was cooled to rt then diluted with water and extracted twice with EtOAc. The organic layers were combined, dried over sodium sulfate, filtered and concentrated in vacuo. The sample was purified by silica chromatography (25 g) using a 0-50% EtOAc/cyclohexane gradient, then the appropriate fractions were combined and evaporated in vacuo to give the required product (680 mg, 76% yield) as a white solid. LCMS (formic B): Rt=1.11 min, MH+=254.

Description 59

(R)-3-Fluoro-4-(3-(hydroxymethyl)pyrrolidin-1-yl) benzoic Acid (D59)

To a stirred solution of methyl (R)-3-fluoro-4-(3-(hydroxymethyl)pyrrolidin-1-yl)benzoate (may be prepared as described in Description 58, 680 mg, 2.68 mmol) in methanol (10 mL) was added NaOH (2M aq., 4.03 mL, 8.05 mmol) then the mixture was stirred at room temperature for 16 h. The reaction mixture was concentrated in vacuo, then dissolved in water (30 mL) and the pH adjusted to 2 with HCl (4M aq.). The resulting solid was separated by filtration and washed sequentially with water and hexane to give the required product (561 mg, 80% yield) as a pale pink solid. LCMS (formic B): Rt=0.88 min, MH+=240.

Description 60

N-((1r,3R)-3-((8-cyanoquinolin-1-yl)oxy)-2,2,4,4-tetramethylcyclobutyl)-3-fluoro-4-((R)-3-(hydroxymethyl)pyrrolidin-1-yl)benzamide (D60)

To a stirred solution of (R)-3-fluoro-4-(3-(hydroxymethyl)pyrrolidin-1-yl)benzoic acid (may be prepared as described in Description 59, 541 mg, 2.26 mmol) and HATU (1.29 g, 3.39 mmol) in DMF (20 mL) was added DIPEA (1.57 mL, 9.04 mmol) and 5-((1r,3r)-3-amino-2,2,4,4-tetramethylcyclobutoxy)quinoline-8-carbonitrile dihydrochloride (may be prepared as described in D49, 750 mg, 2.26 mmol) then the mixture was stirred at room temperature for 18 h. The reaction mixture was quenched with $NH_4Cl$ (sat. aq.) and extracted with EtOAc. The phases were separated, then the organic layer was evaporated in vacuo. The sample was purified by silica chromatography (25 g) using a 0-50% [3:1 EtOAc:ethanol]/cyclohexane gradient. The appropriate fractions were combined and evaporated in vacuo to give the required product (930 mg, 80% purity, 64% yield) which was used directly in the next reaction. LCMS (formic B): Rt=1.30 min, MH+=517.

Description 61

N-((1r,3R)-3-((8-Cyanoquinolin-5-yl)oxy)-2,2,4,4-tetramethylcyclobutyl)-3-fluoro-4-((R)-3-formylpyrrolidin-1-yl)benzamide (D61)

To a stirred solution of N-((1r,3R)-3-((8-cyanoquinolin-5-yl)oxy)-2,2,4,4-tetramethylcyclobutyl)-3-fluoro-4-((R)-3-(hydroxymethyl)pyrrolidin-1-yl)benzamide (may be prepared as described in Description 60, 150 mg, 290 μmol) in DCM (5 mL) at 0° C. was added DMP (148 mg, 348 μmol) then the mixture was stirred at room temperature for 1 h. Further DMP (49 mg, 116 μmol) was added then the mixture was stirred at room temperature for 1 h. Further DMP (49 mg, 116 μmol) was added then the mixture was stirred at room temperature for 1 h. The reaction mixture was filtered then the filtrate was concentrated in vacuo. The sample was purified by silica chromatography (10 g) using a 0-30% [3:1 EtOAc:ethanol]/cyclohexane gradient. The appropriate fractions were combined and evaporated in vacuo to give the required product (108 mg, 58% yield, 80% purity) as a white solid that was used directly in the next reaction. LCMS (formic B): Rt=1.37 min, MH+=515.

Description 62

Methyl (S)-3-fluoro-4-(3-(hydroxymethyl)pyrrolidin-1-yl)benzoate (D62)

To a solution of methyl 3,4-difluorobenzoate (700 mg, 4.07 mmol) in DMAc (8 mL) was added $K_2CO_3$ (1.41 g, 10.2 mmol) and (5)-pyrrolidin-3-ylmethanol hydrochloride (672 mg, 4.88 mmol) then the resulting mixture was stirred at 100° C. for 18 h. The mixture was cooled to rt and diluted with water, then extracted twice with EtOAc. The organic layers were combined, dried over sodium sulfate, filtered and evaporated in vacuo. The sample was purified by silica chromatography (25 g) using a 0-50% EtOAc/cyclohexane gradient. The appropriate fractions were combined and evaporated in vacuo to give the required product (879 mg, 81% yield) as a white solid. LCMS (formic B): Rt=1.11 min, MH+=254

Description 63

(S)-3-Fluoro-4-(3-(hydroxymethyl)pyrrolidin-1-yl) benzoic Acid (D63)

To a stirred solution of methyl (5)-3-fluoro-4-(3-(hydroxymethyl)pyrrolidin-1-yl)benzoate (may be prepared as described in Description 62, 680 mg, 2.68 mmol) in methanol (10 mL) was added NaOH (2M aq., 4.03 mL, 8.05 mmol) then the mixture was stirred at rt for 16 h. Further NaOH (2M aq., 1.34 mL, 2.68 mmol) was added and the mixture stirred at room temperature for 4 h. The reaction mixture was concentrated in vacuo, then the sample was dissolved in water (30 mL) and the pH adjusted to 2 with HCl (4M aq.). The resulting precipitate was separated by filtration and vacuum dried to give the required product (781 mg, 80% purity, 97% yield) as a white solid which was used directly in the next reaction. LCMS (formic B): Rt=0.88 min, MH+=240.

Description 64

N-((1r,3S)-3-((8-Cyanoquinolin-1-yl)oxy)-2,2,4,4-tetramethylcyclobutyl)-3-fluoro-4-((S)-3-(hydroxymethyl)pyrrolidin-1-yl)benzamide (D64)

To a solution of (5)-3-fluoro-4-(3-(hydroxymethyl)pyrrolidin-1-yl)benzoic acid (may be prepared as described in Description 63, 781 mg, 80% weight, 2.61 mmol) in DMF (20 mL), was added HATU (1.49 g, 3.92 mmol) and DIPEA (1.82 mL, 10.4 mmol) followed by 5-((1r,3r)-3-amino-2,2,4,4-tetramethylcyclobutoxy)quinoline-8-carbonitrile dihydrochloride (may be prepared as described D49, 867 mg, 2.61 mmol) then the mixture was stirred at room temperature for 18 h. The reaction mixture was quenched with $NH_4Cl$ (sat. aq.) and extracted with EtOAc. The phases were separated, then the organic layer was evaporated in vacuo. The sample was purified by silica chromatography (40 g) using a 0-40% [3:1 EtOAc:ethanol]/cyclohexane gradient, however this failed to completely separate the product. The appropriate fractions were combined and evaporated in vacuo, then the sample was purified by prep HPLC (high pH), then the appropriate fractions were combined and evaporated in vacuo to give the required product (598 mg, 42% yield). LCMS (formic B): Rt=1.29 min, MH+=517.

Description 65

N-((1r,3S)-3-((8-Cyanoquinolin-1-yl)oxy)-2,2,4,4-tetramethylcyclobutyl)-3-fluoro-4-((S)-3-formylpyrrolidin-1-yl)benzamide (D65)

To a stirred solution of N-((1r,3S)-3-((8-cyanoquinolin-5-yl)oxy)-2,2,4,4-tetramethylcyclobutyl)-3-fluoro-4-((S)-3-(hydroxymethyl)pyrrolidin-1-yl)benzamide (may be prepared as described in Description 64, 400 mg, 774 μmol) in DCM (5 mL) at 0° C. was added DMP (394 mg, 929 μmol) then the mixture was stirred at room temperature for 2.5 h. The reaction mixture was filtered, then the filtrate was concentrated in vacuo. The sample was purified by silica chromatography (10 g) using a 0-30% [3:1 EtOAc:ethanol]/cyclohexane gradient. The appropriate fractions were combined and evaporated in vacuo to give the required product (209 mg, 78% yield) as a pale brown solid. LCMS (formic B): Rt=1.35 min, MH+=515.

Description 66

Methyl 2,5-difluoro-4-(4-(hydroxymethyl)piperidin-1-yl)benzoate (D66)

To a solution of methyl 2,4,5-trifluorobenzoate (960 mg, 5.05 mmol) and piperidin-4-ylmethanol (698 mg, 6.06 mmol) in DMSO (15 mL) was added DIPEA (2.64 mL, 15.1 mmol) and the heated at 90° C. for 16 h. The reaction mixture was poured into ice-cold water (40 mL) and extracted with TBME (3×50 mL). The organic layers were combined, washed with brine (20 mL), dried over sodium sulfate, filtered and concentrated in vacuo. The sample was purified by silica chromatography (40 g) using a 0-100% EtOAc/cyclohexane gradient. The appropriate fractions were combined and evaporated in vacuo to give the required product (1.39 g, 92% yield) as a white solid. LCMS (formic B): Rt=1.14 min, MH+=286.

Description 67

2,5-Difluoro-4-(4-(hydroxymethyl)piperidin-1-yl) benzoic Acid (D67)

To a solution of methyl 2,5-difluoro-4-(4-(hydroxymethyl)piperidin-1-yl)benzoate (may be prepared as described in Description 66, 172 mg, 603 μmol) in methanol (1.3 mL) was added NaOH (2M aq., 754 μL, 1.51 mmol) then the mixture was stirred at room temperature for 25 h. The reaction mixture was concentrated in vacuo, then the sample was dissolved in water (5 mL) and the pH adjusted to ~2 using HCl (2M aq.). The resulting suspension was extracted with EtOAc (2×25 mL), then the organic layers were combined, washed with brine (10 mL), dried over sodium sulfate, filtered and evaporated in vacuo to give the required product (65 mg, 36% yield) as a white solid. LCMS (formic B): Rt=0.88 min, MH+=272.

Description 68

N-((1r,3r)-3-((8-Cyanoquinolin-5-yl)oxy)-2,2,4,4-tetramethylcyclobutyl)-2,5-difluoro-4-(4-(hydroxymethyl)piperidin-1-yl)benzamide (D68)

To a mixture of 2,5-difluoro-4-(4-(hydroxymethyl)piperidin-1-yl)benzoic acid (may be prepared as described in Description 67, 61.0 mg, 225 μmol), DIPEA (196 μL, 1.12 mmol) and HATU (103 mg, 270 μmol) in DMF (2 mL) was added 5-((1r,3r)-3-amino-2,2,4,4-tetramethylcyclobutoxy)quinoline-8-carbonitrile dihydrochloride (82.1 mg, 247 μmol, may be prepared as described in D49) then the mixture was stirred at room temperature for 18 h. The mixture was diluted with EtOAc (40 mL), washed sequentially with ice-cold $NH_4Cl$ (sat. aq., 2×10 mL), water (10 mL) and brine (10 mL). The organic layers were combined, dried over sodium sulfate, filtered and concentrated in vacuo. The sample was purified by silica chromatography (12 g) using a 0-100% EtOAc/cyclohexane gradient. The appropriate fractions were combined and evaporated in vacuo to give the required product (127 mg, 98% yield) as a colourless oil. LCMS (formic B): Rt=1.37 min, MH+=549.

Description 69

N-((1r,3r)-3-((8-Cyanoquinolin-5-yl)oxy)-2,2,4,4-tetramethylcyclobutyl)-2,5-difluoro-4-(4-formylpiperidin-1-yl)benzamide (D69)

DMP (113 mg, 265 μmol) was added to a stirred solution of N-((1r,3r)-3-((8-cyanoquinolin-5-yl)oxy)-2,2,4,4-tetramethylcyclobutyl)-2,5-difluoro-4-(4-(hydroxymethyl)piperidin-1-yl)benzamide (may be prepared as described in Description 68, 112 mg, 204 μmol) in DCM (3 mL) at 0° C. The reaction mixture was allowed to warm to room temperature, then the mixture was stirred at room temperature for 3 h. Further DMP (113 mg, 265 μmol) was added then the mixture was stirred at room temperature for 18 h. The reaction mixture was diluted with DCM and treated with $Na_2CO_3$ (10% aq.), then the phases were separated. The organic layer was washed sequentially with $Na_2CO_3$ (10% aq.) twice then brine and dried over sodium sulfate, filtered and evaporated in vacuo. The sample was purified by silica chromatography (12 g) using a 0-100% EtOAc/cyclohexane gradient. The appropriate fractions were combined and evaporated in vacuo to give the required product (62 mg, 53% yield) as a white solid. LCMS (high pH D): Rt=1.90 min, MH+=547.

Description 70 tert-Butyl (R)-3-(4-bromo-1H-indazol-1-yl)pyrrolidine-1-carboxylate (D70)

Cesium carbonate (5.25 g, 16.1 mmol) was added to a stirred solution of 4-bromo-1H-indazole (2.12 g, 10.7 mmol) and tert-butyl (5)-3-((methylsulfonyl)oxy)pyrrolidine-1-carboxylate (2.94 g, 10.7 mmol) in DMF (40 mL), then the mixture was stirred at 60° C. for 23 h. The mixture was cooled to room temperature, diluted with EtOAc, $NH_4Cl$ (sat. aq.) and water, then the phases were separated. The aqueous layer was back-extracted with EtOAc, then the organic layers were combined, washed with brine, dried over sodium sulfate and evaporated in vacuo. The sample was purified by silica chromatography (220 g) using a 0-50% EtOAc/cyclohexane gradient, then the appropriate fractions were combined and evaporated in vacuo to give the required product (2.33 g, 55% yield) as a viscous yellow oil. LCMS (high pH C) Rt=2.52 min, MH+=266/268 (weak ionisation).

Description 71 tert-Butyl (R)-3-(4-(2,4-dioxo-3-((2-(trimethylsilyl)ethoxy)methyl)tetrahydropyrimidin-1(2H)-yl)-1H-indazol-1-yl)pyrrolidine-1-carboxylate (D71)

tert-Butyl (R)-3-(4-bromo-1H-indazol-1-yl)pyrrolidine-1-carboxylate (may be prepared as described in Description 70, 2.33 g, 6.37 mmol), 3-((2-(trimethylsilyl)ethoxy)methyl)dihydropyrimidine-2,4(1H,3H)-dione (may be prepared as described in D4, 1.80 g, 7.37 mmol), potassium carbonate (1.80 g, 13.0 mmol), copper(I) iodide (244 mg, 1.28 mmol), 1,4-dioxane (30 mL) and (1R,2R)—N1,N2-dimethylcyclohexane-1,2-diamine (402 μL, 2.55 mmol) were added to a vial. The mixture was sparged with nitrogen, then the vial was sealed and heated at 140° C. for 23 h. The reaction mixture was cooled to room temperature, diluted with EtOAc and water, filtered through Celite, then the phases were separated. The aqueous layer was back-extracted twice with EtOAc, then the organic layers were combined, washed with brine, dried over sodium sulfate, filtered and evaporated in vacuo. The sample was purified by silica chromatography (120 g) using a 0-50% EtOAc/cyclohexane gradient, then the appropriate fractions were combined and evaporated in vacuo to give the required product (2.80 g, 76% yield) as a white foam. LCMS (high pH D): Rt=1.97 min, MH+=does not ionise.

Description 72

(R)-1-(1-(Pyrrolidin-3-yl)-1H-indazol-4-yl)dihydropyrimidine-2,4(1H,3H)-dione (D72)

A stirred solution of tert-butyl (R)-3-(4-(2,4-dioxo-3-((2-(trimethylsilyl)ethoxy)methyl)tetrahydropyrimidin-1(2H)-yl)-1H-indazol-1-yl)pyrrolidine-1-carboxylate (may be prepared as described in Description 71, 2.80 g, 5.28 mmol) in DCM (60 mL) was cooled to 0° C., TFA (8.15 mL, 106 mmol) was added, then the mixture was stirred at room temperature for 4 h. The reaction mixture was evaporated in vacuo, then azeotroped with toluene (2×150 mL). The residue was treated with ammonia (7M in methanol, 200 mL), then the mixture was stirred at room temperature for 6 h. The reaction mixture was evaporated in vacuo, then the sample was purified by prep HPLC (high pH). The appropriate fractions were combined and evaporated in vacuo to give the required product (1.43 g, 78% yield, 86% purity) as a sticky brown solid. LCMS (high pH E): Rt=1.22 min, MH+=300.

Description 73

Ethyl 3-chloro-4-(4-(hydroxymethyl)piperidin-1-yl)benzoate (D73)

To a solution of ethyl-3-chloro-4-fluorobenzoate (400 mg, 1.97 mmol) and 4-piperidinemethanol (250 mg, 2.17 mmol) in DMAc (5 mL) was added potassium carbonate (409 mg, 2.96 mmol), then the mixture was stirred at 100° C. for 17.5 h. The mixture was cooled to rt, then diluted with EtOAc and water and the phases separated. The aqueous layer was back-extracted with EtOAc three times, then the organic layers were combined, dried over sodium sulfate, filtered and evaporated in vacuo. The sample was purified by silica chromatography (40 g) using a 0-30% EtOAc/cyclohexane gradient. The appropriate fractions were combined and evaporated in vacuo to give the required product (529 mg, 82% yield, 91% purity) as a colourless oil. LCMS (high pH C): Rt=2.17 min, MH+=298.

Description 74

3-Chloro-4-(4-(hydroxymethyl)piperidin-1-yl)benzoic Acid (D74)

NaOH (2M aq., 2.30 mL, 4.60 mmol) was added to a stirred solution of ethyl 3-chloro-4-(4-(hydroxymethyl)piperidin-1-yl)benzoate (may be prepared as described in Description 73, 499 mg, 91% weight, 1.52 mmol) in methanol (7.6 mL), then the mixture was stirred at room temperature for 15 h. The reaction mixture was concentrated in vacuo, then the sample was diluted with water and the pH adjusted to ~3 with HCl (1M aq.). The resulting precipitate was separated by filtration and dried to give the required product (397 mg, 92% yield) as a white solid. LCMS (high pH E): Rt=1.14 min, MH+=270.

Description 75

3-Chloro-N-((1r,3r)-3-((8-cyanoquinolin-5-yl)oxy)-2,2,4,4-tetramethylcyclobutyl)-4-(4-(hydroxymethyl)piperidin-1-yl)benzamide (D75)

To a solution of 3-chloro-4-(4-(hydroxymethyl)piperidin-1-yl)benzoic acid (may be prepared as described in Description 74, 201 mg, 745 μmol), HATU (386 mg, 1.02 mmol) and DIPEA (0.35 mL, 2.03 mmol) in DMF (3.4 mL) was added 5-((1r,3r)-3-amino-2,2,4,4-tetramethylcyclobutoxy)quinoline-8-carbonitrile dihydrochloride (may be prepared as described in D49, 200 mg, 677 μmol) then the mixture was stirred at room temperature for 2 h. The mixture was diluted with EtOAc and $NH_4Cl$ (sat. aq.) then the phases were separated. The organic layer was washed with further $NH_4Cl$ (sat. aq.) then the aqueous phases were combined and back-extracted with EtOAc (2×20 mL). The organic layers were combined, dried over sodium sulfate, filtered and evaporated in vacuo. The sample was purified by silica chromatography (25 g) using a 0-100% EtOAc/cyclohexane gradient. The appropriate fractions were combined and evaporated in vacuo to give the required product (163 mg, 42% yield) as a white solid. LCMS (high pH B): Rt=2.09 min, MH+=547.

Description 76

3-Chloro-N-((1r,3r)-3-((8-cyanoquinolin-5-yl)oxy)-2,2,4,4-tetramethylcyclobutyl)-4-(4-formylpiperidin-1-yl)benzamide (D76)

To a solution of 3-choro-N-((1r,3r)-3-((8-cyanoquinolin-5-yl)oxy)-2,2,4,4-tetramethylcyclobutyl)-4-(4-(hydroxymethyl)piperidin-1-yl)benzamide (may be prepared as described in Description 75, 0.160 g, 292 μmol) in DCM (4 mL) was added DMP (161 mg, 380 μmol) then the mixture was stirred at room temperature for 2 h 15 min. Further DMP (24.8 mg, 58.5 μmol) was added, then the mixture was stirred at room temperature for 30 min. The mixture was diluted with DCM and $NaHCO_3$ (sat. aq.) then the phases were separated. The organic layer was washed with $Na_2CO_3$ (10% aq.), then the aqueous phases were combined and back-extracted with DCM (2×15 mL). The organic layers were combined, dried over sodium sulfate, filtered and evaporated in vacuo. The sample was purified by silica chromatography (25 g) using a 0-50% EtOAc/cyclohexane gradient, then the appropriate fractions were combined and evaporated in vacuo to give the required product (135 mg, 66% yield) as a white foam. LCMS (high pH B): Rt=2.31 min, MH+=545.

Description 77

(1-(4-(((1r,3r)-3-((8-Cyanoquinolin-5-yl)oxy)-2,2,4,4-tetramethylcyclobutyl)carbamoyl)-2-fluorophenyl)piperidin-4-yl)methyl methanesulfonate (D77)

A stirred solution of N-((1r,3r)-3-((8-cyanoquinolin-5-yl)oxy)-2,2,4,4-tetramethylcyclobutyl)-3-fluoro-4-(4-(hydroxymethyl)piperidin-1-yl)benzamide (may be prepared as described in Description 56, 610 mg, 1.03 mmol) and triethylamine (216 μL, 1.55 mmol) in DCM (10 mL) was cooled to 0° C., then mesyl chloride (96.7 μL, 1.24 mmol) was added dropwise and the mixture stirred at room temperature for 3 h. The mixture was diluted with DCM (10 mL) and HCl (0.1 M aq., 20 mL) and the phases were separated. The aqueous layer was back-extracted with DCM (10 mL), then the organic layers were combined and evaporated in vacuo to give the required product (720 mg, quantitative yield) as a white solid which was used in the next reaction without further purification. LCMS (high pH A): Rt=1.30 min, MH+=609.

Description 78 tert-Butyl 4-((4-(4-(2-dioxotetrahydropyrimidin-1(2H)-yl)-1H-indazol-1-yl)piperidin-1-yl)methyl)-4-hydroxypiperidine-1-carboxylate (D78)

To a stirred solution of 1-(1-(piperidin-4-yl)-1H-indazol-4-yl)dihydropyrimidine-2,4(1H,3H)-dione 2,2,2-trifluoroacetate (may be prepared as described in D7 320 mg, 749 μmol) and DIPEA (391 μL, 2.25 mmol) in DMSO (5 mL) was added tert-butyl 1-oxa-6-azaspiro[2.5]octane-6-carboxylate (176 mg, 824 μmol) then the mixture was heated to 100° C. for 17 h. The mixture was poured into water, (100 mL) then the suspension was extracted with DCM (3×50 mL). The organic layers were combined, dried using a hydrophobic frit and evaporated in vacuo. The sample was loaded in minimal DCM and purified by silica chromatography (40 g) using a 0-25% ethanol-EtOAc (+1% triethylamine) gradient over 12 column volumes. The appropriate fractions were combined and evaporated in vacuo to give the required product (249 mg, 63% yield) as a yellow solid. LCMS (high pH A): Rt=1.02 min, MH+=527.

Description 79

1-(1-(1-((4-Hydroxypiperidin-4-yl)ethyl)piperidin-4-yl)-1H-indazol-4-yl)dihydropyrimidine-2,4(1H,3H)-dione Trihydrochloride (D79)

To a stirred solution of tert-butyl 4-((4-(4-(2,4-dioxotetrahydropyrimidin-1(2H)-yl)-1H-indazol-1-yl)piperidin-1-yl)methyl)-4-hydroxypiperidine-1-carboxylate (may be prepared as described in Description 78, 248 mg, 471 μmol) in DCM (6 mL) was added HCl (4M in dioxane, 1.18 mL, 4.71 mmol) then the mixture was stirred at room temperature for 2.5 h. The reaction mixture was concentrated in vacuo and the resulting solid was vacuum dried to give the required product (277 mg, quantitative yield) as a white solid. LCMS (high pH A) Rt=0.68 min, MH+=427.

Description 80 tert-Butyl 4-(4-((4-(4-(2-dioxotetrahydropyrimidin-1(2H)-yl)-1H-indazol-1-yl)piperidin-1-yl)methyl)-4-hydroxypiperidin-1-yl)-3-fluorobenzoate (D80)

To a flask containing 1-(1-(1-((4-hydroxypiperidin-4-yl)methyl)piperidin-4-yl)-1H-indazol-4-yl)dihydropyrimidine-2,4(1H,3H)-dione trihydrochloride (may be prepared as described in Description 79, 275 mg, 513 μmol) and tert-butyl 3,4-difluorobenzoate (may be prepared as described in Description 1, 132 mg, 616 μmol) was added DMSO (5 mL) and potassium carbonate (355 mg, 2.57 mmol) then the mixture heated at 100° C. for 3 h. The mixture was poured into water (200 mL), then the suspension was extracted with EtOAc (2×50 mL). The organic layers were combined, dried using a hydrophobic frit and evaporated in vacuo. The sample was purified by silica chromatography (24 g) using a 0-100% OAc-cyclohexane gradient over 10 column volumes, followed by a 0-25% ethanol-EtOAc gradient over 10 column volumes. The appropriate fractions were combined and evaporated in vacuo to give the required product (119 mg, 37% yield) as a white solid. LCMS (high pH A): Rt=1.32 min, MH+=621.

Description 81

4-(4-((4-(4-(2,4-Dioxotetrahydropyrimidin-1(2H)-yl)-1H-indazol-1-yl)piperidin-1-yl)methyl)-4-hydroxypiperidin-1-yl)-3-fluorobenzoic Acid Bis-Trifluoroacetic Acid Salt (D81)

tert-Butyl 4-(4-((4-(4-(2,4-dioxotetrahydropyrimidin-1(2H)-yl)-1H-indazol-1-yl)piperidin-1-yl)methyl)-4-hydroxypiperidin-1-yl)-3-fluorobenzoate (may be prepared as described in Description 80, 119 mg, 192 μmol) was dissolved in TFA (2 mL) then the mixture was stirred at room temperature for 10 min. The mixture was diluted with DCM (10 mL) and concentrated in vacuo. The residue was azeotroped with further DCM (10 mL), then sonicated in diethyl ether (10 mL) causing solid precipitation. The solid was collected and dried under vacuum to give the required product (154 mg, quantitative yield) as an off-white solid. LCMS (high pH A) Rt=0.66 min, MH+=565.

Description 82

Ethyl 3-fluoro-4-(2-oxo-7-azaspiro[3.5]nonan-7-yl)benzoate (D82)

To a solution of ethyl 3,4-difluorobenzoate (1.00 g, 5.37 mmol) in DMSO (10 mL) was added 7-azaspiro[3.5]nonan-2-one hydrochloride (944 mg, 5.37 mmol) and $K_2CO_3$ (2.23 g, 16.1 mmol) then the reaction mixture was heated to 110° C. for 16 h. The reaction mixture was diluted with water (10 ml) and extracted with EtOAc (2×20 ml). The organic layers were combined, dried over sodium sulfate, filtered and concentrated in vacuo. The sample was purified by silica chromatography (25 g) using a 20-30% EtOAc/petroleum ether gradient. The appropriate fractions were combined and evaporated in vacuo to give the required product (500 mg, 30% yield) as an off-white solid. LCMS (formic A): Rt=1.17 min, MH+=306.

Description 83

3-Fluoro-4-(2-oxo-7-azaspiro[3.5]nonan-7-yl)benzoic Acid (D83)

To a solution of ethyl 3-fluoro-4-(2-oxo-7-azaspiro[3.5]nonan-7-yl)benzoate (may be prepared as described in Description 82, 600 mg, 1.97 mmol) in MeOH (6 mL) was added a solution of NaOH (2M aq., 1.97 mL, 3.93 mmol) in water (2 mL), then the mixture was stirred at room temperature for 16 h. The reaction mixture was concentrated and acidified with HCl (1.5M aq.) to pH ~2, then the resulting precipitate was separated by filtration and dried. filtered and dried to give the required product (500 mg, 90% yield) as pale brown liquid. LCMS (formic A): Rt=0.90 min, MH+=278.

Description 84

N-((1r,3r)-3-((8-Cyanoquinolin-5-yl)oxy)-2,2,4,4-tetramethylcyclobutyl)-3-fluoro-4-(2-oxo-7-azaspiro[3.5]nonan-7-yl)benzamide (D84)

To a solution of 3-fluoro-4-(2-oxo-7-azaspiro[3.5]nonan-7-yl)benzoic acid (may be prepared as described in Description 83, 300 mg, 1.08 mmol) in DMF (0.5 mL) was added DIPEA (565 μL, 3.25 mmol), 5-((1r,3r)-3-amino-2,2,4-trimethylcyclobutoxy)quinoline-8-carbonitrile (may be prepared as described in Description 49, 335 mg, 1.19 mmol) then HATU (494 mg, 1.30 mmol) then the reaction mixture was stirred at rt for 16 h. The reaction mixture was diluted with water (10 mL) and extracted with EtOAc (2×10 mL). The organic layers were combined, dried over sodium sulfate, filtered and concentrated in vacuo. In a separate flask, to a solution of 3-fluoro-4-(2-oxo-7-azaspiro[3.5]nonan-7-yl)benzoic acid (may be prepared as described in Description 75, 100 mg, 361 μmol) in DMF (0.5 mL) was added 5-((1r,3r)-3-amino-2,2,4-trimethylcyclobutoxy)quinoline-8-carbonitrile (112 mg, 397 μmol), DIPEA (188 μL, 1.08 mmol) then HATU (165 mg, 433 μmol) then the mixture stirred at rt for 16 h. The reaction mixture was diluted with water (5 mL) then extracted with EtOAc (3×15 mL). The organic layers were combined, washed sequentially with water (2×10 mL) and brine (10 mL), dried over sodium sulfate, filtered and concentrated in vacuo. Both samples were combined to give the required product (300 mg, 37% yield based on combined batches) as an off-white solid. LCMS (formic A): Rt=1.27 min, MH+=555.

Description 85 tert-Butyl ((1r,3r)-3-((5-chloro-6-cyanopyridin-3-yl)oxy)-2,2,4,4-tetramethylcyclobutyl)carbamate (D85)

A stirred solution of tert-butyl ((1r,3r)-3-hydroxy-2,2,4,4-tetramethylcyclobutyl)carbamate (3.00 g, 12.3 mmol) in DMF (41 mL) was cooled in an ice-water bath, then sodium hydride (592 mg, 60% w/w, 14.8 mmol) was added then the reaction mixture was stirred at room temperature for 40 min. The mixture was cooled to 0° C. then 3-chloro-5-fluoropicolinonitrile (2.12 g, 13.6 mmol) was added, then the ice bath was removed and the mixture stirred at room temperature for 22.5h. The solution was partially concentrated in vacuo to one third of its initial volume. $NH_4Cl$ (sat. aq., 50 ml) was added and extracted with EtOAc (3×70 ml). The combined organic layers were washed with brine and then dried over $Na_2SO_4$, filtered and the solvent removed under reduced pressure. The sample was purified by chromatography on Si (120 g) using a 15-100% EtOAc-cyclohexane gradient. The appropriate fractions were combined and evaporated in vacuo to give the desired product (2.90 g, 59% yield) as white solid. LCMS (formic A): Rt=0.91 min, $MH^+$=380.

Description 86

5-((1r,3r)-3-Amino-2,2,4,4-tetramethylcyclobutoxy)-3-chloropicolinonitrile Dihydrochloride (D86)

To a stirred solution of tert-butyl ((1r,3r)-3-((5-chloro-6-cyanopyridin-3-yl)oxy)-2,2,4,4-tetramethylcyclobutyl)carbamate (may be prepared as described in Description 85; 2.88 g, 7.58 mmol) in DCM (75 mL) was added HCl (4M in dioxane, 19.0 mL, 75.8 mmol) at 0° C., then the mixture was stirred at room temperature for 18 hours. The reaction mixture was concentrated in vacuo to give the desired product (2.40 g, 85% yield) as a white solid. LCMS (formic A): Rt=0.76 min, $MH^+$=280.

Description 87

Benzyl 4-(4-amino-6-fluoro-1H-indazol-1-yl)piperidine-1-carboxylate (D87)

6-Fluoro-1H-indazol-4-amine (3 g, 19.85 mmol) and DMF (30 mL) were mixed and stirred at room temperature, treated with NaH (1.588 g, 39.7 mmol), stirred 15 min, then benzyl 4-((methylsulfonyl)oxy)piperidine-1-carboxylate (6.22 g, 19.8 mmol) and heated to 80° C. After approximately 1 h benzyl 4-((methylsulfonyl)oxy)piperidine-1-carboxylate (6.22 g, 19.8 mmol) was added. After an additional 1 h, benzyl 4-((methylsulfonyl)oxy)piperidine-1-carboxylate (6.22 g, 19.8 mmol) was added and the reaction mixture heated to 80° C. for 3 h. The reaction mixture was diluted with EtOAc and $NH_4Cl$, washed with brine (twice), dried ($MgSO_4$), filtered, evaporated in vacuo and purified by flash column chromatography (120 g, silica, 0-70% EtOAc/cyclohexane) to give after evaporation of the fractions the title compound as a colourless gum (2.1 g, 5.70 mmol, 29% yield). LCMS (high pH A): Rt=1.11 min, $MH^+$=369.2.

Description 88

1-(6-Fluoro-1-(piperidin-4-yl)-1H-indazol-4-yl)dihydropyrimidine-2,4(1H,3H)-dione (D88)

Benzyl 4-(4-amino-6-fluoro-1H-indazol-1-yl)piperidine-1-carboxylate (may be prepared as described in Description 87; 2.1 g, 5.70 mmol) and acrylic acid (1.17 mL, 17.1 mmol) stirred overnight (approximately 16 h) at 60° C. An additional 1 equivalent of acrylic acid was added and the reaction mixture heated at 80° C. for 2 h. The reaction mixture was concentrated under a stream of nitrogen, then taken up in Acetic Acid (10 mL), treated with urea (1.712 g, 28.5 mmol) and heated at 135° C. overnight (approximately 16 h). The reaction mixture was concentrated, partitioned between EtOAc and water. The organic phase was washed with water, sodium bicarbonate solution and brine, dried ($MgSO_4$), filtered and evaporated in vacuo to give a pale brown oil. Purification by flash column chromatography (Silica, 120 g, 30-90% EtOAc/cyclohexane) gave after evaporation of the fractions benzyl 4-(4-(2,4-dioxotetrahydropyrimidin-1(2H)-yl)-6-fluoro-1H-indazol-1-yl)piperidine-1-carboxylate as an impure off-white solid. This was dissolved in ethanol (20 mL), treated with ammonium formate (0.813 g, 12.89 mmol) and Pd—C (10%) (0.137 g, 1.289 mmol) and refluxed under nitrogen for 40 mins. The reaction mixture was cooled, filtered through celite, washing with methanol and acetonitrile and evaporated in vacuo to give a pink collapsed foam. Purification by reverse phase (C18) chromatography using a 0-25% acetonitrile-water (10 mM ammonium bicarbonate modifier) gradient gave the title compound as a collapsed white foam (220 mg, 0.63 mmol, 49% yield). LCMS (high pH): Rt=0.63 min, $MH^+$=332.1.

Description 89 tert-Butyl 4-(5-fluoro-4-Iodo-1H-indol-1-yl)piperidine-1-carboxylate (D89)

5-Fluoro-4-iodo-1H-indole (2.7 g, 10.34 mmol), tert-butyl 4-hydroxypiperidine-1-carboxylate (4.16 g, 20.69 mmol) and (triphenylphosphoranylidene)acetonitrile (6.23 g, 20.69 mmol) in toluene (30 ml) were stirred at 110° C. for 64 h. The reaction was allowed to cool to room temperature, and was evaporated in vacuo. The residue was loaded in DCM (10 mL) and purified on a 120 g silica cartridge using a gradient of 0-60% EtOAc in cyclohexane to give a yellow gum. This material was loaded in DCM (6 mL) and purified on a 55 g aminopropyl ($NH_2$) cartridge using a gradient of 0-50% EtOAc in cyclohexane to give tert-butyl 4-(5-fluoro-4-iodo-1H-indol-1-yl)piperidine-1-carboxylate (1.16 g, 2.61 mmol, 25.2% yield). LCMS (formic A): Rt=1.50 min, M-$tBu^+$=399

Description 90 tert-Butyl 4-(4-(2,4-dioxo-3-((2-(trimethylsilyl)ethoxy)methyl)tetrahydropyrimidin-1(2H)-yl)-5-fluoro-1H-indol-1-yl)piperidine-1-carboxylate (D90)

A mixture of copper(I) iodide (0.075 g, 0.392 mmol), potassium carbonate (0.722 g, 5.22 mmol), 3-((2-(trimethylsilyl)ethoxy)methyl)dihydropyrimidine-2,4(1H,3H)-dione (may be prepared as described in Description 4; 0.766 g, 3.13 mmol) and tert-butyl 4-(5-fluoro-4-iodo-1H-indol-1-yl)piperidine-1-carboxylate (may be prepared as described in Description 89; 1.16 g, 2.61 mmol) was suspended in anhydrous 1,4-dioxane (15 mL). trans-N,N'-Dimethylcyclohexane-1,2-diamine (0.124 mL, 0.783 mmol) was added, and the flask was evacuated and purged with nitrogen (×3). The mixture was stirred at 140° C. After 18 h, the reaction was allowed to cool to room temperature, and additional copper(I) iodide (0.075 g, 0.392 mmol), trans-N,N'-dimethylcyclohexane-1,2-diamine (0.124 mL, 0.783 mmol) and 3-((2-(trimethylsilyl)ethoxy)methyl)dihydropyrimidine-2,4(1H,3H)-dione (1.2 g) were added. The flask was evacuated and purged with nitrogen (×3), and the mixture was stirred at 140° C. After 24 h, the reaction was allowed to cool to RT and was diluted with EtOAc (25 mL). The organic was washed sequentially with water (25 mL) and brine (25 mL), and then passed through a hydrophobic frit. The filtrate was evaporated in vacuo and the residue loaded in DCM (5 mL) and purified on an 80 g silica cartridge using a gradient of 0-80% EtOAc in cyclohexane to give tert-butyl 4-(4-(2,4-dioxo-3-((2-(trimethylsilyl)ethoxy)methyl)tetrahydropyrimidin-1(2H)-yl)-5-fluoro-1H-indol-1-yl)piperidine-1-carboxylate (96 mg, 0.171 mmol, 6.56% yield). LCMS (high pH A): Rt=1.45 min, $MH^+$=561

Description 91

1-(5-Fluoro-1-(piperidin-4-yl)-1H-indol-4-yl)dihydropyrimidine-2,4(1H,3H)-dione (D91)

tert-Butyl 4-(4-(2,4-dioxo-3-((2-(trimethylsilyl)ethoxy)methyl)tetrahydropyrimidin-1(2H)-yl)-5-fluoro-1H-indol-1-yl)piperidine-1-carboxylate (may be prepared as described in Description 90; 96 mg, 0.171 mmol) in DCM (0.50 mL) was treated with TFA (0.20 mL, 2.60 mmol). After 3 h, the reaction was evaporated under a stream of nitrogen, and the residue was dissolved in methanol (0.50 mL). 4 M Ammonia in methanol (0.111 mL, 5.14 mmol) was added, and after 1 h, the reaction was evaporated under a stream of nitrogen. The residue purified by reverse phase flash chromatography on a 30 g C18 cartridge eluting with a 0-55% gradient of acetonitrile (containing 1% 0.88 $NH_{3(aq)}$) and 10 mM ammonium carbonate in water adjusted to pH 10 with ammonia to give 1-(5-Fluoro-1-(piperidin-4-yl)-1H-indol-4- yl)dihydropyrimidine-2,4(1H,3H)-dione (30 mg, 0.091 mmol). LCMS (high pH A): Rt=0.70 min, $MH^+$=331

Description 92 tert-Butyl 4-(4-bromo-5-fluoro-1H-indazol-1-yl) piperidine-1-carboxylate (D92)

A mixture of 4-bromo-5-fluoro-1H-indazole (1.5 g, 6.98 mmol), tert-butyl 4-((methylsulfonyl)oxy)piperidine-1-carboxylate (2.4 g, 8.59 mmol) and cesium carbonate (3.41 g, 10.46 mmol) in anhydrous DMF (30 mL) was stirred at 60° C. for 5 h. More tert-butyl 4-((methylsulfonyl)oxy)piperidine-1-carboxylate (0.6 g) was added, and the mixture was stirred under nitrogen at 60° C. for 18 h. The reaction was allowed to cool to room temperature and was diluted with EtOAc (50 mL). The solution was washed sequentially with LiCl (5% aq., 2×50 mL) and brine (50 mL). The organic layer was passed through a hydrophobic frit and the filtrate evaporated in vacuo. The resulting oil was loaded in DCM (5 mL) and purified on a 120 g silica cartridge using a gradient of 0-60% EtOAc in cyclohexane to give tert-butyl 4-(4-bromo-5-fluoro-1H-indazol-1-yl)piperidine-1-carboxylate (1.47 g, 3.69 mmol, 52.9% yield). LCMS (formic A): Rt=1.41 min, M-$tBu^+$=342, 344

Description 93 tert-Butyl 4-(4-(2,4-dioxo-3-((2-(trimethylsilyl) ethoxy)methyl)tetrahydropyrimidin-1(2H)-yl)-5-fluoro-1H-indazol-1-ylpiperidine-1-carboxylate (D93)

A mixture of copper(I) iodide (0.105 g, 0.554 mmol), potassium carbonate (1.02 g, 7.38 mmol), 3-((2-(trimethylsilyl)ethoxy)methyl)dihydropyrimidine-2,4(1H,3H)-dione (may be prepared as described in Description D4; 1.13 g, 4.62 mmol) and tert-butyl 4-(4-bromo-5-fluoro-1H-indazol-1-yl)piperidine-1-carboxylate (may be prepared as described in Description 92; 1.47 g, 3.69 mmol) was suspended in anhydrous 1,4-dioxane (20 mL). trans-N,N'-Dimethylcyclohexane-1,2-diamine (0.175 mL, 1.107 mmol) was added, and the vessel was sealed, evacuated and purged with nitrogen (×3). The mixture was stirred at 140° C. for 23 h. The reaction was allowed to cool to room temperature, the suspension filtered through Celite, and the Celite washed with EtOAc (10 mL). The filtrate was evaporated in vacuo and the residue loaded in DCM (5 mL) and purified on an 80 g silica cartridge using a gradient of 0-80% EtOAc in cyclohexane to give tert-butyl 4-(4-(2,4-dioxo-3-((2-(trimethylsilyl)ethoxy)methyl)tetrahydropyrimidin-1(2H)-yl)-5-fluoro-1H-indazol-1-yl)piperidine-1-carboxylate (961 mg, 1.711 mmol, 46.4% yield). LCMS (formic A): Rt=1.39 min, M-$C_6H_{12}^+$=478

Description 94

1-(5-Fluoro-1-(piperidin-4-yl)-1H-indazol-4-yl)dihydropyrimidine-2,4(1H,3H)-dione (D94)

A solution of tert-butyl 4-(4-(2,4-dioxo-3-((2-(trimethylsilyl)ethoxy)methyl)tetrahydropyrimidin-1(2H)-yl)-5-fluoro-1H-indazol-1-yl)piperidine-1-carboxylate (may be prepared as described in Description 93; 957 mg, 1.704 mmol) in DCM (8 mL) was treated with TFA (2.0 mL, 26.0 mmol) and left to stand in a stoppered vessel for 3 h. The mixture was evaporated in vacuo and the residue dissolved in methanol (8.00 mL) and treated with 4 M ammonia in methanol (12 mL, 48.0 mmol). The solution was stirred in a stoppered vessel at room temperature for 1 h and evaporated in vacuo. The gum was loaded and preabsorbed on Florisil (from methanol) and purified on a 24 g silica cartridge using a gradient of 0-20% methanol in DCM (containing 1% triethylamine) to give partially pure product. This material was purified by MDAP (high pH) to give 1-(5-fluoro-1-(piperidin-4-yl)-1H-indazol-4-yl)dihydropyrimidine-2,4(1H,3H)-dione (62 mg, 0.187 mmol, 11% yield). LCMS (high pH A): Rt=0.63 min, $MH^+$=332

Description 95

Benzyl 4-(4-bromoindolin-1-yl)piperidine-1-carboxylate (D95)

Benzyl 4-oxopiperidine-1-carboxylate (8 g, 34.3 mmol) and 4-bromoindoline (6 g, 30.3 mmol) were dissolved in acetic acid (100 mL) and stirred for 1 h, then cooled in an ice bath and sodium triacetoxyborohydride (12.84 g, 60.6 mmol) was added. The mixture was stirred for 18 h, then evaporated to about half its original volume, diluted with water (200 mL) and extracted with EtOAc (2×200 mL). The combined organics were washed with water and sodium bicarbonate solution (200 mL of each) and then dried and evaporated in vacuo to give the title compound as a pale yellow gum (16.0 g) which was used in the next step without purification. LCMS (high pH A): Rt=1.52 min, $MH^+$=415.1, 417.1

Description 96

Benzyl 4-(4-bromo-1H-indol-1-yl)piperidine-1-carboxylate (D96)

Benzyl 4-(4-bromoindolin-1-yl)piperidine-1-carboxylate (may be prepared as described in Description 95; 20 g, 38.5 mmol; crude, assumed to be 80% pure) was dissolved in THF (60 mL) and cooled in an ice bath, then DDQ (8.74 g, 38.5 mmol) was added and the mixture stirred for 10 min, then allowed to warm to room temperature. The mixture was diluted with EtOAc (200 mL) and washed with sodium bicarbonate solution (200 mL), then with 1 M NaOH (200 mL) and the organic layer dried and evaporated in vacuo to give a dark brown gum. The crude product was dissolved in DCM and loaded onto a 330 g silica column, then eluted with 0-50% MTBE/cyclohexane and product-containing fractions evaporated in vacuo to give the title compound (15.7 g, 38.0 mmol, 99% yield) as a pale yellow gum. LCMS (high pH A): Rt=1.52 min, $MH^+$=413.1, 415.1.

Description 97

Benzyl 4-(4-(2,4-dioxo-3-((2-(trimethylsilyl)ethoxy) methyl)tetrahydropyrimidin-1(2H)-yl)-1H-indol-1-yl)piperidine-1-carboxylate (D97)

To BrettPhos Pd G3 (1.162 g, 1.282 mmol), BrettPhos (0.688 g, 1.282 mmol) 3-((2-(trimethylsilyl)ethoxy)methyl) dihydropyrimidine-2,4(1H,3H)-dione (may be prepared as described in Description 4; 4 g, 16.37 mmol) and potassium phosphate tribasic (6.80 g, 32.1 mmol) was added a solution of benzyl 4-(4-bromo-1H-indol-1-yl)piperidine-1-carboxylate (may be prepared as described in Description 96; 5.3 g, 12.82 mmol) in 1,4-dioxane (100 mL). The reaction mixture was degassed (vacuum/nitrogen ×3) and then heated under nitrogen to 100° C. for 18 h. The reaction mixture was allowed to cool. The mixture was diluted with EtOAc and filtered through a pad of celite. The pad was washed with EtOAc. The combined filtrate and washings were evaporated in vacuo. The residue was dissolved in DCM and applied to a 330 g silica cartridge. This was eluted with a gradient of 0-60% EtOAc in cyclohexane over 30 min. The required fractions were combined and evaporated in vacuo to give the title compound (5.61 g, 9.73 mmol, 76% yield). LCMS (high pH A): Rt=1.44 min, $MH^+$=577.1

Description 98

Benzyl 4-(4-(2,4-dioxotetrahydropyrimidin-1(2H)-yl)-1H-indol-1-yl)piperidine-1-carboxylate (D98)

Benzyl 4-(4-(2,4-dioxo-3-((2-(trimethylsilyl)ethoxy)methyl)tetrahydropyrimidin-1(2H)-yl)-1H-indol-1-yl)piperidine-1-carboxylate (may be prepared as described in Description 97; 7.6 g, 13.18 mmol) was dissolved in DCM (30 mL) and cooled to 0° C. in an ice bath, then TFA (10 mL, 130 mmol) was added and the mixture was stirred for 2 h, then evaporated in vacuo to give a brown oil. This was suspended in methanol (30 ml) and treated with SG0.88 ammonium hydroxide (20 mL) and stirred for 10 min, then diluted with DCM (100 mL) and washed with saturated sodium bicarbonate solution. The organic layer was dried and evaporated in vacuo to give a beige solid. The crude was dissolved in DCM and loaded onto a 120 g silica column, then eluted with 0-100% EtOAc/cyclohexane and product-containing fractions evaporated in vacuo to give the tide compound as a colourless solid (5.23 g, 11.71 mmol, 89% yield). LCMS (high pH A): Rt=1.07 min, $MH^+$=447.2.

Description 99

1-(1-(Piperidin-4-yl)-1H-indol-4-yl)dihydropyrimidine-2,4(1H,3H)-dione (D99)

Batch 1

Benzyl 4-(4-(2,4-dioxotetrahydropyrimidin-1(2H)-yl)-1H-indol-1-yl)piperidine-1-carboxylate (may be prepared as described in Description 98; 2.75 g, 6.16 mmol) was dissolved in a mixture of methanol (50 mL) and EtOAc (50.0 mL), then ammonium formate (0.388 g, 6.16 mmol) and Pd—C 10% on Carbon (0.655 g, 6.16 mmol) were added and the mixture was heated at reflux for 1 h. The mixture was cooled and filtered through Celite, the Celite pad washed with 1:1 DCM/methanol (50 mL) and the filtrate evaporated in vacuo to give Batch 1 of the title compound (1.67 g).

Batch 2

Benzyl 4-(4-(2,4-dioxotetrahydropyrimidin-1(2H)-yl)-1H-indol-1-yl)piperidine-1-carboxylate (may be prepared as described in Description 98; 5.2 g, 11.65 mmol) was dissolved in a mixture of methanol (200 mL) and EtOAc (50 mL) and Pd—C 10% on Carbon (1.239 g, 11.65 mmol) and ammonium formate (3.67 g, 58.2 mmol) were added, then the mixture was heated at reflux for 30 min, cooled and filtered through Celite. The Celite pad was washed with 1:1 DCM/methanol (50 mL) and the filtrate evaporated in vacuo to give Batch 2 of the title compound (3.35 g). the two batches were combined and triturated with MTBE (30 mL), then filtered to give the title compound as a colourless solid (4.48 g, 14.34 mmol, 80% overall yield).

Description 100 tert-Butyl 4-(4-bromo-1H-pyrrolo[3,2-c]pyridin-1-yl)piperidine-1-carboxylate (D100)

To 4-bromo-1H-pyrrolo[3,2-c]pyridine (2 g, 10.15 mmol) in DMF (30 mL) was added NaH (0.812 g, 20.30 mmol). After 15 min, one-third of the tert-butyl 4-((methylsulfonyl)oxy)piperidine-1-carboxylate (8.51 g, 30.5 mmol) was added, and the reaction was heated to 80° C. At approximately 1 h intervals, the remaining ⅔ tert-butyl 4-((methylsulfonyl)oxy)piperidine-1-carboxylate was added, and the mixture was stirred for 3 h, then allowed to cool over the weekend (approximately 60 h). The reaction was diluted with $NH_4Cl$ solution and EtOAc, washed with brine (×2), dried ($MgSO_4$), filtered and evaporated in vacuo to give a thick oil. This material was purified over a silica 220 g column, eluting with 0-100% EtOAc in cyclohexane to give partially pure product. This material was repurified over a silica 220 g column, eluting with 0-30% diethyl ether in DCM to give the title compound (3.1 g, 7.74 mmol, 76% yield). LCMS (high pH A): Rt=1.21 min, $MH^+$=381.9

Description 101 tert-Butyl 4-(4-(2,4-dioxo-3-((2-(trimethylsilyl)ethoxy)methyl)tetrahydropyrimidin-1(2H)-yl)-1H-pyrrolo[3,2-c]pyridin-1-yl)piperidine-1-carboxylate (D101)

A mixture of 3-((2-(trimethylsilyl)ethoxy)methyl)dihydropyrimidine-2,4(1H,3H)-dione (may be prepared as described in Description D4; 1.671 g, 6.84 mmol) tert-butyl 4-(4-bromo-1H-pyrrolo[3,2-c]pyridin-1-yl)piperidine-1-carboxylate (may be prepared as described in Description 100; 2 g, 5.26 mmol) potassium carbonate (2.181 g, 15.78 mmol) trans-N,N'-dimethylcyclohexane-1,2-diamine (0.249 mL, 1.578 mmol) and copper(I) iodide (0.150 g, 0.789 mmol) in anhydrous 1,4-dioxane (12 mL) was degassed with vacuum/$N_2$ several times, then heated at 135° C. in a sealed tube overnight (ca 16 h). the reaction was cooled, diluted with water, extracted with EtOAc, washed with brine twice, dried, filtered and evaporated in vacuo to give a pale brown oil which was purified over a silica 120 g column, eluting with 50-100% EtOAc in cyclohexane to give tert-butyl 4-(4-(2,4-dioxo-3-((2-(trimethylsilyl)ethoxy)methy)tetrahydropyrimidin-1(2H)-yl)-1H-pyrrolo[3,2-c]pyridin-1-yl)piperidine-1-carboxylate (1.8 g, 3.14 mmol, 59.8% yield). LCMS (high pH A): Rt=1.34 min, $MH^+$=544.3

Description 102 tert-Butyl 4-(4-bromo-1H-pyrrolo[2,3-b]pyridin-1-yl)piperidine-1-carboxylate (D102)

To tert-butyl 4-hydroxypiperidine-1-carboxylate (3.89 g, 19.34 mmol), $PPh_3$ (3.38 g, 12.89 mmol) and 4-bromo-1H-pyrrolo[2,3-b]pyridine (1.27 g, 6.45 mmol) in THF (30 mL) at 0° C. was added, dropwise over about 10 min, DIAD (2.506 mL, 12.89 mmol), and the reaction was stirred vigorously while warming to room temperature overnight (approximately 16 h). The mixture was evaporated in vacuo and purified over a silica, eluting with 0-30% EtOAc in cyclohexane) to give tert-butyl 4-(4-bromo-1H-pyrrolo[2,3-b]pyridin-1-yl)piperidine-1-carboxylate (1.3 g, 3.25 mmol, 50.4% yield). LCMS (high pH A): Rt=1.39 min, $MH^+$=382.0

Description 103 tert-Butyl 4-(4-(2,4-dioxo-3-((2-(trimethylsilyl)ethoxy)methyl)tetrahydropyrimidin-1(2H)-yl)-1H-pyrrolo[2,3-b]pyridin-1-yl)piperidine-1-carboxylate (D233)

A mixture of 3-((2-(trimethylsilyl)ethoxy)methyl)dihydropyrimidine-2,4(1H,3H)-dione (may be prepared as described in Description 4; 1.086 g, 4.44 mmol) tert-butyl 4-(4-bromo-1H-pyrrolo[2,3-b]pyridin-1-yl)piperidine-1-carboxylate (may be prepared as described in Description 102; 1.3 g, 3.42 mmol), potassium carbonate (0.945 g, 6.84 mmol), trans-N,N'-dimethylcyclohexane-1,2-diamine (0.162 mL, 1.026 mmol) and copper(I) iodide (0.098 g, 0.513 mmol) in anhydrous 1,4-dioxane (13 mL) was degassed with vacuum/$N_2$ several times, then heated at 135° C. in a sealed tube overnight (approximately 16 h). the reaction was cooled, diluted with water, extracted with EtOAc, washed with brine twice, dried, filtered and evaporated in vacuo to give a pale brown oil which was purified over a silica 80 g column, eluting with 50-100% EtOAc in cyclohexane to give tert-butyl 4-(4-(2,4-dioxo-3-((2-(trimethylsilyl)ethoxy)methyl)tetrahydropyrimidin-1(2H)-yl)-1H-pyrrolo[2,3-b]pyridin-1-yl)piperidine-1-carboxylate (1.4 g, 2.446 mmol, 71.6% yield). LCMS (high pH A): Rt=1.36 min, $MH^+$=544.4

Description 104

1-(1-(Piperidin-4-yl)-1H-pyrrolo[3,2-c]pyridin-4-yl)dihydropyrimidine-2,4(1H,3H)-dione (D104)

To tert-butyl 4-(4-(2,4-dioxo-3-((2-(trimethylsilyl)ethoxy)methyl)tetrahydropyrimidin-1(2H)-yl)-1H-pyrrolo[3,2-c]pyridin-1-yl)piperidine-1-carboxylate (may be prepared as described in Description 101; 1.8 g, 3.31 mmol) in DCM (1 mL) was added TFA (5.10 mL, 66.2 mmol). After 1 h the reaction was blown down and held under high vacuum, then treated with 4M $NH_3$ in methanol (10 ml). After 1 h, the mixture was blown down, and the resulting white solid was dissolved in warm DMSO (4 ml) and purified by flash chromatography (C18-silica, 100 g), eluting with 0-25% acetonitrile-water (10 mM ammonium bicarbonate modifier) gradient to give 1-(1-(piperidin-4-yl)-1H-pyrrolo[3,2-c]pyridin-4-yl)dihydropyrimidine 2,4(1H,3H)-dione (0.9 g, 2.73 mmol, 82% yield). LCMS (high pH A): Rt=0.54 min, $MH^+$=314.1

Description 105

1-(1-(Piperidin-4-yl)-1H-pyrrolo[2,3-b]pyridin-4-yl)dihydropyrimidine-2,4(1H,3H)-dione (D105)

To tert-butyl 4-(4-(2,4-dioxo-3-((2-(trimethylsilyl)ethoxy)methyl)tetrahydropyrimidin-1(2H)-yl)-1H-pyrrolo[2,3-b]pyridin-1-yl)piperidine-1-carboxylate (may be prepared as described in Description 103; 1.4 g, 2.57 mmol) in DCM (1 mL) was added TFA (3.97 mL, 51.5 mmol). After 1 h the reaction was blown down and held under high vacuum, then treated with 4M $NH_3$ in methanol (10 ml). After 1 h, the mixture was blown down, then treated with 4M $NH_3$ in methanol (10 ml) and stirred 1 h. The resulting white solid was collected by filtration and washed with a small amount of methanol and ether, then dried in vacuo to give 1-(1-(piperidin-4-yl)-1H-pyrrolo[2,3-b]pyridin-4-yl)dihydropyrimidine-2,4(1H,3H)-dione (0.7 g, 2.122 mmol, 82% yield). LCMS (high pH A): Rt=0.54 min, $MH^+$=314.1

Description 106

Benzyl 4-(4-bromo-1H-pyrazolo[3,4-b]pyridin-1-yl)piperidine-1-carboxylate (D106)

4-Bromo-1H-pyrazolo[3,4-b]pyridine (3 g, 15.15 mmol) in DMF (30 mL) was stirred at room temperature, treated with NaH (1.212 g, 30.3 mmol), stirred 15 min, treated with one-third of the portion of benzyl 4-((methylsulfonyl)oxy)piperidine-1-carboxylate (14.24 g, 45.4 mmol) and heated to 80° C. At approximately 1 h intervals, the remaining ⅔ benzyl 4-((methylsulfonyl)oxy)piperidine-1-carboxylate was added. After 4 h the reaction was allowed to cool overnight (about 16 h) and allowed to stand for about two weeks. The reaction was diluted with EtOAc and $NH_4Cl$, washed with brine (×2), dried, filtered, evaporated in vacuo and purified by flash chromatography (120 g, silica, 0-70% EtOAc in cyclohexane) to give benzyl 4-(4-bromo-1H-pyrazolo[3,4-b]pyridin-1-yl)piperidine-1-carboxylate (1.3 g, 2.82 mmol, 18.60% yield). LCMS (high pH A): Rt=1.34 min, $MH^+$=417

Description 107

Benzyl 4-(4-(2,4-dioxotetrahydropyrimidin-1(2H)-yl)-1H-pyrazolo[3,4-b]pyridin-1-yl)piperidine-1-carboxylate (D107)

3-((2-(Trimethylsilyl)ethoxy)methyl)dihydropyrimidine-2,4(1H,3H)-dione (may be prepared as described in Description 4; 0.994 g, 4.07 mmol), benzyl 4-(4-bromo-1H-pyrazolo[3,4-b]pyridin-1-yl)piperidine-1-carboxylate (may be prepared as described in Description 106; 1.3 g, 3.13 mmol), potassium carbonate (0.865 g, 6.26 mmol), trans-N,N'-dimethylcyclohexane-1,2-diamine (0.148 mL, 0.939 mmol) and copper(I) iodide (0.089 g, 0.470 mmol) in dioxane (13 mL) were mixed, degassed with vacuum/$N_2$ several times, then heated at 135° C. in a sealed tube overnight (approximately 16 h). The reaction was cooled, diluted with water, extracted with EtOAc, washed with brine twice, dried, filtered and evaporated in vacuo to give a pale brown oil which was taken up in DCM (5.00 mL), treated with TFA (10 ml, 130 mmol) and stirred for 2 h. The reaction was blown down under nitrogen, taken up in 4M $NH_3$-methanol, stirred 1 h, blown down and allowed to stand overnight to give a white solid. The mixture was diluted with water and EtOAc (solid did not dissolve). The EtOAc was evaporated off, and the compound filtered off from the water and dried by suction to give crude benzyl 4-(4-(2,4-dioxotetrahydropyrimidin-1(2H)-yl)-1H-pyrazolo[3,4-b]pyridin-1-yl)piperidine-1-carboxylate (1.2 g, 2.408 mmol, 77% yield). LCMS (high pH A): Rt=0.94 min, $MH^+$=449.2

Description 108

1-(1-(Piperidin-4-yl)-1H-pyrazolo[3,4-b]pyridin-4-yl)dihydropyrimidine-2,4(1H,3H)-dione (D108)

Benzyl 4-(4-(2,4-dioxotetrahydropyrimidin-1(2H)-yl)-1H-pyrazolo[3,4-b]pyridin-1-yl)piperidine-1-carboxylate (may be prepared as described in Description 107; 1 g, 2.230 mmol), ethanol (20 mL) ammonium formate (1.406 g, 22.30 mmol) and Pd—C, 10% (0.237 g, 2.230 mmol) were refluxed under nitrogen for 40 mins. The reaction mixture was cooled and filtered through Celite, washing with DCM and ethanol. The effluent was evaporated in vacuo to give a very insoluble white powder. Very hot DMSO was used to get most of the material into solution, which was purified using MDAP (high pH) to give 1-(1-(piperidin-4-yl)-1H-pyrazolo[3,4-b]pyridin-4-yl)dihydropyrimidine-2,4(1H,3H)-dione (345 mg, 1.010 mmol, 45.3% yield). LCMS (high pH A): Rt=0.51 min, $MH^+$=315.1

Description 109 tert-Butyl 4-(4-bromo-7H-pyrrolo[2,3-d]pyrimidin-7-yl)piperidine-1-carboxylate (D109)

4-Bromo-7H-pyrrolo[2,3-d]pyrimidine (2 g, 10.10 mmol), $Ph_3P$ (5.30 g, 20.20 mmol), tert-butyl 4-hydroxypiperidine-1-carboxylate (6.10 g, 30.3 mmol) and THF (50 ml) were cooled to 0° C. and treated dropwise with diisopropyl azodicarboxylate (3.93 mL, 20.20 mmol) in THF (10 mL). The mixture was allowed to warm to room temperature overnight. The reaction mixture was evaporated in vacuo and purified by flash chromatography on 330 g silica eluting in 0-100% EtOAc in cyclohexane. Evaporation of the fractions gave the title compound as a thick colourless gum (3.5 g, 8.26 mmol, 82% yield). LCMS (high pH A): Rt=1.24 min, $MH^+$=381, 383.

Description 110 tert-Butyl 4-(4-(2,4-dioxo-3-((2-(trimethylsilyl)ethoxy)methyl)tetrahydropyrimidin-1(2H)-yl)-7H-pyrrolo[2,3-d]pyrimidin-7-yl)piperidine-1-carboxylate (D110)

3-((2-(Trimethylsilyl)ethoxy)methyl)dihydropyrimidine-2,4(1H,3H)-dione (may be prepared as described in Description 4; 1.666 g, 6.82 mmol), tert-butyl 4-(4-bromo-7H-pyrrolo[2,3-d]pyrimidin-7-yl)piperidine-1-carboxylate (may be prepared as described in Description 109; 2 g, 5.25 mmol), potassium carbonate (1.450 g, 10.49 mmol), trans-N,N'-dimethylcyclohexane-1,2-diamine (0.248 mL, 1.574 mmol), copper(I) iodide (0.150 g, 0.787 mmol) and anhydrous 1,4-dioxane (12 mL) were mixed, degassed with vacuum/$N_2$ several times, then heated at 135° C. in a sealed tube overnight (approximately 16 h). The reaction mixture was cooled, diluted with water and extracted with EtOAc The organic phase was washed with brine twice, dried, filtered and evaporated in vacuo. The material was purified by flash chromatography on a 80 g silica cartridge eluting in 20-100% EtOAc in cyclohexane. Evaporation of the fractions gave the title compound as a white collapsed foam (1.08 g, 1.884 mmol, 36% yield). LCMS (high pH A): Rt=1.37 min, $MH^+$=545.

Description 111 tert-Butyl 4-(4-bromo-7H-pyrrolo[2,3-d]pyrimidin-7-yl)piperidine-1-carboxylate (D111)

4-Bromo-7H-pyrrolo[2,3-d]pyrimidine (2 g, 10.10 mmol), $Ph_3P$ (5.30 g, 20.20 mmol), tert-butyl 4-hydroxypiperidine-1-carboxylate (6.10 g, 30.3 mmol) and THF (50 ml) were cooled to 0° C. and treated dropwise with diisopropyl azodicarboxylate (3.93 mL, 20.20 mmol) in THF (10 mL). The mixture was allowed to warm to room temperature overnight. The reaction mixture was evaporated in vacuo and purified by flash chromatography on 330 g silica eluting in 0-100% EtOAc in cyclohexane. Evaporation of the fractions gave the title compound as a thick colourless gum (3.5 g, 8.26 mmol, 82% yield). LCMS (high pH A): Rt=1.24 min, $MH^+$=381, 383.

Description 112 tert-Butyl 4-(4-(2,4-dioxo-3-((2-(trimethylsilyl)ethoxy)methyl)tetrahydropyrimidin-1(2H)-yl)-7H-pyrrolo[2,3-d]pyrimidin-7-yl)piperidine-1-carboxylate (D112)

3-((2-(Trimethylsilyl)ethoxy)methyl)dihydropyrimidine-2,4(1H,3H)-dione (may be prepared as described in Description 4; 1.666 g, 6.82 mmol), tert-butyl 4-(4-bromo-7H-pyrrolo[2,3-d]pyrimidin-7-yl)piperidine-1-carboxylate (may be prepared as described in Description 111; 2 g, 5.25 mmol), potassium carbonate (1.450 g, 10.49 mmol), trans-N,N'-dimethylcyclohexane-1,2-diamine (0.248 mL, 1.574 mmol), copper(I) iodide (0.150 g, 0.787 mmol) and anhydrous 1,4-dioxane (12 mL) were mixed, degassed with vacuum/$N_2$ several times, then heated at 135° C. in a sealed tube overnight (approximately 16 h). The reaction mixture was cooled, diluted with water and extracted with EtOAc. The organic phase was washed with brine twice, dried, filtered and evaporated in vacuo. The material was purified by flash chromatography on a 80 g silica cartridge eluting in 20-100% EtOAc in cyclohexane. Evaporation of the fractions gave the title compound as a white collapsed foam (1.08 g, 1.884 mmol, 36% yield). LCMS (high pH A): Rt=1.37 min, $MH^+$=545.

Description 113

1-(7-(Piperidin-4-yl)-7H-pyrrolo[2,3-d]pyrimidin-4-yl)dihydropyrimidine-2,4(1H,3H)-dione (D113)

tert-Butyl 4-(4-(2,4-dioxo-3-((2-(trimethylsilyl)ethoxy)methyl)tetrahydropyrimidin-1(2H)-yl)-7H-pyrrolo[2,3-d]pyrimidin-7-yl)piperidine-1-carboxylate (may be prepared as described in Description 112; 1.04 g, 1.909 mmol) in DCM (1 mL) was treated with TFA (2.94 mL, 38.2 mmol) and stirred, causing the starting material to dissolve. After 1 h, the reaction mixture was blown down and held under high vacuum. The material was treated with 4 M $NH_3$ in methanol (10 mL) and stirred for 1 h. The mixture was blown down and allowed to stand over the weekend (approximately 60 h). The resulting white solid was dissolved in warm DMSO (4 mL) and purified by reverse phase (C18) chromatography on a 100 g C18-silica cartridge eluting with 0-25% acetonitrile-water (10 mM ammonium bicarbonate modifier) gradient. Evaporation of the fractions gave the title compound (520 mg, 1.572 mmol, 82% yield). LCMS (high pH A): Rt=0.52 min, $MH^+$=315.

Description 114

Benzyl 4-(4-bromo-6-fluoro-1H-indol-1-yl)piperidine-1-carboxylate (D114)

A mixture of 4-bromo-6-fluoro-1H-indole (917 mg, 4.28 mmol), benzyl 4-((methylsulfonyl)oxy)piperidine-1-carboxylate (2014 mg, 6.43 mmol) and cesium carbonate (2094 mg, 6.43 mmol) in anhydrous DMF (11 mL), was stirred at 100° C. for 16 h. The reaction mixture was allowed to cool to room temperature and diluted with EtOAc (50 mL). The solution was washed sequentially with water (50 mL), LiCl (5% aq., 50 mL) and brine (50 mL). The organic layer was passed through a hydrophobic frit and the filtrate evaporated in vacuo. The oil (approximately 1.8 g) was purified by reverse phase flash chromatography on a 100 g C18 cartridge eluting with a 30-95% gradient of acetonitrile and 10 mM ammonium carbonate in water adjusted to pH10 with ammonia solution over 22 min using a 60 mL/min flow rate. The appropriate fractions were combined and the solvent removed by rotary evaporation to give the title compound as a dark brown gum (267 mg, 0.619 mmol, 14% yield). LCMS (high pH A): Rt=1.47 min, $MH^+$=431, 433.

Description 115

Benzyl 4-(4-(2,4-dioxo-3-((2-(trimethylsilyl)ethoxy)methyl)tetrahydropyrimidin-1(2H)-yl)-6-fluoro-1H-indol-1-yl)piperidine-1-carboxylate (D115)

A mixture of copper(I) iodide (12 mg, 0.063 mmol), potassium carbonate (170 mg, 1.228 mmol) and 3-((2-(trimethylsilyl)ethoxy)methy)dihydropyrimidine-2,4(1H,3H)-dione (maybe prepared as described in Description 4; 150 mg, 0.614 mmol) was diluted with a solution of benzyl 4-(4-bromo-6-fluoro-1H-indol-1-yl)piperidine-1-carboxylate (may be prepared as described in Description 114; 264 mg, 0.612 mmol) in anhydrous 1,4-dioxane (3.0 mL). Trans-N,N'-Dimethylcyclohexane-1,2-diamine (0.019 mL, 0.123 mmol) was added, the vessel sealed, and evacuated and purged with nitrogen (×3). The mixture was stirred at 140° C. for 4 h. The reaction was allowed to cool to room temperature, the lid removed, and further copper(I) iodide (24 mg) and Trans-N,N'-Dimethylcyclohexane-1,2-diamine (0.019 mL, 0.123 mmol) added. The vial was sealed and evacuated and purged with nitrogen (×3). The mixture was stirred at 140° C. for 16 h. The reaction was allowed to cool to room temperature, the suspension diluted with DCM (5 mL), and passed through a hydrophobic frit. The filtrate was evaporated in vacuo and the residue loaded in DCM (3 mL) and purified on a 24 g silica cartridge using a gradient of 0-75% EtOAc in cyclohexane over 14 column volumes. The appropriate fractions were combined and the solvent evaporated in vacuo to give the title compound as a light brown gum (270 mg, 0.454 mmol, 74% yield). LCMS (high pH A): Rt=1.42 min, M-$C_2H_6^+$ 567.

Description 116

Benzyl 4-(4-(2,4-dioxotetrahydropyrimidin-1(2H)-yl)-6-fluoro-1H-indol-1-yl)piperidine-1-carboxylate (D116)

To benzyl 4-(4-(2,4-dioxo-3-((2-(trimethylsilyl)ethoxy)methyl)tetrahydropyrimidin-(2H)-yl)-6-fluoro-1H-indol-1-yl)piperidine-1-carboxylate (may be prepared as described in Description 115; 5.28 g, 8.88 mmol) in DCM (50 mL) was added trifluoroacetic acid (10.26 mL, 133 mmol). After 3 h the reaction was concentrated and dissolved in methanol (20 mL), followed by the addition of ammonia (7 M in methanol) (25.4 mL, 178 mmol). After 1.5 h, DCM (100 mL) was added, and mixture was diluted with saturated aqueous sodium hydrogen carbonate (75 mL). The layers were separated, and the aqueous layer was extracted with DCM (75 ml). The combined organic layers were filtered through a hydrophobic frit, concentrated, adsorbed onto Florisil and purified using a 120 g silica column, eluting with 50-100% EtOAc in cyclohexane (product eluted at 60-70%) to give benzyl 4-(4-(2,4-dioxotetrahydropyrimidin-1(2H)-yl)-6-fluoro-1H-indol-1-yl)piperidine-1-carboxylate (2.63 g, 5.66 mmol, 63.8% yield). LCMS (high pH A): Rt=1.11 min, $MH^+$=482.2

Description 117

1-(6-Fluoro-1-(piperidin-4-yl)-1H-indol-4-yl)dihydropyrimidine-2,4(1H,3H)-dione (D117)

Benzyl 4-(4-(2,4-dioxotetrahydropyrimidin-1(2H)-yl)-6-fluoro-1H-indol-1-yl)piperidine-1-carboxylate (may be prepared as described in Description 116; 2.63 g, 5.66 mmol) was dissolved in a mixture of ethanol (40 mL) and EtOAc (10.00 mL), and Pd—C 10% (0.603 g, 0.566 mmol) and ammonium formate (1.785 g, 28.3 mmol) were added. The mixture was heated at reflux for 4 h, cooled and filtered through Celite. The celite pad was washed with DCM:ethanol (1:1, 1 L), and the filtrate was evaporated in vacuo to give 1-(6-fluoro-1-(piperidin-4-yl)-1H-indol-4-yl)dihydropyrimidine-2,4(1H,3H)-dione (1.78 g, 5.39 mmol, 95% yield). LCMS (high pH A): Rt=0.69 min, $MH^+$=331.1

Description 118

Benzyl 4-(4-(2,4-dioxo-3-((2-(trimethylsilyl)ethoxy)methyl)tetrahydropyrimidin-1(2H)-yl)-1H-pyrazolo[4,3-c]pyridin-1-yl)piperidine-1-carboxylate (D118)

4-Bromo-1H-pyrazolo[4,3-c]pyridine (2.16 g, 10.91 mmol) and DMF (30 mL) were mixed and stirred at room temperature and treated with 60% NaH (0.873 g, 21.82 mmol). The mixture was stirred for 15 min, treated with benzyl 4-((methylsulfonyl)oxy)piperidine-1-carboxylate (3.14 g, 10.9 mmol) and heated to 80° C. After approximately 1 h, benzyl 4-((methylsulfonyl)oxy)piperidine-1-carboxylate (3.14 g, 10.9 mmol) was added. After an additional 1 h, benzyl 4-((methylsulfonyl)oxy)piperidine-1-carboxylate (3.14 g, 10.9 mmol) was added and the reaction mixture was stirred for 3 h at 80° C. The reaction mixture was diluted with EtOAc and $NH_4Cl$, washed with brine (twice), dried ($MgSO_4$), filtered and evaporated in vacuo. Purification by flash column chromatography (120 g, silica, 0-70% EtOAc/cyclohexane) gave after evaporation of the fractions a mixture of the N1 and N2 alkylated regioisomers as a brown oil (4.3 g). This was mixed with 3-((2-(trimethylsilyl)ethoxy)methy)dihydropyrimidine-2,4(1H,3H)-dione (may be prepared as described in Description 1; 2.78 g, 11.39 mmol) potassium carbonate (2.86 g, 20.71 mmol), trans-N,N'-Dimethylcyclohexane-1,2-diamine (0.490 mL, 3.11 mmol), copper(I) iodide (0.296 g, 1.553 mmol) and anhydrous 1,4-dioxane (45 mL), degassed with vacuum/nitrogen several times, then heated at 135° C. for 36 h. The reaction mixture was diluted with water and EtOAc, washed with brine (twice), dried ($MgSO_4$), filtered and evaporated in vacuo to give a brown oil. Purification by flash column chromatography (silica, 120 g, 50-100% EtOAc/cyclohexane) followed by further chromatography (C18-silica, 150 g 40-90% acetonitrile-water (10 mM ammonium bicarbonate modifier) gradient) gave the title compound as a fine white powder (600 mg, 0.985 mmol, 10% yield). LCMS (high pH A): Rt=1.35 min, $MH^+$=579.4.

Description 119

1-(1-(Piperidin-4-yl)-1H-pyrazol[4,3-c]pyridin-4-yl)dihydropyrimidine-2,4(1H,3H)-dione (D119)

Benzyl 4-(4-(2,4-dioxo-3-((2-(trimethylsilyl)ethoxy)methyl)tetrahydropyrimidin-1(2H)-yl)-1H-pyrazolo[4,3-c]

pyridin-1-yl)piperidine-1-carboxylate (may be prepared as described in Description 118; 600 mg, 1.037 mmol), Pd—C (10% w/w) (110 mg, 1.037 mmol), ammonium formate (654 mg, 10.37 mmol) were dissolved in ethanol (10 mL) and heated at 90° C. for 1 h. The reaction mixture was filtered, evaporated in vacuo, taken up in DCM (1 mL), treated with TFA (2 mL), stirred 1 h, concentrated under a stream of nitrogen, taken up in 4 M $NH_3$-MeOH and stirred 1 h. The reaction mixture was concentrated under a stream of nitrogen. Purification by flash column chromatography (C18-silica, 100 g, 10-25% acetonitrile-water (10 mM ammonium bicarbonate modifier) gradient) gave the title compound as a white powder (270 mg, 0.816 mmol, 79% yield). LCMS (high pH A): Rt=0.51 min, $MH^+$=315.1.

Description 120 tert-Butyl 4-(6-chloro-4-iodo-1H-indazol-1-yl)piperidine-1-carboxylate (D120)

A mixture of 6-chloro-4-iodo-1H-indazole (216 mg, 0.776 mmol), tert-butyl 4-((methylsulfonyl)oxy)piperidine-1-carboxylate (260 mg, 0.931 mmol) and cesium carbonate (379 mg, 1.163 mmol) in anhydrous DMF (6.0 mL), was stirred at 60° C. for 5 h. Further tert-butyl 4-((methylsulfonyl)oxy)piperidine-1-carboxylate (390 mg) was added and the mixture stirred at 60° C. for 18 h. The reaction mixture was allowed to cool to room temperature and diluted with EtOAc (20 mL). The solution was washed sequentially with water (20 mL), UCI (5% aq., 20 mL) and brine (20 mL). The organic layer was passed through a hydrophobic frit and the filtrate evaporated in vacuo. The resulting oil was loaded in DCM (3 mL) and purified on a 24 g silica cartridge using a gradient of 0-40% EtOAc in cyclohexane over 12 column volumes. The appropriate fractions were combined and the solvent evaporated in vacuo to give the title compound as a light yellow solid (172 mg, 0.373 mmol). LCMS (formic A): Rt=1.59 min, M-$^t$$Bu^+$=406, 408.

Description 121 tert-Butyl 4-(6-chloro-4-(2,4-dioxo-3-((2-(trimethylsilyl)ethoxy)methyl)tetrahydropyrimidin-1(2H)-yl)-1H-indazol-1-yl)piperidine-1-carboxylate (D121)

A mixture of copper(I) iodide (10 mg, 0.053 mmol), potassium carbonate (96 mg, 0.697 mmol) and 3-((2-(trimethylsilyl)ethoxy)methyl)dihydropyrimidine-2,4(1H,3H)-dione (may be prepared as described in Description 4; 102 mg, 0.418 mmol) was suspended in a solution of tert-butyl 4-(6-chloro-4-iodo-1H-indazol-1-yl)piperidine-1-carboxylate (may be prepared as described in Description 120; 161 mg, 0.349 mmol) in anhydrous 1,4-dioxane (3.5 mL). Trans-N,N'-Dimethylcyclohexane-1,2-diamine (0.016 mL, 0.105 mmol) was added, the vessel sealed and evacuated and purged with nitrogen (×3). The mixture was stirred at 120° C. in the sealed vessel for 16 h. The reaction was allowed to cool to room temperature, the suspension filtered through Celite and the Celite washed with EtOAc (10 mL). The filtrate was evaporated in vacuo and the residue loaded in DCM (3 mL) and purified on a 24 g silica cartridge using a gradient of 0-80% EtOAc in cyclohexane over 12 column volumes. The appropriate fractions were combined and the solvent evaporated in vacuo to give the title compound as a white solid (136 mg, 0.235 mmol, 68% yield). LCMS (high pH A): Rt=1.47 min, M-$H^-$=576, 578.

Description 122

1-(6-Chloro-1-(piperidin-4-yl)-1H-indazol-4-yl)dihydropyrimidine-2,4(1H,3H)-dione Trifluoroacetate (D122)

A solution of tert-butyl 4-(6-chloro-4-(2,4-dioxo-3-((2-(trimethylsilyl)ethoxy)methyl)tetrahydropyrimidin-1(2H)-yl)-1H-indazol-1-yl)piperidine-1-carboxylate (may be prepared as described in Description 121; 131 mg, 0.227 mmol) in DCM (1 mL) was treated with TFA (0.250 mL, 3.24 mmol) and left to stand in a stoppered vessel for 4 h. The mixture was evaporated under a stream of nitrogen and the residue dissolved in methanol (1 mL) and treated with 4 M ammonia in methanol (1.699 mL, 6.80 mmol). The solution was stirred in a stoppered vessel at room temperature for 1 h and evaporated under a stream of nitrogen. The solid was triturated with EtOAc (2×2 mL) and dried in a vacuum oven to give the title compound as a white solid (108 mg, 0.234 mmol) which was used without purification in the next step. LCMS (high pH A): Rt=0.70 min, 347, 349 $MH^+$=.

Description 123 tert-Butyl 4-(4-bromo-6-(trifluoromethyl)-1H-indazol-1-yl)piperidine-1-carboxylate (D123)

To 4-bromo-6-(trifluoromethyl)-1H-indazole (2 g, 7.55 mmol) in DMF (20 mL) was added NaH (0.604 g, 15.09 mmol). After 15 min, one-third of the tert-butyl 4-((methylsulfonyl)oxy)piperidine-1-carboxylate (6.32 g, 22.64 mmol) was added. After 1 h, another one-third of the mesylate was added, and the reaction was heated at 80° C. The remainder of the mesylate added after about another hour, and the reaction was heated at 80° C. overnight. The reaction was diluted with EtOAc and $NH_4Cl$, washed with brine, dried, filtered, evaporated in vacuo and purified over silica, (120 g), eluting with 0-30% EtOAc in cyclohexane to give, as the first-eluting isomer, tert-butyl 4-(4-bromo-6-(trifluoromethyl)-1H-indazol-1-yl)piperidine-1-carboxylate (1.2 g, 2.54 mmol, 33.7% yield). LCMS (high pH A): Rt=1.56 min, M-$tBu^+$=392.0

Description 124 tert-Butyl 4-(4-(2,4-dioxo-3-((2-(trimethylsilyl)ethoxy)methyl)tetrahydropyrimidin-1(2H)-yl-6-(trifluoromethyl)-1H-indazol-1-yl)piperidine-1-carboxylate (D124)

3-((2-(Trimethylsilyl)ethoxy)methyl)dihydropyrimidine-2,4(1H,3H)-dione (may be prepared as described in Description 4; 500 mg, 2.046 mmol), potassium carbonate (435 mg, 3.15 mmol), trans-N,N'-dimethylcyclohexane-1,2-diamine (0.074 mL, 0.472 mmol), copper(I) iodide (45.0 mg, 0.236 mmol), anhydrous 1,4-dioxane (6 mL) and tert-butyl 4-(4-bromo-6-(trifluoromethyl)-1H-indazol-1-yl)piperidine-1-carboxylate (may be prepared as described in Description 123; 706 mg, 1.574 mmol) were mixed, degassed with vacuum/$N_2$ several times, then heated at 135° C. in a sealed tube overnight (approximately 16 h). the reaction was cooled, diluted with water, extracted with EtOAc, washed with brine twice, dried, filtered, evaporated in vacuo and purified over silica (80 g), eluting with 0-50% EtOAc in cyclohexane to give tert-butyl 4-(4-(2,4-dioxo-3-((2-(trimethylsilyl)ethoxy)methyl)tetrahydropyrimidin-1(2H)-yl)-6-(trifluoromethyl)-1H-indazol-1-yl)piperidine-1-carboxylate (600 mg, 0.932 mmol, 59.2% yield). LCMS (high pH A): Rt=1.49 min, M-$H^+$=610.3

Description 125

1-(1-(Piperidin-4-yl)-6-(trifluoromethyl)-1H-indazol-4-yl)dihydropyrimidine-2,4(1H,3H)-dione (D125)

To tert-butyl 4-(4-(2,4-dioxo-3-((2-(trimethylsilyl)ethoxy)methyl)tetrahydropyridin-1(2H)-yl)-6-(trifluoromethyl)-1H-indazol-1-yl)piperidine-1-carboxylate (may be prepared as described in Description 124; 600 mg, 0.981 mmol) in DCM (1 mL) was added TFA (2 mL, 26.0 mmol), and the reaction mixture was stirred at room temperature for 1 h. The solvent was removed in vacuo, and the residue treated with ammonia (4 M in methanol) (2 mL). The solution was stirred for 1 h, concentrated and purified by reverse-phase chromatography eluting, with 10-50% 10 mM pH10 $NH_4CO_2$ (aqueous) in acetonitrile to give 1-(1-(piperidin-4-yl)-6-(trifluoromethyl)-1H-indazol-4-yl)dihydropyrimidine-2,4(1H,3H)-dione (300 mg, 0.747 mmol, 76% yield). LCMS (high pH A): Rt=0.79 min, $MH^+$=382.2

EXAMPLE

Example 1-9

General Procedure

To a stirred solution of amine substrate (1.1 equivalent), 4-(4-((4-(4-(2,4-dioxotetrahydropyrimidin-1(2H)-yl-1H-indazol-1-yl)piperidin-1-yl)methyl)piperidin-1-yl)-3-fluorobenzoic acid, tris-trifluoroacetic acid salt (may be prepared as described in Description 8, 1 equivalents) and DIPEA (10 equivalents) in DMF (0.1 M) was added HATU (1.2 equivalents) then the mixture was stirred at room temperature for 30 min. The reaction mixture was directly purified by MDAP (formic acid modifier gradient) then the appropriate fractions were combined and concentrated under a stream of nitrogen to give the following products:

| Ex | Name; Analytical | Aldehyde | Mass, yield |
|---|---|---|---|
| 1 | 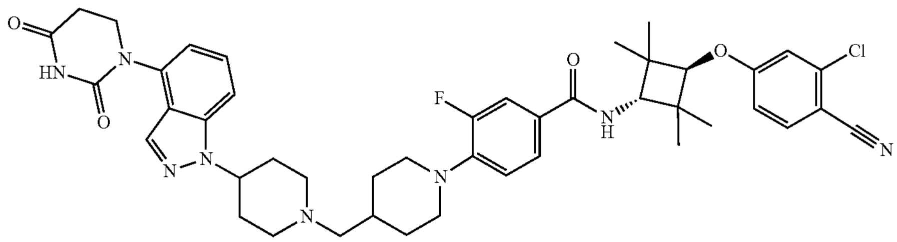 [SMILES: CC1(C)[C@H](NC(=O)c2ccc(N3CCC(CN4CCC(n5ncc6c(N7CCC(=O)NC7=O)cccc65)CC4)CC3)c(F)c2)C(C)(C)[C@H]1Oc1ccc(C#N)c(Cl)c1]<br>N-((1r,3r)-3-(3-Chloro-4-cyanophenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.93 min, MH+ = 810 | D32 | 69 mg, 73% yield |
| 2 | 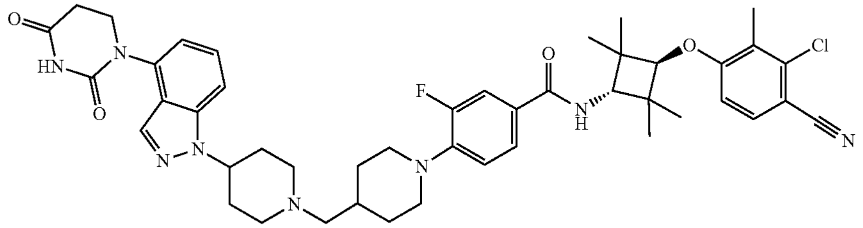 [SMILES: Cc1c(O[C@H]2C(C)(C)[C@H](NC(=O)c3ccc(N4CCC(CN5CCC(n6ncc7c(N8CCC(=O)NC8=O)cccc76)CC5)CC4)c(F)c3)C2(C)C)ccc(C#N)c1Cl]<br>N-((1r,3r)-3-(3-Chloro-4-cyano-2-methylphenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.98 min, MH+ = 824 | D9 | 50 mg, 52% yield |
| 3 | 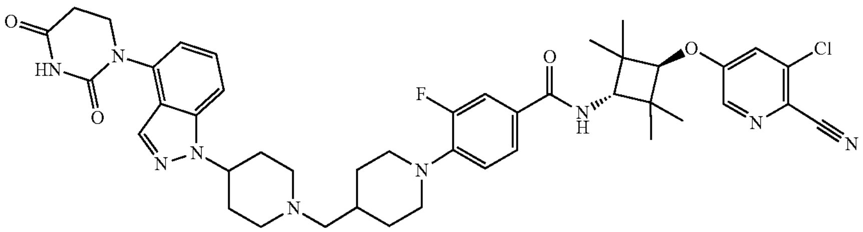 [SMILES: CC1(C)[C@H](NC(=O)c2ccc(N3CCC(CN4CCC(n5ncc6c(N7CCC(=O)NC7=O)cccc65)CC4)CC3)c(F)c2)C(C)(C)[C@H]1Oc1cnc(C#N)c(Cl)c1]<br>N-((1r,3r)-3-((5-Chloro-6-cyanopyridin-3-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.88 min, MH+ = 811 | D86 | 56 mg, 57% yield |

-continued

| Ex | Name;<br>Analytical | Alde-<br>hyde | Mass,<br>yield |
|---|---|---|---|
| 4 | 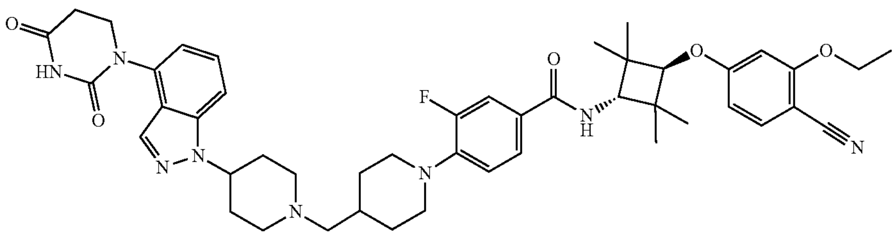 [SMILES: CCOc1cc(O[C@H]2C(C)(C)[C@H](NC(=O)c3ccc(N4CCC(CN5CCC(n6ncc7c(N8CCC(=O)NC8=O)cccc76)CC5)CC4)c(F)c3)C2(C)C)ccc1C#N]<br>N-((1r,3r)-3-(4-Cyano-3-ethoxyphenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.91 min, MH+ = 819 | D11 | 34 mg, 46% yield |
| 5 | 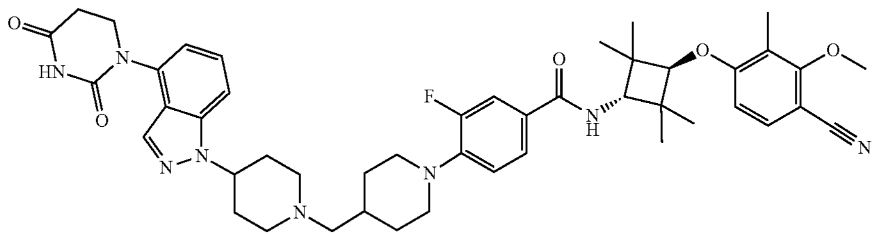<br>N-((1r,3r)-3-(4-Cyano-3-methoxy-2-methylphenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.92 min, MH+ = 819 | D13 | 69 mg, 68% yield |
| 6 | 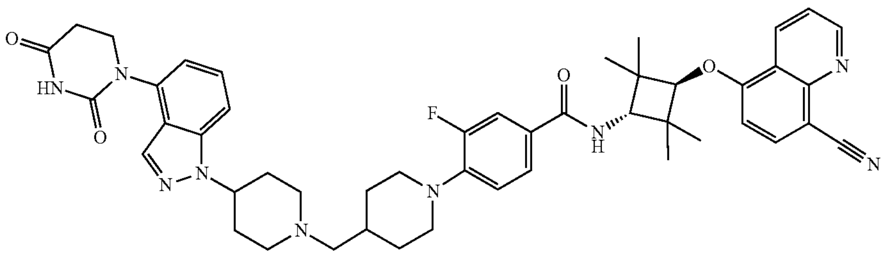 [SMILES: CC1(C)[C@H](NC(=O)c2ccc(N3CCC(CN4CCC(n5ncc6c(N7CCC(=O)NC7=O)cccc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>1H NMR (400 MHz, DMSO-$d_6$) δ 10.46 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.03 (s, 1H), 7.81-7.73 (m, 2H), 7.71-7.62 (m, 3H), 7.40 (dd, J = 8.5, 7.3 Hz, 1H), 7.15-7.08 (m, 1H), 7.05 (d, J = 7.0 Hz, 1H), 6.97 (d, J = 8.5 Hz, 1H), 4.64 (br d, J = 4.8 Hz, 1H), 4.50 (s, 1H), 4.18 (d, J = 9.0 Hz, 1H), 3.88 (t, J = 6.6 Hz, 2H), 3.51 (br d, J = 12.0 Hz, 2H), 3.01 (br d, J = 6.3 Hz, 2H), 2.82-2.72 (m, 4H), 2.28 (br d, J = 7.0 Hz, 2H), 2.24-2.11 (m, 4H), 2.00-1.83 (m, 4H), 1.73 (br s, 1H), 1.37-1.28 (m, 7H), 1.24 (s, 6H). LCMS (formic A): Rt = 0.86 min, MH+ = 827 | D49 | 84.6 mg, 61% yield |

-continued

| Ex | Name; Analytical | Alde-hyde | Mass, yield |
|---|---|---|---|
| 7 | 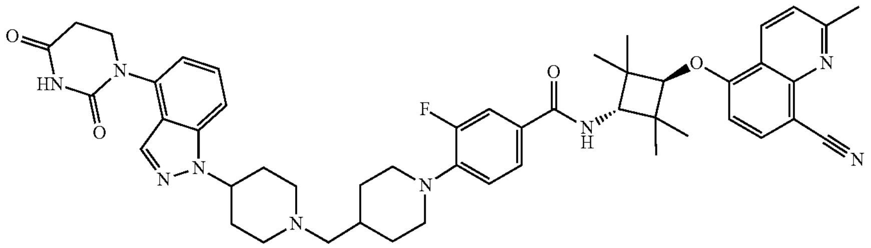 [SMILES: Cc1ccc2c(O[C@H]3C(C)(C)[C@H](NC(=O)c4ccc(N5CCC(CN6CCC(n7ncc8c(N9CCC(=O)NC9=O)cccc87)CC6)CC5)c(F)c4)C3(C)C)ccc(C#N)c2n1]<br>N-((1r,3r)-3-((8-cyano-2-methylquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.89 min, MH+ = 841 | D16 | 71 mg, 71% yield |
| 8 | 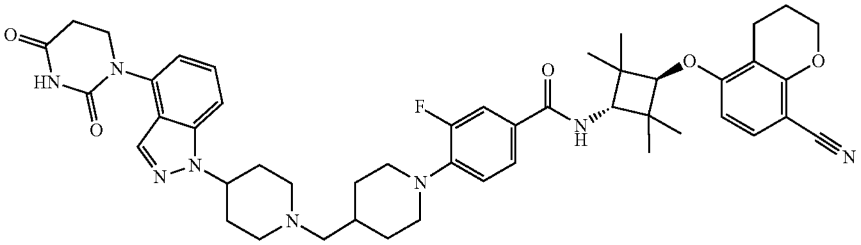 [SMILES: CC1(C)[C@H](NC(=O)c2ccc(N3CCC(CN4CCC(n5ncc6c(N7CCC(=O)NC7=O)cccc65)CC4)CC3)c(F)c2)C(C)(C)[C@H]1Oc1ccc(C#N)c2c1CCCO2]<br>N-((1r,3r)-3-((8-Cyanochroman-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.90 min, MH+ = 832 | D21 | 56 mg, 59% yield |
| 9 | 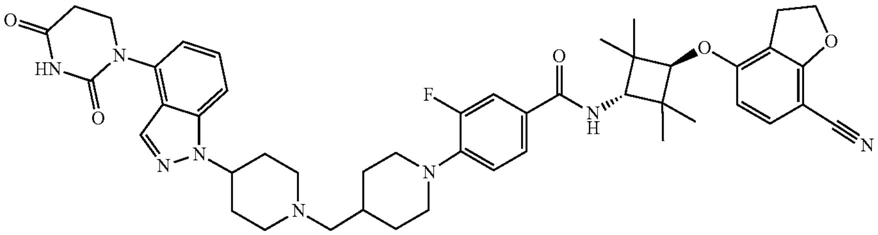 [SMILES: CC1(C)[C@H](NC(=O)c2ccc(N3CCC(CN4CCC(n5ncc6c(N7CCC(=O)NC7=O)cccc65)CC4)CC3)c(F)c2)C(C)(C)[C@H]1Oc1ccc(C#N)c2c1CCO2]<br>N-((1r,3r)-3-((7-Cyano-2,3-dihydrobenzofuran-4-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>LCMS (formic A): Rt = 0.88 min, MH+ = 818 | D25 | 54 mg, 58% yield |

Examples 10-46

General Procedure

To a solution of aldehyde (1 equivalent) and the corresponding amine substrate (1 equivalent) in either DCM: methanol (9:1, 0.1 M) or DMAc (0.1 M) was added sodium triacetoxyborohydride (3 equivalents) then the mixture was stirred at room temperature for 3 h. After this time, the reaction was diluted with DCM, then the phases were separated. The aqueous layer was back-extracted with DCM (2×15 ml). The organic phases were combined, dried over sodium sulfate, filtered and evaporated in vacuo. The crude samples were purified by the appropriate method to obtain the following compounds:

| Ex | Name;<br>Analytical | Aldehyde | Amine | Purification method;<br>Mass, yield |
|---|---|---|---|---|
| 10 | 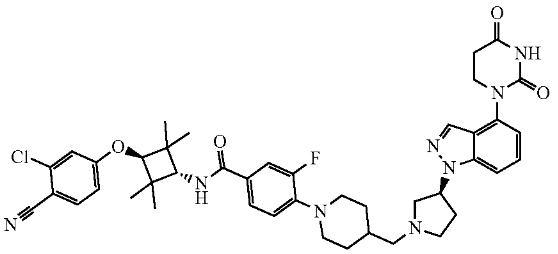 [SMILES: CC1(C)[C@H](NC(=O)c2ccc(N3CCC(CN4CC[C@H](n5ncc6c(N7CCC(=O)NC7=O)cccc65)C4)CC3)c(F)c2)C(C)(C)[C@H]1Oc1ccc(C#N)c(Cl)c1]<br>N-((1r,3r)-3-(3-Chloro-4-cyanophenoxy)-2,2,4,4-tetramethylcyclobutyl)-4-(4-(((S)-3-(4-(2,4-dioxotetrahydropyrimidin-1(2H)-yl)-1H-indazol-1-yl)pyrrolidin-1-yl)methyl)piperidin-1-yl)-3-fluorobenzamide, Formic acid salt<br>LCMS (formic B): Rt = 0.96 min, MH+ = 795 | D34 | D28 | Prep HPLC (formic); 40 mg, 4% yield |
| 11 | 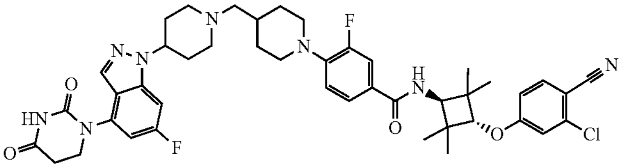 [SMILES: CC1(C)[C@H](NC(=O)c2ccc(N3CCC(CN4CCC(n5ncc6c(N7CCC(=O)NC7=O)cc(F)cc65)CC4)CC3)c(F)c2)C(C)(C)[C@H]1Oc1ccc(C#N)c(Cl)c1]<br>N-((1r,3r)-3-(3-Chloro-4-cyanophenoxy)-2,2,4,4-tetramethylcyclobutyl)-4-(4-((4-(4-(2,4-dioxotetrahydropyrimidin-1(2H)-yl)-6-fluoro-1H-indazol-1-yl)piperidin-1-yl)methyl)piperidin-1-yl)-3-fluorobenzamide<br>1H NMR (400 MHz, DMSO-d6) δ 10.54 (s, 1H), 8.04 (s, 1H), 7.91 (d, J = 8.8 Hz, 1H), 7.73 - 7.57 (m, 4H), 7.22 (d, J = 2.5 Hz, 1H), 7.10 (t, J = 8.8 Hz, 1H), 7.05 - 6.97 (m, 2H), 5.76 (s, 1H), 4.68 - 4.54 (m, 1H), 4.33 (s, 1H), 4.07 (d, J = 9.3 Hz, 1H), 3.91 (t, J = 6.6 Hz, 2H), 3.50 (br d, J = 11.8 Hz, 2H), 3.00 (br d, J = 8.5 Hz, 2H), 2.84 - 2.71 (m, 4H), 2.27 (br d, J = 7.0 Hz, 2H), 2.22 - 2.06 (m, 4H), 1.96 - 1.81 (m, 4H), 1.80 - 1.65 (m, 1H), 1.38 - 1.26 (m, 2H), 1.23 (s, 5H), 1.13 (s, 5H).<br>LCMS (formic B): Rt = 1.12 min, MH+ = 828 | D34 | D88 | Silica chromatography (25 g, 0-30% MeOH/DCM); 86.9 mg, 69% yield |
| 12 | 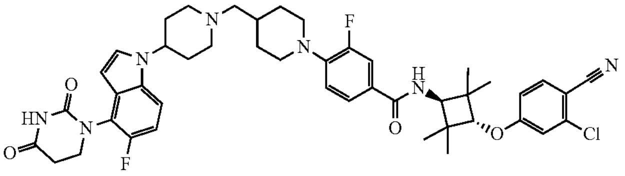 [SMILES: CC1(C)[C@H](NC(=O)c2ccc(N3CCC(CN4CCC(n5ccc6c(N7CCC(=O)NC7=O)c(F)ccc65)CC4)CC3)c(F)c2)C(C)(C)[C@H]1Oc1ccc(C#N)c(Cl)c1]<br>N-((1r,3r)-3-(3-Chloro-4-cyanophenoxy)-2,2,4,4-tetramethylcyclobutyl)-4-(4-((4-(4-(2,4-dioxotetrahydropyrimidin-1(2H)-yl)-5-fluoro-1H-indol-1-yl)piperidin-1-yl)methyl)piperidin-1-yl)-3-fluorobenzamide<br>1H NMR (400 MHz, DMSO-d6) δ 10.46 (s, 1H), 7.91 (d, J = 8.8 Hz, 1H), 7.72 - 7.61 (m, 4H), 7.58 (dd, J = 9.0, 3.8 Hz, 1H), 7.22 (d, J = 2.5 Hz, 1H), 7.14 - 7.04 (m, 2H), 7.01 (dd, J = 8.8, 2.3 Hz, 1H), 6.52 (d, J = 3.3 Hz, 1H), 5.76 (s, 1H), 4.45 - 4.35 (m, 1H), 4.33 (s, 1H), 4.07 (d, J = 9.3 Hz, 1H), 3.84 - 3.74 (m, 1H), 3.73 - 3.65 (m, 1H), 3.50 (br d, J = 12.0 Hz, 2H), 3.07 - 2.96 (m, 2H), 2.89 (ddd, J = 16.8, 8.8, 6.0 Hz, 1H), 2.81 - 2.63 (m, 4H), 2.28 (br d, J = 7.0 Hz, 2H), 2.18 (br t, J = 10.3 Hz, 2H), 2.07 - 1.91 (m, 4H), 1.86 (br d, J = 12.0 Hz, 2H), 1.73 (br dd, J = 3.9, 3.1 Hz, 1H), 1.38 - 1.25 (m, 3H), 1.23 (s, 6H), 1.13 (s, 6H).<br>LCMS (formic B): Rt = 1.12 min, MH+ = 827 | D34 | D91 | Silica chromatography (0-30% MeOH/DCM); 94.9 mg, 75% yield |

-continued

| Ex | Name; Analytical | Aldehyde | Amine | Purification method; Mass, yield |
|---|---|---|---|---|
| 13 | 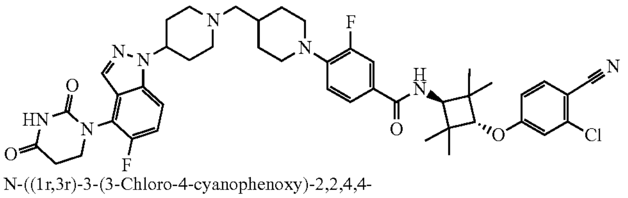<br>N-((1r,3r)-3-(3-Chloro-4-cyanophenoxy)-2,2,4,4-tetramethylcyclobutyl)-4-(4-((4-(4-(2,4-dioxotetrahydropyrimidin-1(2H)-yl)-5-fluoro-1H-indazol-1-yl)piperidin-1-yl)methyl)piperidin-1-yl)-3-fluorobenzamide<br>$^1$H NMR (400 MHz, DMSO-d6) δ 10.57 (s, 1H), 8.17 (s, 1H), 7.91 (d, J = 8.8 Hz, 1H), 7.79 (dd, J = 9.0, 3.5 Hz, 1H), 7.72 - 7.60 (m, 3H), 7.39 (dd, J = 10.3, 9.3 Hz, 1H), 7.22 (d, J = 2.5 Hz, 1H), 7.10 (t, J = 8.9 Hz, 1H), 7.01 (dd, J = 8.8, 2.5 Hz, 1H), 5.76 (s, 1H), 4.74 - 4.60 (m, 1H), 4.33 (s, 1H), 4.07 (d, J = 9.0 Hz, 1H), 3.92 - 3.82 (m, 1H), 3.82 - 3.71 (m, 1H), 3.50 (br d, J = 12.0 Hz, 2H), 3.01 (br d, J = 7.0 Hz, 2H), 2.96 - 2.84 (m, 1H), 2.82 - 2.66 (m, 4H), 2.27 (br d, J = 7.3 Hz, 2H), 2.23 - 2.07 (m, 4H), 2.00 - 1.81 (m, 5H), 1.80 - 1.65 (m, 1H), 1.39 - 1.19 (m, 9H), 1.17 - 1.08 (m, 6H)<br>LCMS (formic B): Rt = 1.10 min, MH+ = 828 | D34 | D94 | Silica chromatography (12 g, 0-100% [9:1 DCM:MeOH]/ DCM); 77 mg, 60% yield |
| 14 | 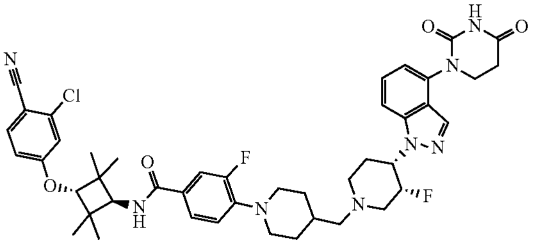 [SMILES: CC1(C)[C@H](NC(=O)c2ccc(N3CCC(CN4CC[C@H](n5ncc6c(N7CCC(=O)NC7=O)cccc65)[C@H](F)C4)CC3)c(F)c2)C(C)(C)[C@H]1Oc1ccc(C#N)c(Cl)c1]<br>N-((1r,3r)-3-(3-Chloro-4-cyanophenoxy)-2,2,4,4-tetramethylcyclobutyl)-4-(4-(((3R,4S)-4-(4-(2,4-dioxotetrahydropyrimidin-1(2H)-yl)-1H-indazol-1-yl)-3-fluoropiperidin-1-yl)methyl)piperidin-1-yl)-3-fluorobenzamide<br>1H NMR (400 MHz, DMSO-d6) δ 10.47 (s, 1H), 8.03 (s, 1H), 7.91 (d, J = 8.8 Hz, 1H), 7.75 - 7.61 (m, 4H), 7.45 - 7.39 (m, 1H), 7.22 (d, J = 2.5 Hz, 1H), 7.15 - 7.06 (m, 2H), 7.03 - 6.98 (m, 1H), 5.05 - 4.82 (m, 2H), 4.33 (s, 1H), 4.07 (d, J = 9.0 Hz, 1H), 3.89 (t, J = 6.6 Hz, 2H), 3.57 - 3.44 (m, 2H), 3.24 - 3.04 (m, 2H), 2.91 - 2.70 (m, 5H), 2.49 - 2.42 (m, 1H), 2.40 - 2.22 (m, 3H), 2.02 - 1.82 (m, 3H), 1.81 - 1.66 (m, 1H), 1.38 - 1.26 (m, 2H), 1.23 (s, 6H), 1.13 (s, 6H).<br>LCMS (formic B): Rt = 1.10 min, MH+ = 828 | D34 | D37 | Prep HPLC (high pH); 119 mg, 74% yield |
| 15 | 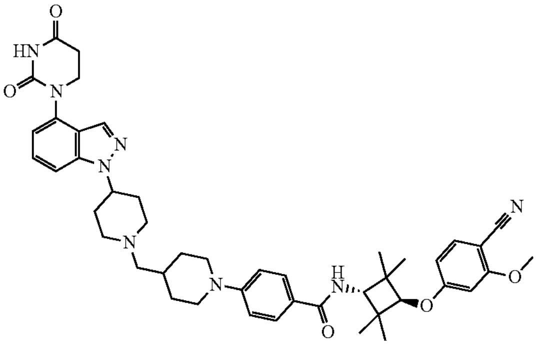 [SMILES: COc1cc(O[C@H]2C(C)(C)[C@H](NC(=O)c3ccc(N4CCC(CN5CCC(n6ncc7c(N8CCC(=O)NC8=O)cccc76)CC5)CC4)cc3)C2(C)C)ccc1C#N]<br>N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)benzamide, Formic acid salt<br>LCMS (formic A): Rt = 0.87 min, MH+ = 787 | D42 | D7 | MDAP (formic); 69.2 mg, 29% yield |

-continued

| Ex | Name; Analytical | Aldehyde | Amine | Purification method; Mass, yield |
|---|---|---|---|---|
| 16 | 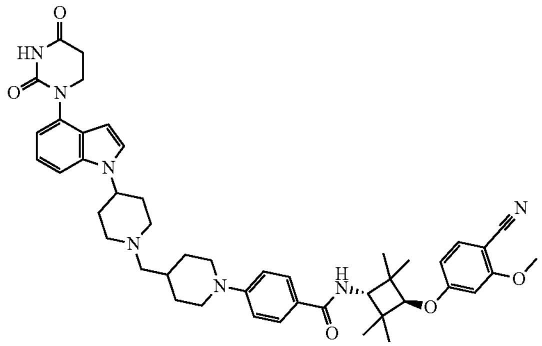 [SMILES: COc1cc(O[C@H]2C(C)(C)[C@H](NC(=O)c3ccc(N4CCC(CN5CCC(n6ccc7c(N8CCC(=O)NC8=O)cccc76)CC5)CC4)cc3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-indol-1-yl)piperidin-1-yl)methyl)piperidin-1-yl)benzamide, Formic acid salt LCMS (formic A): Rt = 0.87 min, MH+ = 786 | D42 | D99 | MDAP (formic); 49.1 mg, 20% yield |
| 17 | 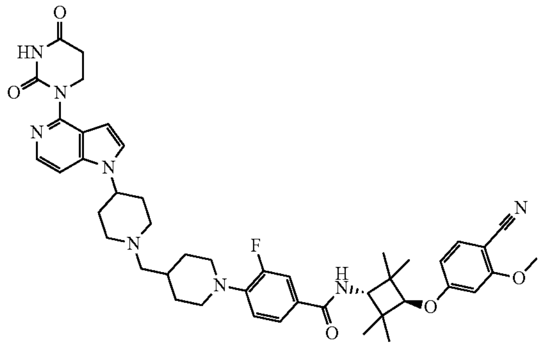 [SMILES: COc1cc(O[C@H]2C(C)(C)[C@H](NC(=O)c3ccc(N4CCC(CN5CCC(n6ccc7c(N8CCC(=O)NC8=O)nccc76)CC5)CC4)c(F)c3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrrolo[3,2-c]pyridin-1-yl)piperidin-1-yl)methyl)piperidin-1-yl)-3-fluorobenzamide, Formic acid salt 1H NMR (400 MHz, DMSO-d6) δ 1.16 (s, 6H) 1.24 (s, 6 H) 1.26-1.36 (m, 2H) 1.68-1.79 (m, 1H) 1.87 (br d, J = 11.26 Hz, 2H) 1.90-1.97 (m, 2H) 1.97 −2.10 (m, 2 H) 2.19 (br t, J = 10.76 Hz, 2H) 2.28 (br d, J = 7.25 Hz, 2H) 2.70-2.81 (m, 4H) 3.02 (br d, J = 11.01 Hz, 2H) 3.50 (br d, J = 12.26 Hz, 2H) 3.89- 3.96 (m, 5H) 4.07 (d, J = 9.01 Hz, 1 H) 4.28 (s, 1H) 4.37-4.48 (m, 1H) 6.42 (d, J = 3.25 Hz, 1H) 6.55 (dd, J = 8.63, 2.13 Hz, 1H) 6.65 (d, J = 2.25 Hz, 1H) 7.10 (t, J = 8.76 Hz, 1H) 7.54 (d, J = 5.50 Hz, 1H) 7.61 (d, J = 3.50 Hz, 1H) 7.62-7.68 (m, 3H) 7.70 (d, J = 9.26 Hz, 1H) 8.06 (d, J = 5.75 Hz, 1 H) 8.16 (s, 1H) 10.47 (s, 1H). LCMS (formic B): Rt = 0.94 min, MH+ = 805 | D44 | D104 | Prep HPLC (formic); 52.1 mg, 37% yield |

-continued

| Ex | Name; Analytical | Aldehyde | Amine | Purification method; Mass, yield |
|---|---|---|---|---|
| 18 | 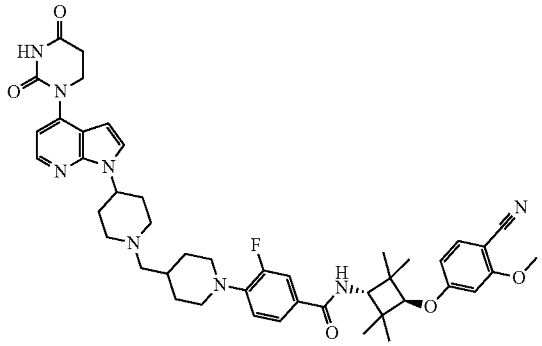 [SMILES: COc1cc(O[C@H]2C(C)(C)[C@H](NC(=O)c3ccc(N4CCC(CN5CCC(n6ccc7c(N8CCC(=O)NC8=O)ccnc76)CC5)CC4)c(F)c3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrrolo[2,3-b]pyridin-1-yl)piperidin-1-yl)methyl)piperidin-1-yl)-3-fluorobenzamide LCMS (formic B): Rt = 0.99 min, MH+ = 805 | D44 | D105 | Prep HPLC (high pH); 18.8 mg, 14% yield |
| 19 | 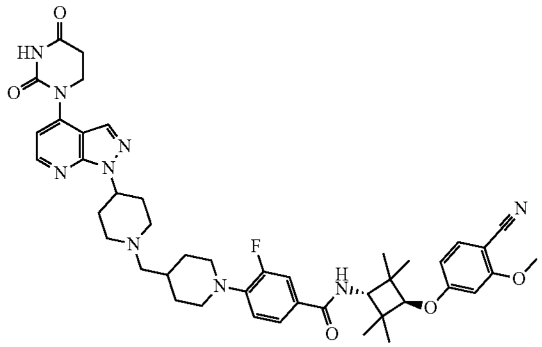 [SMILES: COc1cc(O[C@H]2C(C)(C)[C@H](NC(=O)c3ccc(N4CCC(CN5CCC(n6ncc7c(N8CCC(=O)NC8=O)ccnc76)CC5)CC4)c(F)c3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[3,4-b]pyridin-1-yl)piperidin-1-yl)methyl)piperidin-1-yl)-3-fluorobenzamide, Formic acid salt 1H NMR (400 MHz, DMSO-d6) δ 10.71 (s, 1H), 8.52 (d, J = 5.3 Hz, 1H), 8.15 (s, 1H), 8.04 (s, 1H), 7.73 - 7.61 (m, 4H), 7.14 - 7.05 (m, 2H), 6.67 - 6.63 (m, 1H), 6.57 - 6.51 (m, 1H), 4.90 - 4.77 (m, 1H), 4.28 (s, 1H), 4.11 - 4.03 (m, 3H), 3.95 - 3.88 (m, 3H), 3.55 - 3.47 (m, 2H), 3.07 - 2.99 (m, 2H), 2.82 - 2.71 (m, 4H), 2.33 - 2.10 (m, 6H), 1.97 - 1.80 (m, 4H), 1.80 - 1.66 (m, 1H), 1.39 - 1.27 (m, 2H), 1.24 (s, 6H), 1.15 (s, 6H). LCMS (formic B): Rt = 0.98 min, MH+ = 807 | D44 | D108 | Prep HPLC (formic); 109 mg, 61% yield |

-continued

| Ex | Name; Analytical | Aldehyde | Amine | Purification method; Mass, yield |
|---|---|---|---|---|
| 20 | 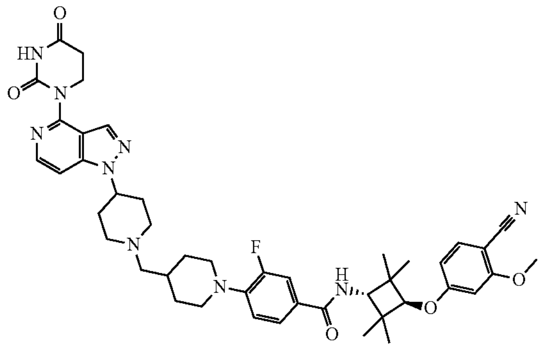 [SMILES: COc1cc(O[C@H]2C(C)(C)[C@H](NC(=O)c3ccc(N4CCC(CN5CCC(n6ncc7c(N8CCC(=O)NC8=O)nccc76)CC5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide, Formic acid salt<br>1H NMR (400 MHz, DMSO-d6 + $D_2O$) δ 1.06 – 1.40 (m, 13 H) 1.59 – 2.01 (m, 5 H) 2.11 – 2.43 (m, 6 H) 2.65 – 2.82 (m, 4 H) 3.04 (br d, J = 9.85 Hz, 2 H) 3.49 (br d, J = 12.38 Hz, 3 H) 3.89 (s, 3 H) 3.96 – 4.12 (m, 3 H) 4.27 (s, 1 H) 4.55 – 4.76 (m, 1 H) 6.54 (dd, J = 8.72, 2.15 Hz, 1 H) 6.63 (d, J = 2.02 Hz, 1 H) 7.03 – 7.13 (m, 1 H) 7.55 – 7.68 (m, 4 H) 7.72 (d, J = 9.35 Hz, 1 H) 8.04 (s, 1 H) 8.14 – 8.23 (m, 2 H)<br>LCMS (formic B): Rt = 0.98 min, MH+ = 807 | D44 | D119 | Prep HPLC (Formic); 69 mg, 39% yield |
| 21 | 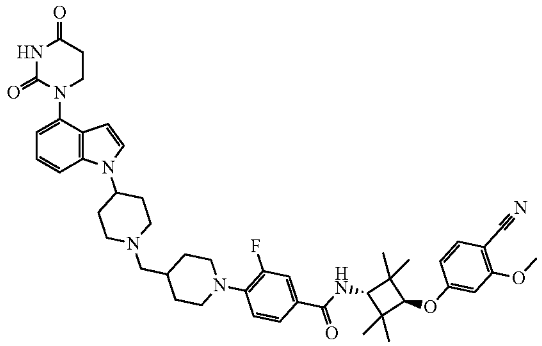 [SMILES: COc1cc(O[C@H]2C(C)(C)[C@H](NC(=O)c3ccc(N4CCC(CN5CCC(n6ccc7c(N8CCC(=O)NC8=O)cccc76)CC5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3-fluorobenzamide, Formic acid salt<br>1H NMR (400 MHz, DMSO-d6) δ 10.46 (s, 1H), 8.15 (s, 1H), 8.03 (s, 1H), 7.74 – 7.61 (m, 5H), 7.40 (dd, J = 8.4, 7.4 Hz, 1H), 7.14 – 7.07 (m, 1H), 7.05 (d, J = 7.0 Hz, 1H), 6.65 (d, J = 2.0 Hz, 1H), 6.55 (dd, J = 8.5, 2.3 Hz, 1H), 4.71 – 4.59 (m, 1H), 4.28 (s, 1H), 4.07 (d, J = 9.0 Hz, 1H), 3.91 (s, 3H), 3.88 (t, J = 6.6 Hz, 2H), 3.50 (br d, J = 12.0 Hz, 2H), 3.02 (br d, J = 8.3 Hz, 2H), 2.82 – 2.71 (m, 4H), 2.29 (br d, J = 7.0 Hz, 2H), 2.26 – 2.12 (m, 4H), 1.96 – 1.82 (m, 4H), 1.81 – 1.67 (m, 1H), 1.38 – 1.25 (m, 2H), 1.23 (s, 6H), 1.15 (s, 6H).<br>LCMS (formic B): Rt = 1.91 min, MH+ = 806 | D44 | D7 | Prep HPLC (formic); 109 mg, 70% yield |

-continued

| Ex | Name; Analytical | Aldehyde | Amine | Purification method; Mass, yield |
|---|---|---|---|---|
| 22 | 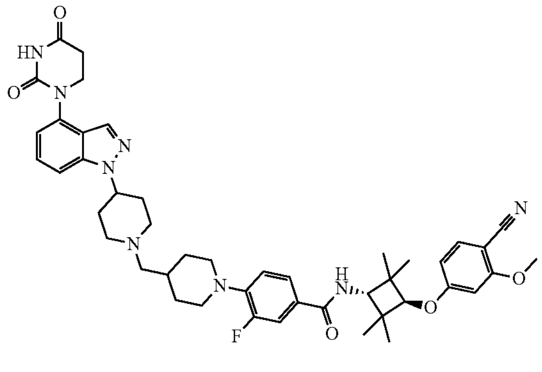 [SMILES: COc1cc(O[C@H]2C(C)(C)[C@H](NC(=O)c3ccc(N4CCC(CN5CCC(n6ncc7c(N8CCC(=O)NC8=O)cccc76)CC5)CC4)c(F)c3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-indol-1-yl)piperidin-1-yl)methyl)piperidin-1-yl)-3-fluorobenzamide<br>1H NMR (400 MHz, DMSO-d6) δ 10.32 (s, 1H), 7.73 - 7.61 (m, 4H), 7.54 (d, J = 3.5 Hz, 1H), 7.51 (d, J = 8.5 Hz, 1H), 7.17 - 7.12 (m, 1H), 7.09 (t, J = 8.8 Hz, 1H), 6.96 (d, J = 7.5 Hz, 1H), 6.64 (d, J = 2.3 Hz, 1H), 6.54 (dd, J = 8.8, 2.3 Hz, 1H), 6.42 (d, J = 3.3 Hz, 1H), 4.44 - 4.32 (m, 1H), 4.27 (s, 1H), 4.06 (d, J = 9.3 Hz, 1H), 3.91 (s, 3H), 3.82 - 3.74 (m, 2H), 3.55 - 3.44 (m, 2H), 3.08 - 2.93 (m, 2H), 2.82 - 2.70 (m, 4H), 2.32 - 2.24 (m, 2H), 2.19 (br t, J = 10.5 Hz, 2H), 2.06 - 1.91 (m, 4H), 1.90 - 1.81 (m, 2H), 1.79 - 1.66 (m, 1H), 1.38 - 1.26 (m, 2H), 1.23 (s, 6H), 1.15 (s, 6H).<br>LCMS (formic B): Rt = 1.05 min, MH+ = 805 | D44 | D99 | Prep HPLC (high pH); 52.5 mg, 48% yield |
| 23 | 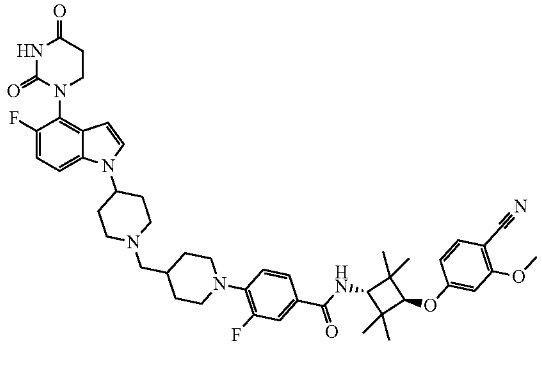 [SMILES: COc1cc(O[C@H]2C(C)(C)[C@H](NC(=O)c3ccc(N4CCC(CN5CCC(n6ccc7c(N8CCC(=O)NC8=O)c(F)ccc76)CC5)CC4)c(F)c3)C2(C)C)ccc1C#N] N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-5-fluoro-1H-indol-1-yl)piperidin-1-yl)methyl)piperidin-1-yl)-3-fluorobenzamide<br>1H NMR (400 MHz, DMSO-d6) δ 10.45 (s, 1H), 7.75 - 7.60 (m, 5H), 7.57 (dd, J = 8.9, 3.6 Hz, 1H), 7.14 - 7.03 (m, 2H), 6.66 - 6.62 (m, 1H), 6.54 (dd, J = 8.6, 2.1 Hz, 1H), 6.51 (d, J = 3.3 Hz, 1H), 4.46 - 4.33 (m, 1H), 4.27 (s, 1H), 4.06 (d, J = 9.3 Hz, 1H), 3.91 (s, 3H), 3.82 - 3.74 (m, 1H), 3.73 - 3.64 (m, 1H), 3.55 - 3.45 (m, 2H), 3.08 - 2.96 (m, 2H), 2.93 - 2.84 (m, 1H), 2.81 - 2.62 (m, 3H), 2.32 - 2.24 (m, 2H), 2.23 - 2.12 (m, 2H), 2.07 - 1.90 (m, 4H), 1.90 - 1.80 (m, 2H), 1.80 - 1.64 (m, 1H), 1.38 - 1.25 (m, 2H), 1.23 (s, 6H), 1.15 (s, 6H).<br>LCMS (formic B): Rt = 1.06 min, MH+ = 823 | D44 | D91 | Prep HPLC (high pH); 78.6 mg, 71% yield |

-continued

| Ex | Name; Analytical | Aldehyde | Amine | Purification method; Mass, yield |
|---|---|---|---|---|
| 24 | 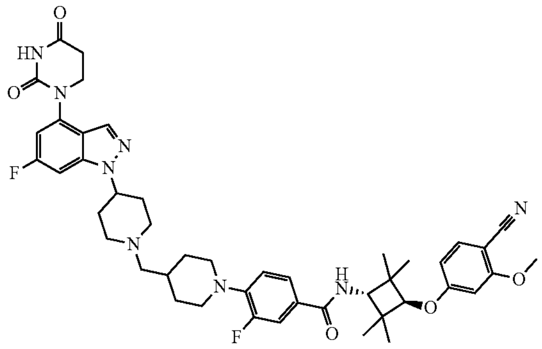 [SMILES: COc1cc(O[C@H]2C(C)(C)[C@H](NC(=O)c3ccc(N4CCC(CN5CCC(n6ncc7c(N8CCC(=O)NC8=O)cc(F)cc76)CC5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-6-fluoro-1H-indazol-1-yl)piperidin-1-yl)methyl)piperidin-1-yl)-3-fluorobenzamide<br>1H NMR (400 MHz, DMSO-d6) δ 10.54 (s, 1H), 8.04 (s, 1H), 7.74 - 7.57 (m, 5H), 7.10 (t, J = 8.9 Hz, 1H), 7.06 - 6.97 (m, 1H), 6.65 (d, J = 2.3 Hz, 1H), 6.57 - 6.52 (m, 1H), 4.66 - 4.54 (m, 1H), 4.27 (s, 1H), 4.09 - 4.04 (m, 1H), 3.99 - 3.85 (m, 5H), 3.57 - 3.45 (m, 2H), 3.06 - 2.96 (m, 2H), 2.84 - 2.71 (m, 4H), 2.32 - 2.23 (m, 2H), 2.22 - 2.06 (m, 4H), 1.97 - 1.81 (m, 4H), 1.79 - 1.66 (m, 1H), 1.38 - 1.26 (m, 2H), 1.23 (s, 6H), 1.16 (s, 6H).<br>LCMS (formic B): Rt = 1.06 min, MH+ = 824 | D44 | D88 | Prep HPLC (high pH); 80.8 mg, 73% yield |
| 25 | 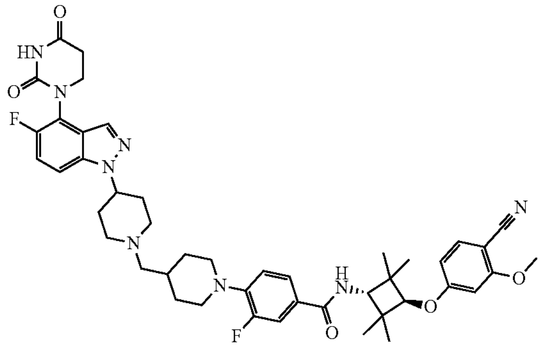 [SMILES: COc1cc(O[C@H]2C(C)(C)[C@H](NC(=O)c3ccc(N4CCC(CN5CCC(n6ncc7c(N8CCC(=O)NC8=O)c(F)ccc76)CC5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-5-fluoro-1H-indazol-1-yl)piperidin-1-yl)methyl)piperidin-1-yl)-3-fluorobenzamide<br>1H NMR (400 MHz, DMSO-d6) δ 10.56 (s, 1H), 8.16 (s, 1H), 7.79 (dd, J = 9.1, 3.4 Hz, 1H), 7.69 (d, J = 9.3 Hz, 1H), 7.67 - 7.61 (m, 3H), 7.39 (dd, J = 10.3, 9.3 Hz, 1H), 7.13 - 7.06 (m, 1H), 6.64 (d, J = 2.3 Hz, 1H), 6.54 (dd, J = 8.6, 2.1 Hz, 1H), 4.73 - 4.61 (m, 1H), 4.27 (s, 1H), 4.06 (d, J = 9.3 Hz, 1H), 3.94 - 3.89 (m, 3H), 3.89 - 3.82 (m, 1H), 3.81 - 3.71 (m, 1H), 3.49 (br d, J = 11.8 Hz, 2H), 3.07 - 2.96 (m, 2H), 2.94 - 2.84 (m, 1H), 2.80 - 2.65 (m, 3H), 2.32 - 2.24 (m, 2H), 2.24 - 2.08 (m, 4H), 1.99 - 1.81 (m, 4H), 1.80 - 1.64 (m, 1H), 1.39 - 1.26 (m, 2H), 1.23 (s, 6H), 1.15 (s, 6H). | D44 | D94 | Prep HPLC (highpH); 47.6 mg, 43% yield |

-continued

| Ex | Name; Analytical | Aldehyde | Amine | Purification method; Mass, yield |
|---|---|---|---|---|
| | LCMS (formic B): Rt = 1.04 min, MH+ = 824 | | | |
| 26 | 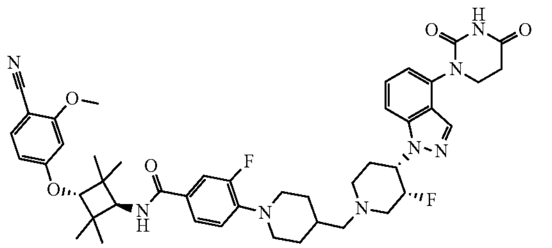 [SMILES: COc1cc(O[C@H]2C(C)(C)[C@H](NC(=O)c3ccc(N4CCC(CN5CC[C@H](n6ncc7c(N8CCC(=O)NC8=O)cccc76)[C@H](F)C5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-(((3R,4S)-4-(4-(2,4-dioxotetrahydropyrimidin-1(2H)-yl)-1H-indazol-1-yl)-3-fluoropiperidin-1-yl)methyl)piperidin-1-yl)-3-fluorobenzamide<br>1H NMR (400 MHz, DMSO-d6) δ 10.46 (s, 1H), 8.02 (s, 1H), 7.77 - 7.59 (m, 5H), 7.45 - 7.37 (m, 1H), 7.14 - 7.04 (m, 2H), 6.64 (d, J = 2.3 Hz, 1H), 6.54 (dd, J = 8.8, 2.3 Hz, 1H), 5.05 - 4.80 (m, 2H), 4.27 (s, 1H), 4.09 - 4.03 (m, 1H), 3.94 - 3.85 (m, 5H), 3.57 - 3.44 (m, 2H), 3.24 - 3.03 (m, 2H), 2.88 - 2.69 (m, 5H), 2.49 - 2.41 (m, 1H), 2.41 - 2.24 (m, 3H), 2.02 - 1.80 (m, 3H), 1.80 - 1.63 (m, 1H), 1.39 - 1.19 (m, 8H), 1.15 (s, 6H).<br>LCMS (formic B): Rt = 1.03 min, MH+ = 824 | D44 | D37 | Prep HPLC (high pH); 51 mg, 37% yield |
| 27 | 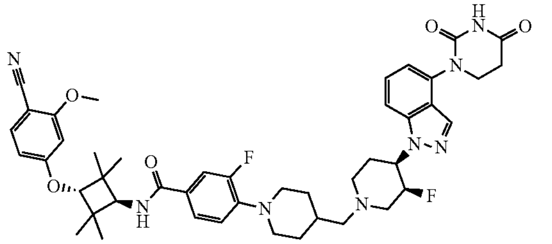 [SMILES: COc1cc(O[C@H]2C(C)(C)[C@H](NC(=O)c3ccc(N4CCC(CN5CC[C@@H](n6ncc7c(N8CCC(=O)NC8=O)cccc76)[C@@H](F)C5)CC4)c(F)c3)C2(C)C)ccc1C#N]<br>N-((1r,3r)-3-(4-Cyano-3-methoxyphenoxy)-2,2,4,4-tetramethylcyclobutyl)-4-(4-(((3,4R)-4-(4-(2,4-dioxotetrahydropyrimidin-1(2H)-yl)-1H-indazol-1-yl)-3-fluoropiperidin-1-yl)methyl)piperidin-1-yl)-3-fluorobenzamide<br>1H NMR (400 MHz, DMSO-d6) δ 10.47 (s, 1H), 8.03 (s, 1H), 7.76 - 7.61 (m, 5H), 7.45 - 7.39 (m, 1H), 7.17 - 7.06 (m, 2H), 6.65 (d, J = 2.3 Hz, 1H), 6.55 (dd, J = 8.6, 2.1 Hz, 1H), 5.08 - 4.83 (m, 2H), 4.28 (s, 1H), 4.09 - 4.04 (m, 1H), 3.94 - 3.85 (m, 5H), 3.57 - 3.45 (m, 2H), 3.23 - 3.04 (m, 2H), 2.89 - 2.70 (m, 5H), 2.48 - 2.40 (m, 1H), 2.39 - 2.23 (m, 3H), 2.04 - 1.82 (m, 3H), 1.80 - 1.66 (m, 1H), 1.39 - 1.27 (m, 2H), 1.24 (s, 6H), 1.15 (s, 6H).<br>LCMS (formic B): Rt = 1.03 min, MH+ = 824 | D44 | D47 | Prep HPLC (high pH); 68 mg, 61% yield |
| 28 | 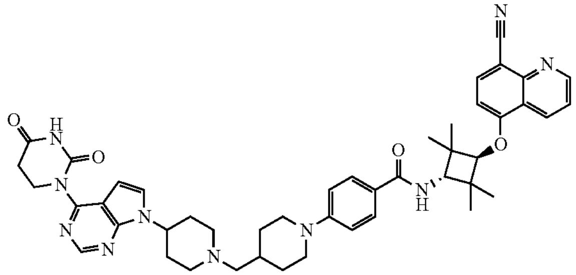 [SMILES: CC1(C)[C@H](NC(=O)c2ccc(N3CCC(CN4CCC(n5ccc6c(N7CCC(=O)NC7=O)ncnc65)CC4)CC3)cc2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-7H-pyrrolo[2,3-d]pyrimidin-7-yl)piperidin-1-yl)methyl)piperidin-1-yl)benzamide<br>LCMS (formic A): Rt = 1.29 min, MH+ = 809 | D42 | D113 | MDAP (high pH); 14.7 mg, 5% yield |

-continued

| Ex | Name;<br>Analytical | Aldehyde | Amine | Purification method;<br>Mass, yield |
|---|---|---|---|---|
| 29 | 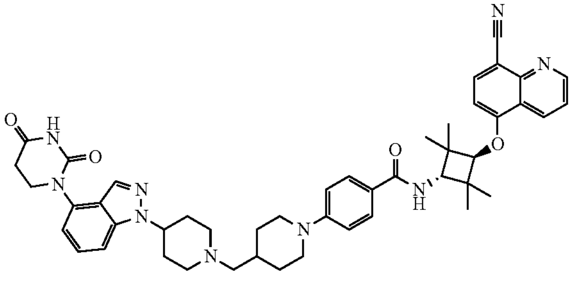 [SMILES: CC1(C)[C@H](NC(=O)c2ccc(N3CCC(CN4CCC(n5ncc6c(N7CCC(=O)NC7=O)cccc65)CC4)CC3)cc2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)benzamide, Formic acid salt<br>LCMS (formic A): Rt = 0.83 min, MH+ = 808 | D42 | D7 | MDAP (formic); 187 mg, 55% yield |
| 30 | 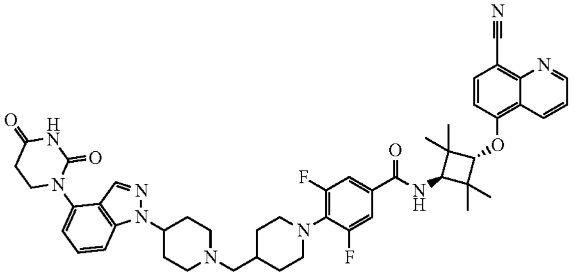 [SMILES: CC1(C)[C@H](NC(=O)c2cc(F)c(N3CCC(CN4CCC(n5ncc6c(N7CCC(=O)NC7=O)cccc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-3,5-difluorobenzamide, Formic acid salt<br>LCMS (formic B): Rt = 0.89 min, MH+ = 845 | D55 | D7 | MDAP (formic); 31 mg, 19% yield |
| 31 | 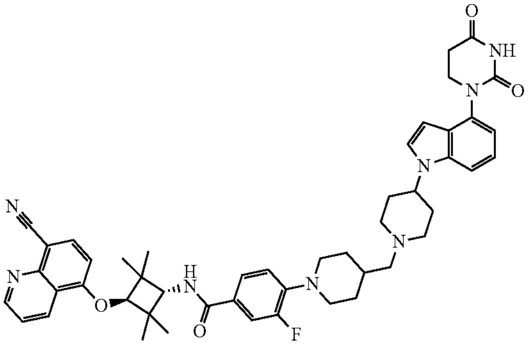 [SMILES: CC1(C)[C@H](NC(=O)c2ccc(N3CCC(CN4CCC(n5ccc6c(N7CCC(=O)NC7=O)cccc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indol-1-yl)piperidin-1-yl)methyl)piperidin-1-yl)-3-fluorobenzamide, Formic acid salt<br>1H NMR (400 MHz, DMSO-d6) δ 10.33 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.16 (s, 1H), 7.80 - 7.73 (m, 2H), 7.71 - 7.64 (m, 2H), 7.55 (d, J = 3.3 Hz, 1H), 7.52 (d, J = 8.5 Hz, 1H), 7.20 - 7.07 (m, 2H), 7.00 - 6.95 (m, 2H), 6.43 (d, J = 3.3 Hz, 1H), 5.76 (s, 1H), 4.50 (s, 1H), 4.45 - 4.34 (m, 1H), 4.18 (d, J = 9.3 Hz, 1H), 3.79 (t, J = 6.8 Hz, 2H), 3.51 (br d, J = 11.8 Hz, 2H), 3.03 (br d, J = 11.3 Hz, 2H), 2.77 (br t, J = 6.6 Hz, 4H), 2.29 (br d, J = 7.0 Hz, 2H), 2.25 - 2.15 (m, 2H), 2.11 - 1.92 (m, 4H), 1.87 (br d, J = 11.8 Hz, 2H), 1.79 - 1.68 (m, 1H), 1.39 - 1.28 (m, 8H), 1.24 (s, 6H).<br>LCMS (high pH D): Rt = 1.96 min, MH+ = 826 | D57 | D99 | Prep HPLC (formic); 108 mg, 43% yield |

-continued

| Ex | Name; Analytical | Aldehyde | Amine | Purification method; Mass, yield |
|---|---|---|---|---|
| 32 | 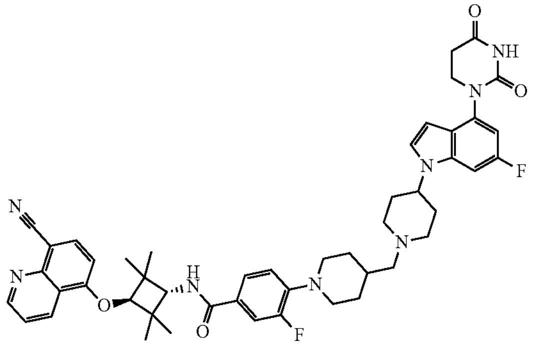 [SMILES: CC1(C)[C@H](NC(=O)c2ccc(N3CCC(CN4CCC(n5ccc6c(N7CCC(=O)NC7=O)cc(F)cc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-6-fluoro-1H-indol-1-yl)piperidin-1-yl)methyl)piperidin-1-yl)-3-fluorobenzamide, Formic acid salt<br>1H NMR (400 MHz, DMSO-d6) δ 10.40 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.15 (s, 1H), 7.79 - 7.73 (m, 2H), 7.69 (s, 1H), 7.66 (dd, J = 6.0, 1.5 Hz, 1H), 7.56 (d, J = 3.5 Hz, 1H), 7.46 (dd, J = 10.3, 1.8 Hz, 1H), 7.15 - 7.07 (m, 1H), 6.98 (d, J = 8.5 Hz, 1H), 6.92 (dd, J = 10.6, 2.1 Hz, 1H), 6.44 (d, J = 3.0 Hz, 1H), 4.50 (s, 1H), 4.42 - 4.32 (m, 1H), 4.18 (d, J = 9.0 Hz, 1H), 3.81 (t, J = 6.6 Hz, 2H), 3.51 (br d, J = 11.8 Hz, 2H), 3.01 (br d, J = 11.0 Hz, 2H), 2.82 - 2.72 (m, 4H), 2.28 (br d, J = 7.0 Hz, 2H), 2.25 - 2.15 (m, 2H), 2.06 - 1.91 (m, 4H), 1.87 (br d, J = 13.0 Hz, 2H), 1.80 - 1.68 (m, 1H), 1.37 - 1.27 (m, 8H), 1.24 (s, 6H)<br>LCMS (high pH D): Rt = 2.00 min, MH+ = 844 | D57 | D117 | Prep HPLC (formic); 80 mg, 31% yield |
| 33 | 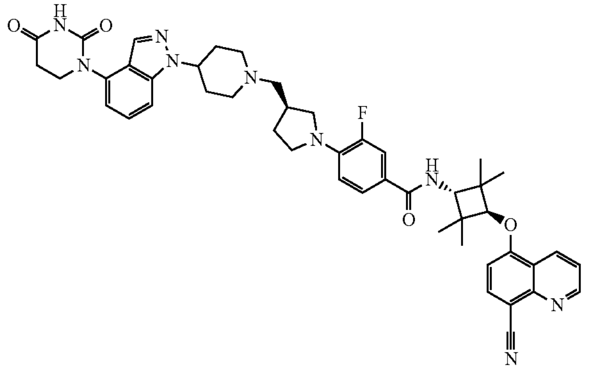 [SMILES: CC1(C)[C@H](NC(=O)c2ccc(N3CC[C@@H](CN4CCC(n5ncc6c(N7CCC(=O)NC7=O)cccc65)CC4)C3)c(F)c2)C(C)(C)[C@H]1Oc1ccc(C#N)c2ncccc12]<br>N-((1r,3S)-3-((8-Cyanoquinolin-5-yl)oxy)-2,2,4,4-tetramethylcyclobutyl)-4-((S)-3-((4-(4-(2,4-dioxotetrahydropyrimidin-1(2H)-yl)-1H-indazol-1-yl)piperidin-1-yl)methyl)pyrrolidin-1-yl)-3-fluorobenzamide, Formic acid salt<br>1H NMR (400 MHz, DMSO+D2O) δ 9.09 (dd, J = 4.3, 1.5 Hz, 1H), 8.73 (dd, J = 8.5, 1.6 Hz, 1H), 8.29 (d, J = 8.3 Hz, 1H), 8.17 (s, 1H), 8.01 (s, 1H), 7.74(dd, J = 8.6, 4.3 Hz, 1H), 7.69 - 7.54 (m, 4H), 7.44 - 7.35 (m, 1H), 7.12 - 6.92 (m, 2H), 6.73 (t, J = 8.8 Hz, 1H), 4.73 - 4.64 (m, 1H), 4.49 (s, 1H), 4.15 (d, J = 9.1 Hz, 1H), 3.87 (t, J = 6.7 Hz, 2H), 3.53 - 3.42 (m, 2H), 3.23 (br t, J = 7.2 Hz, 1H), 3.19 - 3.00 (m, 3H), 2.78 (t, J = 6.7 Hz, 2H), 2.63 - 2.55 (m, 1H), 2.41 - 2.03 (m, 5H), 1.93 (br d, J = 9.9 Hz, 2H), 1.76 - 1.56 (m, 1H), 1.38 - 1.06 (m, 12H)<br>LCMS (formic B): Rt = 0.95 min, MH+ = 813 | D61 | D7 | Prep HPLC (formic); 115 mg, 62% yield |

-continued

| Ex | Name;<br>Analytical | Aldehyde | Amine | Purification<br>method;<br>Mass, yield |
|---|---|---|---|---|
| 34 | 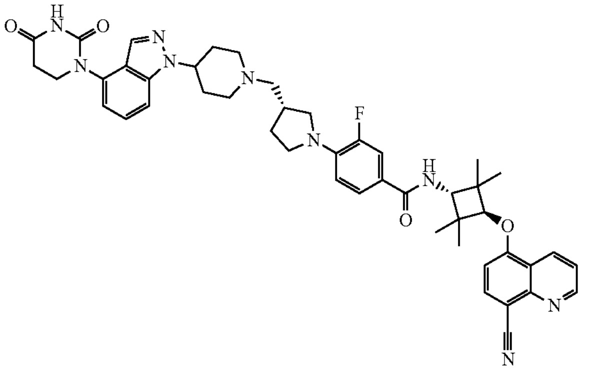 [SMILES: CC1(C)[C@H](NC(=O)c2ccc(N3CC[C@H](CN4CCC(n5ncc6c(N7CCC(=O)NC7=O)cccc65)CC4)C3)c(F)c2)C(C)(C)[C@H]1Oc1ccc(C#N)c2ncccc12]<br>N-((1r,3R)-3-((8-Cyanoquinolin-5-yl)oxy)-2,2,4,4-tetramethylcyclobutyl)-4-((R)-3-((4-(4-(2,4-dioxotetrahydropyrimidin-1(2H)-yl)-1H-indazol-1-yl)piperidin-1-yl)methyl)pyrrolidin-1-yl)-3-fluorobenzamide, Formic acid salt<br>1H NMR (400 MHz, DMSO-d6) δ 1.20 - 1.32 (m, 12 H) 1.69 (br dd, J = 12.13, 7.88 Hz, 1 H) 1.92 (br d, J = 11.51 Hz, 2 H) 2.04 - 2.35 (m, 6 H) 2.43 - 2.49(m, 2 H) 2.53 - 2.60 (m, 1 H) 2.78 (t, J = 6.63 Hz, 2 H) 3.00 - 3.16 (m, 2 H) 3.23 (br t, J = 7.38 Hz, 1 H) 3.43 - 3.52 (m, 2 H) 3.56 - 3.60 (m, 1 H) 3.87 (t, J = 6.63Hz, 2 H) 4.15 (d, J = 9.01 Hz, 1 H) 4.50 (s, 1 H) 4.64 (br t, J = 4.13 Hz, 1 H) 6.73 (t, J = 8.88 Hz, 1 H) 6.93 - 7.08 (m, 2 H) 7.40 (dd, J = 8.38, 7.38 Hz, 1 H) 7.55 -7.68 (m, 4 H) 7.74 (dd, J = 8.50, 4.25 Hz, 1 H) 8.01 (s, 1 H) 8.20 (s, 1 H) 8.29 (d, J = 8.26 Hz, 1 H) 8.74 (dd, J = 8.50, 1.75 Hz, 1 H) 9.09 (dd, J = 4.38, 1.63 Hz, 1H)<br>LCMS (formic B): Rt = 1.01 min, MH+ = 813 | D65 | D7 | Prep HPLC (formic); 38.3 mg, 23% yield |
| 35 | 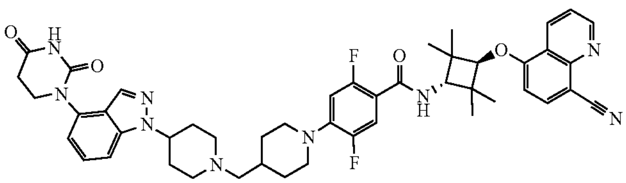 [SMILES: CC1(C)[C@H](NC(=O)c2cc(F)c(N3CCC(CN4CCC(n5ncc6c(N7CCC(=O)NC7=O)cccc65)CC4)CC3)cc2F)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)-2,5-difluorobenzamide<br>1H NMR (400 MHz, DMSO-d6) δ 10.46 (s, 1H), 9.11 (dd, J = 4.3, 1.8 Hz, 1H), 8.75 (dd, J = 8.5, 1.8 Hz, 1H), 8.30 (d, J = 8.3 Hz, 1H), 8.03 (s, 1H), 7.76 (dd, J = 8.5, 4.3 Hz, 1H), 7.71 - 7.64 (m, 2H), 7.45 - 7.36 (m, 2H), 7.05 (d, J = 7.3 Hz, 1H), 7.01 - 6.90 (m, 2H), 5.76 (s, 1H), 4.71 - 4.59 (m, 1H), 4.49 (s, 1H), 4.08 (d, J = 8.5 Hz, 1H), 3.88 (t, J = 6.6 Hz, 2H), 3.54 (br d, J = 12.3 Hz, 2H), 3.07 - 2.97 (m, 2H), 2.86 - 2.72 (m, 5H), 2.27 (br d, J = 7.0 Hz, 2H), 2.23 - 2.09 (m, 4H), 1.95 - 1.81 (m, 4H), 1.80 - 1.66 (m, 1H), 1.36 - 1.26 (m, 8H), 1.24 (s, 6H)<br>LCMS (formic B): Rt = 1.04 min, MH+ =845 | D69 | D7 | Silica chromatography (12 g, 0-40% [9:1 DCM:MeOH]/ DCM); 101 mg, quantitative yield |

-continued

| Ex | Name; Analytical | Aldehyde | Amine | Purification method; Mass, yield |
|---|---|---|---|---|
| 36 | 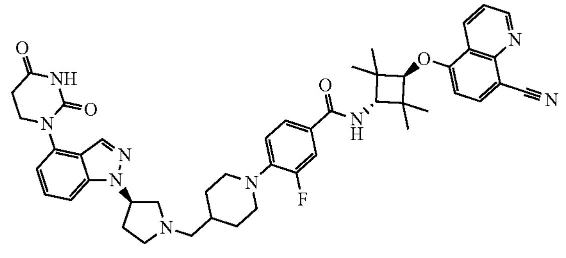 [SMILES: CC1(C)[C@H](NC(=O)c2ccc(N3CCC(CN4CC[C@@H](n5ncc6c(N7CCC(=O)NC7=O)cccc65)C4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-(((R)-3-(4-(2,4-dioxotetrahydropyrimidin-1(2H)-yl)-1H-indazol-1-yl)pyrrolidin-1-yl)methyl)piperidin-1-yl)-3-fluorobenzamide<br>1H NMR (400 MHz, DMSO-d6) δ 10.46 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.03 (s, 1H), 7.82 - 7.73 (m, 3H), 7.70 - 7.63 (m, 2H), 7.41 (dd, J = 8.4, 7.4 Hz, 1H), 7.13 - 7.04 (m, 2H), 6.97 (d, J = 8.5 Hz, 1H), 5.76 (s, 1H), 5.46 - 5.36 (m, 1H), 4.50 (s, 1H), 4.17 (d, J = 9.3 Hz, 1H), 3.89 (t, J = 6.6 Hz, 2H), 3.54 - 3.45 (m, 2H), 3.08 (br t, J = 8.8 Hz, 1H), 2.89 - 2.69 (m, 7H), 2.48 - 2.35 (m, 3H), 2.30 - 2.19 (m, 1H), 1.94 - 1.83 (m, 2H), 1.67 (br dd, J = 7.3, 3.3 Hz, 1H), 1.40 - 1.27 (m, 8H), 1.24 (s, 6H)<br>LCMS (formic B): Rt = 1.01 min, MH+ = 813 | D57 | D72 | Silica chromatography (12g, 0-40% [9:1 DCM: MeOH]/ DCM); 43.2 mg, 27% yield |
| 37 | 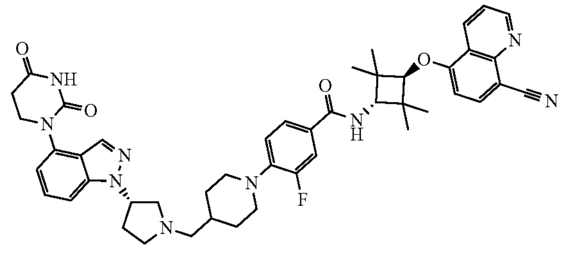 [SMILES: CC1(C)[C@H](NC(=O)c2ccc(N3CCC(CN4CC[C@H](n5ncc6c(N7CCC(=O)NC7=O)cccc65)C4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-(((S)-3-(4-(2,4-dioxotetrahydropyrimidin-1(2H)-yl)-1H-indazol-1-yl)pyrrolidin-1-yl)methyl)piperidin-1-yl)-3-fluorobenzamide<br>1H NMR (400 MHz, DMSO-d6) δ 10.46 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.03 (s, 1H), 7.82 - 7.73 (m, 3H), 7.70 - 7.62 (m, 2H), 7.41 (dd, J = 8.4, 7.4 Hz, 1H), 7.14 - 7.04 (m, 2H), 6.97 (d, J = 8.5 Hz, 1H), 5.76 (s, 1H), 5.45 - 5.36 (m, 1H), 4.50 (s, 1H), 4.17 (d, J = 9.3 Hz, 1H), 3.89 (t, J = 6.6 Hz, 2H), 3.50 (br dd, J = 9.3, 3.5 Hz, 2H), 3.08 (br t, J = 8.6 Hz, 1H), 2.89 - 2.69 (m, 7H), 2.48 - 2.35 (m, 3H), 2.30 - 2.20 (m, 1H), 1.93 - 1.84 (m, 2H), 1.74 - 1.61 (m, 1H), 1.41 - 1.27 (m, 8H), 1.24 (s, 6H)<br>LCMS (formic B): Rt = 1.01 min, MH+ = 813 | D57 | D28 | Silica chromatography (12g, 0-40% [9:1 DCM:MeOH]/ DCM); 64 mg, 41% yield |

-continued

| Ex | Name; Analytical | Aldehyde | Amine | Purification method; Mass, yield |
|---|---|---|---|---|
| 38 | 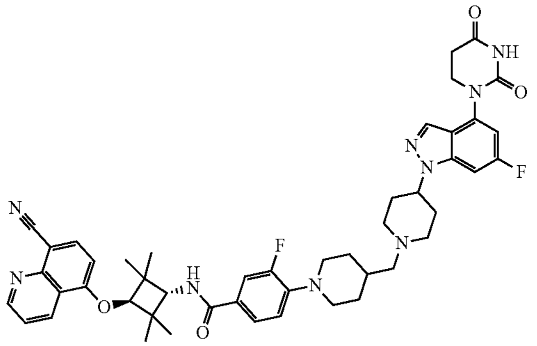 [SMILES: CC1(C)[C@H](NC(=O)c2ccc(N3CCC(CN4CCC(n5ncc6c(N7CCC(=O)NC7=O)cc(F)cc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-6-fluoro-1H-indazol-1-yl)piperidin-1-yl)methyl)piperidin-1-yl)-3-fluorobenzamide, Formic acid salt<br>1H NMR (400 MHz, DMSO-d6) δ ppm 1.21 - 1.35 (m, 14 H) 1.65 - 1.78 (m, 1 H) 1.82 - 1.98 (m, 4 H) 2.10 - 2.27 (m, 4 H) 2.29 - 2.35 (m, 2 H) 2.72 - 2.85 (m,4 H) 3.03 (br d, J = 8.76 Hz, 2 H) 3.51 (br d, J = 12.01 Hz, 2 H) 3.91 (t, J = 6.63 Hz, 2 H) 4.18 (d, J = 9.01 Hz, 1 H) 4.50 (s, 1 H) 4.62 (br s, 1 H) 6.93 - 7.06 (m, 2H) 7.07 - 7.17 (m, 1 H) 7.57 - 7.63 (m, 1 H) 7.63 - 7.72 (m, 2 H) 7.72 - 7.79 (m, 2 H) 8.04 (s, 1 H) 8.14 (s, 1 H) 8.31 (d, J = 8.25 Hz, 1 H) 8.75 (dd, J = 8.50,1.75 Hz, 1 H) 9.11 (dd, J = 4.25, 1.50 Hz, 1 H) 10.54 (s, 1 H)<br>LCMS (formic B): Rt = 1.02 min, MH+ = 844 | D57 | D88 | Prep HPLC (formic); 84.9 mg, 60% yield |
| 39 | 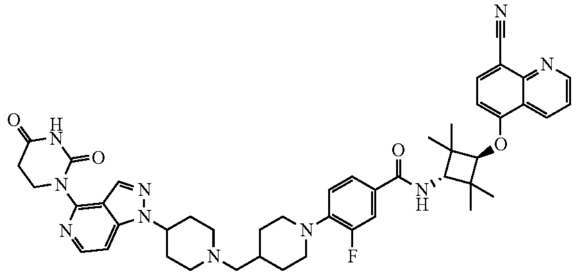 [SMILES: CC1(C)[C@H](NC(=O)c2ccc(N3CCC(CN4CCC(n5ncc6c(N7CCC(=O)NC7=O)nccc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide<br>LCMS (formic A): Rt = 0.86 min, MH+ = 827 | D57 | D119 | Prep HPLC (high pH); 28 mg, 7% yield |
| 40 | 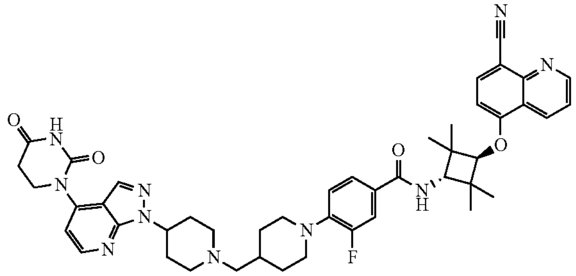 [SMILES: CC1(C)[C@H](NC(=O)c2ccc(N3CCC(CN4CCC(n5ncc6c(N7CCC(=O)NC7=O)ccnc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-pyrazolo[3,4-b]pyridin-1-yl)piperidin-1-yl)methyl)piperidin-1-yl)-3-fluorobenzamide, Hydrochloride<br>LCMS (high pH G): Rt = 3.16 min, MH+ = 827 | D57 | D108 | Prep HPLC (HCl); 20 mg, 6% yield |

-continued

| Ex | Name; Analytical | Aldehyde | Amine | Purification method; Mass, yield |
|---|---|---|---|---|
| 41 | 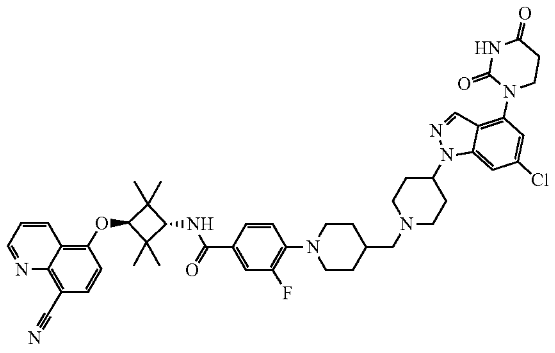 [SMILES: CC1(C)[C@H](NC(=O)c2ccc(N3CCC(CN4CCC(n5ncc6c(N7CCC(=O)NC7=O)cc(Cl)cc65)CC4)CC3)c(F)c2)C(C)(C)[C@H]1Oc1ccc(C#N)c2ncccc12]<br>4-(4-((4-(6-Chloro-4-(2,4-dioxotetrahydropyrimidin-1(2H)-yl)-1H-indazol-1-yl)piperidin-1-yl)methyl)piperidin-1-yl)-/-((1r,3r)-3-((8-cyanoquinolin-5-yl)oxy)-2,2,4,4-tetramethylcyclobutyl)-3-fluorobenzamide<br>1H NMR (400 MHz, DMSO-d6) δ 10.54 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.07 (s, 1H), 7.91 (s, 1H), 7.80 - 7.71 (m, 2H), 7.70 - 7.61 (m, 2H), 7.18 - 7.06 (m, 2H), 6.97 (d, J = 8.3 Hz, 1H), 5.76 (s, 1H), 4.77 - 4.62 (m, 2H), 4.50 (s, 1H), 4.18 (d, J = 9.0 Hz, 1H), 3.91 (t, J = 6.6 Hz, 2H), 3.51 (br d, J = 11.8 Hz, 2H), 3.00 (br d, J = 8.8 Hz, 3H), 2.84 - 2.70 (m, 5H), 2.31 - 2.24 (m, 2H), 2.24 - 2.05 (m, 5H), 1.96 - 1.80 (m, 5H), 1.79 - 1.65 (m, 1H), 1.40 - 1.27 (m, 9H), 1.24 (s, 6H)<br>LCMS (formic B): Rt = 1.04 min, MH+ = 861 | D57 | D122 | Silica chromatography (12g, 0-100% [9:1 DCM:MeOH]/ DCM);<br>81.1 mg,<br>48% yield |
| 42 | 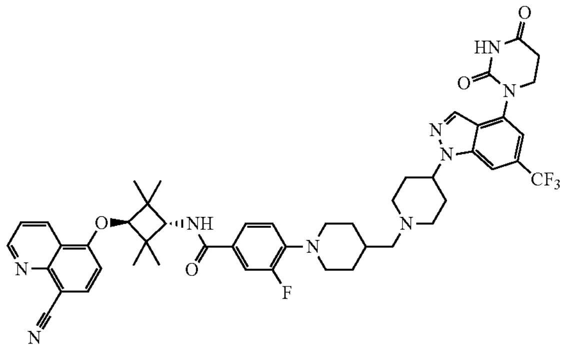 [SMILES: CC1(C)[C@H](NC(=O)c2ccc(N3CCC(CN4CCC(n5ncc6c(N7CCC(=O)NC7=O)cc(C(F)(F)F)cc65)CC4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-6-(trifluoromethyl)-1H-indazol-1-yl)piperidin-1-yl)methyl)piperidin-1-yl)-3-fluorobenzamide<br>1H NMR (400 MHz, DMSO-d6) δ 10.56 (s, 1H), 9.11 (dd, J = 4.3, 1.8 Hz, 1H), 8.75 (dd, J = 8.4, 1.6 Hz, 1H), 8.31 (d, J = 8.3 Hz, 1H), 8.24 (d, J = 17.0 Hz, 2H), 7.81 - 7.73 (m, 2H), 7.71 - 7.62 (m, 2H), 7.38 (s, 1H), 7.11 (t, J = 8.8 Hz, 1H), 6.98 (d, J = 8.5 Hz, 1H), 4.89 (br dd, J = 5.3, 2.8 Hz, 1H), 4.50 (s, 1H), 4.18 (d, J = 9.3 Hz, 1H), 3.95 (t, J = 6.6 Hz, 2H), 3.51 (br d, J = 11.8 Hz, 2H), 3.08 - 2.94 (m, 2H), 2.86 - 2.72 (m, 4H), 2.32 - 2.08 (m, 6H), 1.99 - 1.82 (m, 4H), 1.81 - 1.67 (m, 1H), 1.31 (s, 8H), 1.24 (s, 6H)<br>LCMS (formic B): Rt = 1.06 min, MH+ = 895 | D57 | D125 | Silica chromatography (12 g, 0-100% [9:1 DCM: MeOH]/ DCM); 96.6 mg, 54% yield |

-continued

| Ex | Name; Analytical | Aldehyde | Amine | Purification method; Mass, yield |
|---|---|---|---|---|
| 43 | 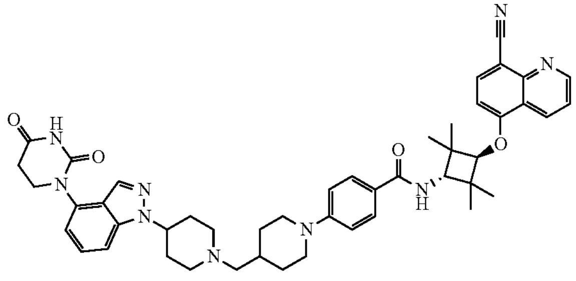 [SMILES: CC1(C)[C@H](NC(=O)c2ccc(N3CCC(CN4CCC(n5ncc6c(N7CCC(=O)NC7=O)cccc65)CC4)CC3)cc2)C(C)(C)[C@H]1Oc1ccc(C#N)c2ncccc12] N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indol-1-yl)piperidin-1-yl)methyl)piperidin-1-yl)benzamide, Formic acid salt<br>LCMS (formic A): Rt = 0.82 min, MH+ = 808 | D51 | D99 | MDAP (formic); 67 mg, 32% yield |
| 44 | 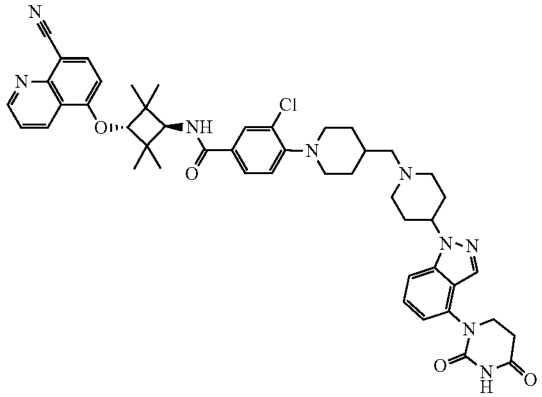 [SMILES: CC1(C)[C@H](NC(=O)c2ccc(N3CCC(CN4CCC(n5ncc6c(N7CCC(=O)NC7=O)cccc65)CC4)CC3)c(Cl)c2)C(C)(C)[C@H]1Oc1ccc(C#N)c2ncccc12] 3-Chloro-N-((1r,3r)-3-((8-cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)piperidin-1-yl)benzamide<br>1H NMR (400 MHz, DMSO-d6) δ 10.46 (s, 1H), 9.11 (dd, J = 4.3, 1.8 Hz, 1H), 8.75 (dd, J = 8.4, 1.6 Hz, 1H), 8.31 (d, J = 8.3 Hz, 1H), 8.03 (s, 1H), 7.93 (d, J = 2.0 Hz, 1H), 7.87 (d, J = 9.3 Hz, 1H), 7.84 - 7.74 (m, 2H), 7.67 (d, J = 8.5 Hz, 1H), 7.43 - 7.38 (m, 1H), 7.22 (d, J = 8.5 Hz, 1H), 7.05 (d, J = 7.3 Hz, 1H), 6.98 (d, J = 8.5 Hz, 1H), 4.72 - 4.60 (m, 1H), 4.50 (s, 1H), 4.18 (d, J = 9.0 Hz, 1H), 3.89 (t, J = 6.6 Hz, 2H), 3.46 - 3.37 (m, 2H), 3.09 - 2.95 (m, 2H), 2.83 - 2.67 (m, 4H), 2.34 - 2.26 (m, 2H), 2.26 - 2.09 (m, 4H), 2.01 - 1.83 (m, 4H), 1.81 - 1.68 (m, 1H), 1.42 - 1.28 (m, 8H), 1.25 (s, 6H).<br>LCMS (formic B): Rt = 1.02 min, MH+ = 843 | D76 | D7 | Prep HPLC (high pH); 96.4 mg, 49% yield |

-continued

| Ex | Name; Analytical | Aldehyde | Amine | Purification method; Mass, yield |
|---|---|---|---|---|
| 45 | 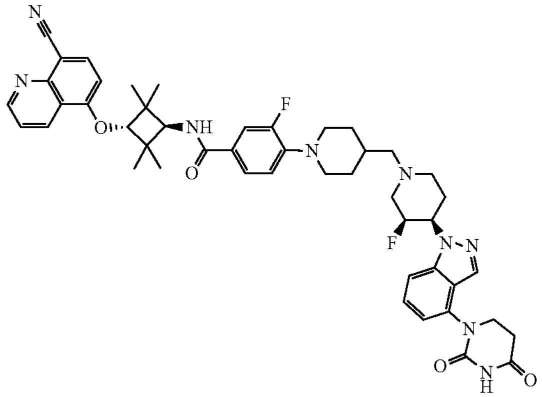 [SMILES: CC1(C)[C@H](NC(=O)c2ccc(N3CCC(CN4CC[C@@H](n5ncc6c(N7CCC(=O)NC7=O)cccc65)[C@@H](F)C4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-(((3S,4R)-4-(4-(2,4-dioxotetrahydropyrimidin-1(2H)-yl)-1H-indazol-1-yl)-3-fluoropiperidin-1-yl)methyl)piperidin-1-yl)-3-fluorobenzamide<br>1H NMR (400 MHz, DMSO-d6) δ 10.47 (s, 1H), 9.11 (dd, J = 4.3, 1.5 Hz, 1H), 8.75 (dd, J = 8.5, 1.8 Hz, 1H), 8.31 (d, J = 8.3 Hz, 1H), 8.03 (s, 1H), 7.80 - 7.62 (m, 5H), 7.46 - 7.37 (m, 1H), 7.17 - 7.06 (m, 2H), 6.97 (d, J = 8.3 Hz, 1H), 5.06 - 4.82 (m, 2H), 4.49 (s, 1H), 4.22 - 4.14 (m, 1H), 3.94 - 3.85 (m, 2H), 3.51 (br d, J = 10.0 Hz, 2H), 3.27 - 3.05 (m, 2H), 2.91 - 2.70 (m, 5H), 2.50 - 2.42 (m, 1H), 2.33 (br d, J = 1.8 Hz, 3H), 2.06 - 1.82 (m, 3H), 1.82 - 1.65 (m, 1H), 1.41 - 1.27 (m, 8H), 1.24 (s, 6H).<br>LCMS (formic B): Rt = 0.98 min, MH+ = 845. | D57 | D47 | Prep HPLC (high pH); 72.1 mg, 66% yield |
| 46 | 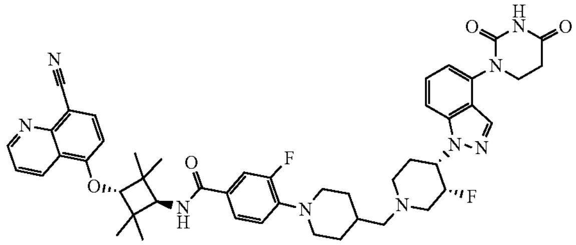 [SMILES: CC1(C)[C@H](NC(=O)c2ccc(N3CCC(CN4CC[C@H](n5ncc6c(N7CCC(=O)NC7=O)cccc65)[C@H](F)C4)CC3)c(F)c2)C(C)(C)[C@H]1Oc1ccc(C#N)c2ncccc12]<br>N-((1r,3r)-3-((8-Cyanoquinolin-5-yl)oxy)-2,2,4,4-tetramethylcyclobutyl)-4-(4-(((3R,4S)-4-(4-(2,4-dioxotetrahydropyrimidin-1(2H)-yl)-1H-indazol-1-yl)-3-fluoropiperidin-1-yl)methyl)piperidin-1-yl)-3-fluorobenzamide<br>1H NMR (400 MHz, DMSO-d6) δ 10.47 (s, 1H), 9.11 (dd, J = 4.3, 1.8 Hz, 1H), 8.75 (dd, J = 8.5, 1.8 Hz, 1H), 8.31 (d, J = 8.3 Hz, 1H), 8.07 - 7.99 (m, 1H), 7.82 - 7.62 (m, 5H), 7.42 (dd, J = 8.3, 7.5 Hz, 1H), 7.16 - 7.05 (m, 2H), 6.97 (d, J = 8.5 Hz, 1H), 5.11 - 4.77 (m, 2H), 4.55 - 4.46 (m, 1H), 4.22 - 4.12 (m, 1H), 3.89 (t, J = 6.6 Hz, 2H), 3.63 - 3.44 (m, 2H), 3.26 - 3.04 (m, 2H), 2.91 - 2.71 (m, 5H), 2.49 - 2.40 (m, 1H), 2.40 - 2.23 (m, 3H), 2.02 - 1.82 (m, 3H), 1.81 - 1.67 (m, 1H), 1.39 - 1.27 (m, 8H), 1.24 (s, 6H).<br>LCMS (formic B): Rt = 0.99 min, MH+ = 845 | D57 | D37 | Prep HPLC (high pH); 63.2 mg, 75% yield |

Example 47

N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-7H-pyrrolo[2,3-d]pyrimidin-7-yl)piperidin-1-yl)methyl)piperidin-1-yl)-3-fluorobenzamide

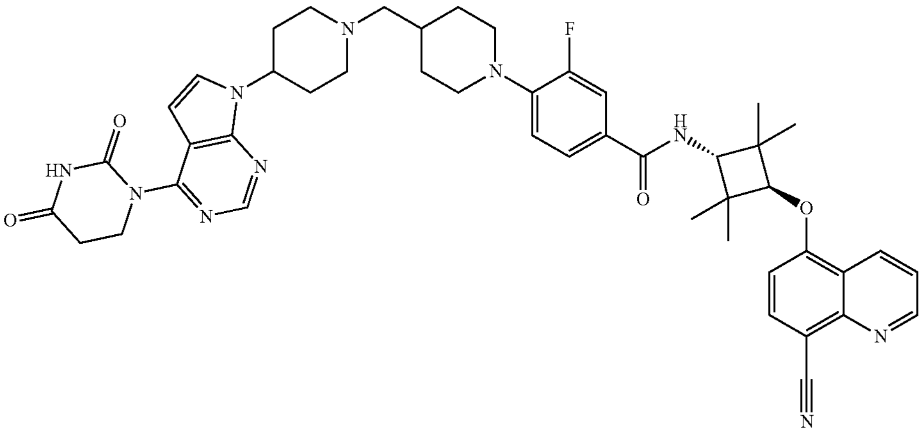 [SMILES: CC1(C)[C@H](NC(=O)c2ccc(N3CCC(CN4CCC(n5ccc6c(N7CCC(=O)NC7=O)ncnc65)CC4)CC3)c(F)c2)C(C)(C)[C@H]1Oc1ccc(C#N)c2ncccc12]

To a stirred solution of (1-(4-(((1r,3r)-3-((8-cyanoquinolin-5-yl)oxy)-2,2,4,4-tetramethylcyclobutyl)carbamoyl)-2-fluorophenyl)piperidin-4-yl)methyl methanesulfonate (may be prepared as described in Description 77, 361 mg, 522 μmol) in DMSO (2 mL) was added 1-(7-(piperidin-4-yl)-7H-pyrrolo[2,3-d]pyrimidin-4-yl)dihydropyrimidine-2,4(1H,3H)-dione (may be prepared as described in D113, 180 mg, 574 μmol) and DIPEA (273 μL, 1.57 mmol) then the mixture heated at 100° C. for 2 h. The reaction mixture was directly purified by MDAP (high pH), then the appropriate fractions were combined and concentrated under a stream of nitrogen to give the required product (56 mg, 13% yield) as a white solid. LCMS (high pH A): Rt=1.33 min, MH+=827.

Example 48

N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-1H-indazol-1-yl)piperidin-1-yl)methyl)-4-hydroxypiperidin-1-yl)-3-fluorobenzamide, Formic Acid Salt

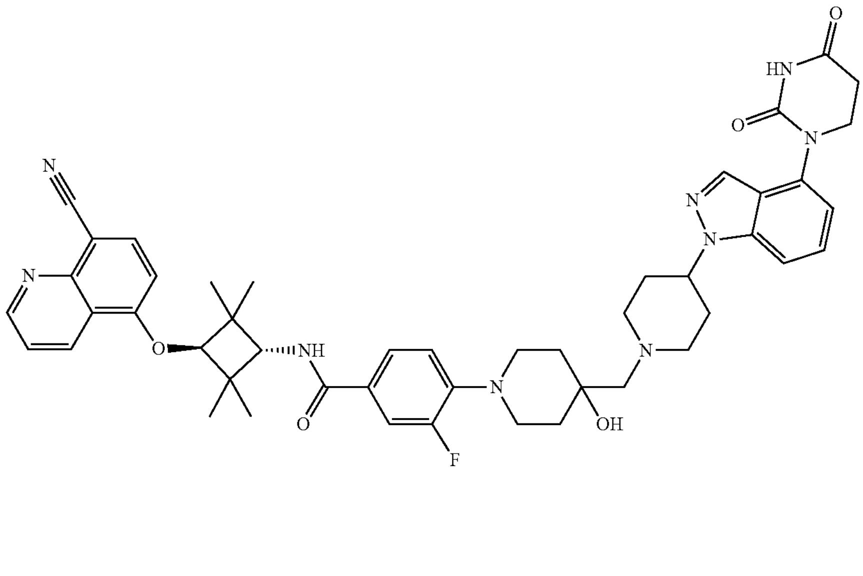 [SMILES: CC1(C)[C@H](NC(=O)c2ccc(N3CCC(O)(CN4CCC(n5ncc6c(N7CCC(=O)NC7=O)cccc65)CC4)CC3)c(F)c2)C(C)(C)[C@H]1Oc1ccc(C#N)c2ncccc12]

To a stirred solution of 4-(4-((4-(4-(2,4-dioxotetrahydropyrimidin-1(2H)-yl)-1H-indazol-1-yl)piperidin-1-yl)methyl)-4-hydroxypiperidin-1-yl)-3-fluorobenzoic acid, bis-trifluoroacetic acid salt (may be prepared as described in Description 81, 70.0 mg, 88.3 μmol), 5-((1r,3r)-3-amino-2,2,4,4-tetramethylcyclobutoxy)quinoline-8-carbonitrile dihydrochloride (may be prepared as described in D49, 35.8 mg, 97.1 μmol) and DIPEA (154 μL, 883 μmol) in DMF (0.5 mL) was added HATU (36.9 mg, 97.1 μmol) then the mixture was stirred at room temperature for 10 min. The reaction mixture was directly purified by MDAP (formic acid modifier gradient), then the appropriate fractions were combined and concentrated under a stream of nitrogen to give the required product (54.9 mg, 60% yield) as a white solid. LCMS (formic A): Rt=0.83 min, MH+=842.

Example 49

N-((1r,3r)-3-((8-Cyanoquinolin-5-yl)oxy)-2,2,4,4-tetramethylcyclobutyl)-4-(2-(4-(4-(2,4-dioxotetrahydropyrimidin-1(2H)-yl)-1H-indazol-1-yl)piperidin-1-yl)-7-azaspiro[3.5]nonan-7-yl)-3-fluorobenzamide

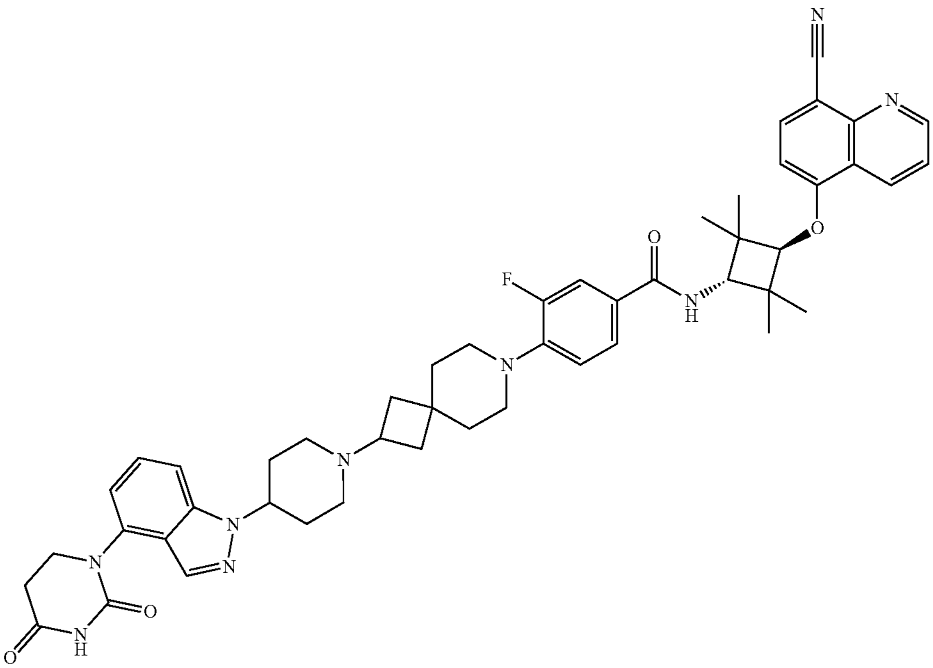 [SMILES: CC1(C)[C@H](NC(=O)c2ccc(N3CCC4(CC3)CC(N3CCC(n5ncc6c(N7CCC(=O)NC7=O)cccc65)CC3)C4)c(F)c2)C(C)(C)[C@H]1Oc1ccc(C#N)c2ncccc12]

To a solution of N-((1r,3r)-3-((8-cyanoquinolin-5-yl)oxy)-2,2,4,4-tetramethylcyclobutyl)-3-fluoro-4-(2-oxo-7-azaspiro[3.5]nonan-7-yl)benzamide (may be prepared as described in Description 84, 250 mg, 451 μmol) in DCM (2.5 mL) and methanol (2.5 mL) was added 1-(1-(piperidin-4-yl)-1H-indazol-4-yl)dihydropyrimidine-2,4(1H,3H)-dione (may be prepared as described in D7, 155 mg, 496 μmol) and sodium acetate (73.9 mg, 901 μmol), then the reaction mixture was stirred at room temperature for 3 h, then sodium cyanoborohydride (56.7 mg, 901 μmol) was added and the mixture was stirred for at room temperature for 16 h. The reaction mixture was concentrated, diluted with water (10 mL) and extracted with EtOAc (2×10 mL). The organic layers were combined, dried over sodium sulfate, filtered and concentrated in vacuo. The sample was purified by prep HPLC (high pH) then the appropriate fractions were combined and lyophilised to give the required product (60 mg, 16% yield) as a white solid. LCMS (high pH G): Rt=3.25 min, MH+=852.

Examples 50-51

General Procedure

To a solution of amine substrate (1 equivalent) and N-((1r,3r)-3-((8-cyanoquinolin-5-yl)oxy)-2,2,4,4-tetramethylcyclobutyl)-3-fluoro-4-(4-formylpiperidin-1-yl)benzamide (may be prepared as described in Description 57, 1 equivalent) in DCM:methanol (95:5, 0.05M) was added sodium triacetoxyborohydride (3 equivalents) then the mixture was stirred at room temperature for 18 h. The mixture was diluted with DCM and then washed with water. The aqueous layer was back-extracted twice with DCM, then the organic layers were combined, washed with brine, dried over sodium sulfate, filtered and the evaporated in vacuo. The sample was purified by prep HPLC (formic), then the appropriate fractions were combined and evaporated in vacuo. The sample was dissolved in DCM, then washed with $Na_2CO_3$ (10% aq.). The aqueous layer was back-extracted twice with DCM, then the organic layers were combined, dried over sodium sulfate, filtered and evaporated in vacuo to give the required product.

| Ex | Name; Analytical | Amine | Mass, yield |
|---|---|---|---|
| 50 | 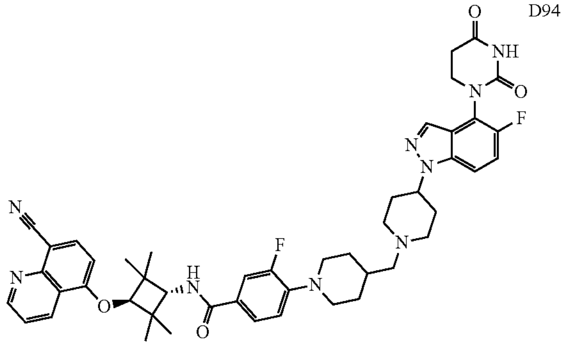<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-5-fluoro-1H-indazol-1-yl)piperidin-1-yl)methyl)piperidin-1-yl)-3-fluorobenzamide<br>LCMS (high pH C): Rt = 2.35 min, MH+ = 845 | D94 | 69.7 mg, 52% yield |
| 51 | 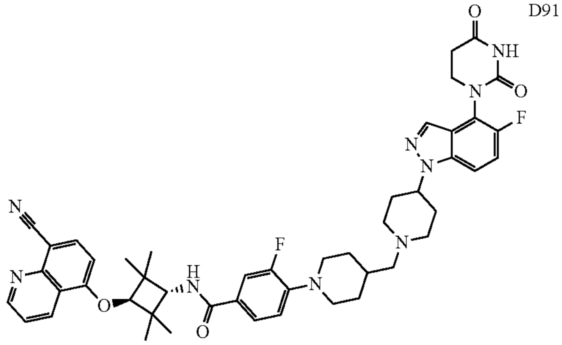<br>N-((1r,3r)-3-((8-Cyanoquinolin-5-yl)oxy)-2,2,4,4-tetramethylcyclobutyl)-4-(4-((4-(4-(2,4-dioxotetrahydropyrimidin-1(2H)-yl)-5-fluoro-1H-indol-1-yl)piperidin-1-yl)methyl)piperidin-1-yl)-3-fluorobenzamide<br>LCMS (high pH F): Rt = 2.78 min, MH+ = 844 | D91 | 56 mg, 51% yield |

Large Scale Preparation of N-((1r,3r)-3-(4-cyano-3-methoxyphenoxy)-2,2,4,4-tetramethylcyclobutyl)-4-(4-((4-(4-(2,4-dioxotetrahydropyrimidin-1 (2H)-yl)-1H-pyrazolo[4,3-c]pyridin-1-yl) piperidin-1-yl) methyl) piperidin-1-yl)-3-fluorobenzamide

Stage 1—Preparation of ethyl 3-fluoro-4(4-(hydroxymethyl)piperidin-1-yl)benzoate To a solution of ethyl 3,4-difluorobenzoate (28.2 kg, 1.0 eq.) in N-methyl-2-pyrrolidone (5 V), 4-piperidinemethanol (19.25 kg, 1.1 eq.) and $Na_2CO_3$ (0.5 eq.) were added. The mixture was heated to 90-100° C., then stirred at 90-100° C. until the reaction was complete. The resulting reaction mixture was cooled to 20-30° C. Process water (5 V) was charged into the reaction mixture at 20-30° C. The mixture was heated to 40-50° C. and stirred for 0.5-1 hour. After cooling to 25-35° C., seed crystal (0.08 kg) was added (seed crystals may be prepared using this process without seeding). Process water (15 V) was then charged dropwise over 6 hours at 25-35° C. The resultant mixture was cooled to 0-10° C. and stirred for 8 hours. The mixture was filtered and rinsed with process water (3 V). The wet cake was dried under vacuum at 40-55° C. to give the title compound as a yellow solid (42.5 kg, assay 95.1%, net 40.4 kg).

Stage 2—Preparation of 3-fluoro-4-(4-(hydroxymethyl)piperidin-1-yl)benzoic Acid To a solution of ethyl 3-fluoro-4-(4-(hydroxymethyl)piperidin-1-yl)benzoate (40.4 kg, 1.0 eq) in ethanol (10 V), 2M NaOH (1.5 eq) was added dropwise at 20-30° C. The mixture was stirred at 20-30° C. until the reaction was complete. 1N HCl was charged into the reaction mixture at 20-30° C. to adjust the pH to 3-5. Process water (5 V) was charged at 20-30° C. The resulting suspension was stirred at 20-30° C. for 1-3 hrs, then cooled to 0-10° C. and stirred for 4-8 hours. The mixture was filtered and rinsed with process water (3 V). The wet cake was dried under vacuum at 40-50° C. to give the title compound as light yellow solid (34.5 kg).

Stage 3—Preparation of 3-(hydroxyamino)-2,2,4,4-tetramethylcyclobutan-1-one To a mixture of tetramethyl-1,3-cyclobutanedione (122.6 kg, 1.0 wt) and sodium acetate (71.0 kg, 1.0 eq.) in tetrahydrofuran (626 L+13.7 L, 5 V), hydroxylamine hydrochloride solution ($NH_2OH{\cdot}HCl$ (60.0 kg, 1.0 eq.) in water (362 L, 3 V) was added over 3 hours at 25±5° C. (rinsing in with process water (6 L). The reaction was stirred at 25±5° C. for 10-16 hours, where analysis showed the reaction was complete. Methyl tert-butyl ether (607 L, 5 V) was added. The mixture was stirred and separated at 25±5° C. 25% aq. NaCl (558 kg, 4.55 wt) was added to the organic phase and then 10% aq. $Na_2CO_3$ (556 kg, 4.5 wt.) was added to adjust the pH to 7-8. The mixture was stirred, separated and the resulting organic phase concentrated to 2-3 V under vacuum below 45° C. Isopropyl alcohol (611 L, 5 V) was charged. The concentration and isopropyl alcohol charging operation was repeated twice (using isopropyl alcohol 2×611 L). The mixture was adjusted to 25±5° C., stirred for 1 hour, then filtered to give 3-(hydroxyamino)-2,2,4,4-tetramethylcyclobutan-1-one solution in isopropyl alcohol (filtrate 1002 kg, assay: 11.0%; net: 110.22 kg). The wet cake was washed with isopropyl alcohol (204 L) to give 3-(hydroxyamino)-2,2,4,4-tetramethylcyclobutan-1-one isopropyl alcohol rinse solution (158.0 kg, assay: 0.6%, net: 0.95 kg).

Stage 4—Preparation of 3-hydroxy-2,2,4,4-tetramethylcyclobutan-1-one Oxime

To an isopropyl alcohol solution of 3-(hydroxyamino)-2,2,4,4-tetramethylcyclobutan-1-one (1166 kg, net 111.2 kg, 1.0 eq.), $NaBH_4$ (12.90 kg, 0.4 eq.) was added in portions at 10-25° C. (rinsing with 7.6 L isopropyl alcohol). The mixture was warmed and stirred at 20±5° C. until analysis showed reaction was completed (3 hours). The reaction mixture was quenched with water (429 L, 4 V) slowly at 10-25° C. then adjusted with 5% aq. $H_3PO_4$ to pH 5-8 (132 kg, 1.2 wt), rinsing in with process water (10 L). The mixture was stirred at 20±5° C. for 15-45 mins, then 15% aq. NaOH (624 kg, 5.6 wt) and 2-methyltetrahydrofuran (617 L, 5.5 V) were charged. The mixture was stirred at 20±5° C. for 1-2 hours and then filtered. The wet cake was washed with 2-methyltetrahydrofuran (71.4 L). The obtained filtrates were combined, stirred and separated. The aqueous phase was extracted with 2-methyltetrahydrofuran (2×618 L). The organic solutions were combined, washed with 25% aq. NaCl (608 kg, 5.5 wt) and then concentrated to 2-3 V under vacuum below 50° C. 2-Methyltetrahydrofuran (226 L, 2 V) was added to rinse the reactor wall and then methylcyclohexane (733 L, 6.5 V) was added. The mixture was concentrated to 2-3 V under vacuum below 50° C. Methylcyclohexane (988 L, 9 V) was added over 2 hours. The mixture was cooled to 5±5° C., stirred for 6 hours and then filtered. The wet cake was washed with methylcyclohexane (2×110 L) and then dried under vacuum at 40±5° C. to give the title compound as white solid (97.75 kg).

Stage 5/6—Preparation of (1r,3r)-3-amino-2,2,4,4-tetramethylcyclobutan-1-ol, Phosphoric Acid Salt To a mixture of Raney Ni (12.4 kg, 0.3 wt.) and tetrahydrofuran (396 L, 10 V), 3-hydroxy-2,2,4,4-tetramethylcyclobutan-1-one oxime (40.4 kg, 1.0 eq.) was added under nitrogen protection. The mixture was degassed under vacuum and purged with nitrogen for three times and then swapped with hydrogen. The mixture was warmed and stirred at 35±5° C. under hydrogen (pressure: 0.35 f 0.1 MPa) for 8-16 hours until analysis showed the reaction was completed, then filtered through diatomite (12.1 kg, 0.3 wt.) to give 3-amino-2,2,4,4-tetramethylcyclobutan-1-ol as a solution in tetrahydrofuran (391.4 kg, assay 4.5%, net 17.61 kg). The cake was rinsed with tetrahydrofuran (2×60 L) to give 3-amino-2,2,4,4-tetramethylcyclobutan-1-ol rinse solution in tetrahydrofuran (103.0 kg, assay 0.9%, net 0.927 kg).

The tetrahydrofuran solutions of 3-amino-2,2,4,4-tetramethylcyclobutan-1-ol from two batches were combined (1213.4 kg, net 44.12 kg, 1.0 eq.) then concentrated to 2-3 V under vacuum below 45° C., then ethanol (697 L) was charged. The mixture was concentrated to 2-3 V under vacuum below 45° C., then ethanol (658 L) and methanol (470 L) were charged. $H_3PO_4$ solution in ethanol (69.9 kg of $H_3PO_4$ dissolved in 478 L of ethanol was added at 60±5° C. over 9 hours followed by rinse of ethanol (14 L). The mixture was stirred at 60±5° C. for 9 hours, then cooled to 20±5° C. over 3 hours, aged at 20±5° C. for 5 hours and then filtered. The wet cake was washed with ethanol (2×246 L) and then dried under vacuum at 45±5 to give the title compound as a white solid (64.1 kg, 43.9% yield).

Stage 7—Preparation of tert-butyl ((1r,3r)-3-hydroxy-2,2,4,4-tetramethylcyclobutyl)carbamate To a solution of the phosphoric acid salt of (1r,3r)-3-amino-2,2,4,4-tetramethylcyclobutan-1-ol (42.3 kg, 1.0 eq.) in 2-methyltetrahydrofuran (339 L, 8.0 V) and water (149 L, 3.5 V), an aqueous solution of $K_2CO_3$ (48.7 kg, 2.0 eq.) in water (186 L, 4.4 V)) was added at 5-15° C. followed by a water (4.4 L) rinse. The reaction mixture was stirred at 0-15° C. for 0.5 hour and then di-tert-butyl dicarbonate (42.2 kg, 1.1 eq.) was added at 0-15° C. followed by a rinse of 2-methyltetrahydrofuran (5.2 L). The reaction mixture was stirred at 20±5° C. for 2-6 hours until analysis showed the reaction was complete. Methylcyclohexane (166 L, 3.9 V) was added to the reaction mixture. The mixture was stirred and separated at 15-25° C. The organic layer was washed with 10% aq. $K_2CO_3$ (173.0 kg, 4.0 wt) and water (2×175 L). The resulting organic phase was offloaded, the reactor washed with 2-methyltetrahydrofuran and the organic phase transferred back to the reactor through an in-line filter. The organic phase was concentrated to 3 V under vacuum below 45° C. and then methylcyclohexane (298 L, 7 V) was added. The mixture was concentrated to 3 V under vacuum below 45° C. and then methylcyclohexane (301 L, 7 V) was added. The mixture was concentrated to 4 V under vacuum below 45° C. and then methylcyclohexane (383 L, 9 V) was added. The mixture was warmed and stirred at 50±5° C. for 1 h, then cooled slowly over 10 hours to 5±5° C., aged for 10 hours, then filtered. The wet cake was washed with methylcyclohexane (118 L, 2.8 V) and then dried under vacuum at 40±5° C. to give the title compound as a white solid (38.0 kg, 89.9% yield).

Stage 8—Preparation of tert-butyl 4-(2-((benzyloxy)carbonyl)hydrazineyl)piperidine-1-carboxylate To a solution of tert-butyl 4-oxopiperidine-1-carboxylate (40.3 kg, 1.0 eq) in anhydrous ethanol (10-12 V), acetic acid (0.1 eq) and Z-benzyl carbazate (33.7 kg, 1.0 eq) were added at 20-30° C. The reaction mixture was stirred at 20-30° C. until the reaction was complete. $NaBH_4$ (1.5-2.0 eq) was added in portions into the reaction mixture at 15-25° C. over 6 hours. The reaction mixture was stirred at 15-25° C. until the reaction was complete. Aqueous acetic acid (50% w/w, 2.4 V) was added into the reaction mixture slowly below 25° C. over 2 hours. Process water (10 V) was charged into the reaction mixture at 20-30° C. followed by seed crystals (0.2 kg, seed crystals may be prepared using this process without seeding) and the mixture stirred for 3 hours at 20-30° C. Process water (12 V) was charged dropwise over 6 hours at 20-30° C. and the resulting mixture cooled to 0-10° C. and stirred for 4-8 hours. The mixture was filtered and rinsed with process water (3 V). The wet cake was dried under vacuum at 45-55° C. to give the title compound as a white solid (65.5 kg, 92.7% yield).

Stage 9/10—Preparation of tert-butyl 4-(4-chloro-1H-pyrazolo[4,3-c]pyridin-1-yl)piperidine-1-carboxylate To a solution of tert-butyl 4-(2-((benzyloxy)carbonyl) hydrazineyl)piperidine-1-carboxylate (49.5 k g, 1.0 eq) in ethanol (8.5V) was added acetic acid (1.0 eq) and wet Pd/C (0.02 wt., 10% wt %) under $N_2$. The reaction mixture was stirred under $H_2$ (0.14-0.35 MPa) at 20° C. for 9 hours until analysis of the reaction by HPLC showed completion. The mixture was filtered through diatomite, rinsing the wet cake with ethanol (2 V). The combined filtrates were used in the next step directly.

To the ethanol solution of tert-butyl 4-hydrazinylpiperidine-1-carboxylate (1.0 eq.) was added a solution of 2-chloro-4-iodonicotinaldehyde (32.0 kg, 0.85 eq.) in N-methyl-2-pyrrolidone (4 V). The reaction mixture was stirred at 20-30° C. for 4 h until analysis of the reaction by HPLC showed completion. The resulting solution was distilled using a wipe-film evaporator <25° C. to remove ethanol. The residue was stored at 0-10° C. under $N_2$ and used in the next step directly.

To a solution of tert-butyl (Z)-4-(2-((2-chloro-4-iodopyridin-3-yl)methylene)hydrazineyl)piperidine-1-carboxylate (1.0 eq) in N-methyl-2-pyrrolidone (5 V) was added anhydrous $K_3PO_4$ (1.4 wt.) at 20° C. The mixture was heated to 100° C. and stirred for 12 hours where analysis of the reaction by HPLC showed completion. The reaction mixture was cooled to 20-30° C. and water (2.3 V) was added slowly. The solution was then warmed to 45-55° C. and further water (3.4 V) added slowly. Seed crystals were added (0.5% wt., seed crystals may be prepared using this process without seeding), and the mixture stirred at 45-55° C. for 2 hours. After cooling to 20-30° C., water (13.2 V) was added slowly into the mixture over 4 hours. The resulting slurry was stirred at 20-30° C. for 4 hours, then filtered washing the cake with water (2 V).

The wet cake was dissolved in methyl tert-butyl ether (12 V) at 20-30° C. 10% aq. NaCl (2 V) was added and the mixture filtered through diatomite, rinsing with methyl tert-butyl ether (3 V). The phases were separated and the organic layer washed with 10% aq. NaCl (2 V). The organic layer decolourised by filtering through a CUNO at 20-30° C. for 8 hours. The CUNO was rinsed with further methyl tert-butyl ether (5 V) then the organic solution was concentrated to 2-3 V. Methyl tert-butyl ether (10 V) was added and the organic layer was concentrated again to 2-3 V. Further methy tert-butyl ether (10 V) was added and the organic layer concentrated to 2-3 V and stirred at 20-30° C. Seed crystals were added (0.3% wt. seed crystals may be prepared using this process without seeding), followed by addition of n-heptane (15 V) at 20-30° C. over 8 hours. The resulting slurry was stirred at 20-30° C. for 1 hour, warmed to 40-50° C. for 3 hours then cooled to −10 to 0° C. over 7 hours and stirred for a further 3 hours. The product was collected by filtration washing the filter cake with n-heptane (2 V). The wet cake was dried under vacuum at 45-55° C. for 12 hours to obtain the title compound as a yellow solid (23.0 kg, 48.2% yield).

Stage 11—Preparation of tert-butyl 4-(4-(2,4-dioxotetrahydropyrimidin-1(2H)-yl)-1H-pyrazolo[4,3-c]pyridin-1-yl)piperidine-1-carboxylate To a solution of tert-butyl 4-(4-chloro-1H-pyrazolo[4,3-c]pyridin-1-yl)piperidine-1-carboxylate (28.0 kg, 1.0 eq) and dihydrouracil (12.9 kg, 1.3 eq.) in 1,4-dioxane (15 V) was added di-μ-chlorobis(2'-amino-1,1'-biphenyl-2-yl-C,N) dipalladium(II) (0.025 eq.), XPhos (0.05 eq.) and $K_3PO_4$ (1.5 eq.). The reaction mixture was purged with N2 (×3) then heated 80-100° C. and stirred for 8 hours at this temperature until the reaction is complete by HPLC.

The reaction mixture was cooled, filtered through diatomite rinsing with 1,4-dioxane (4 V). The solvent was switched to EtOAc (18 V). The solution was washed twice with a mixture of 10% aq. N-acetyl cysteine (6 V) and 10% aq. $Na_2CO_3$ (3 V), then washed with water (4 V). The organic solution was concentrated to 2-3 V below 40° C., then dichloromethane (4 V) and n-heptane (6 V) were added at 20-30° C. and the mixture stirred for 1-3 hours. Further n-heptane (12 V) was added over 2 hours, the mixture stirred at 20-30° C. for 4-8 hours, then filtered and the filter cake washed with n-heptane (4 V). The wet cake was dried 40-50° C. for 16 hours to obtain the crude product.

The crude product was dissolved in dichloromethane (13.5 V) and the solution was cycled through a silica thiol column at 20-30° C. for 6-18 hours. After rinsing the column with dichloromethane (2 V), the organic solution was concentrated to 5-6 V below 40° C. n-Heptane (15 V) was added over 2 hours at 20-30° C., the mixture stirred for 4-8 hours, then the product was collected by filtration, washing the filter cake with n-heptane (4 V). The wet cake was dried at 40-50° C. for 16 hours to obtain the title compound as a grey solid (21.3 kg, 61.8% yield).

Stage 12—Preparation of 1-(1-(piperidin-4-yl)-1H-pyrazolo[4,3-c]pyridin-4-yl)dihydropyrimidine-2,4 (1H,3H)-dione Dihydrochloride To a solution of tert-butyl 4-(4-(2,4-dioxotetrahydropyrimidin-1(2H)-yl)-1H-pyrazolo[4,3-c]pyridin-1-yl)piperidine-1-carboxylate (21.3 kg, 1.0 eq.) in dichloromethane (15 V) was added 4M HCl in ethyl acetate (9.3 wt., 16 eq.) at 20-30° C. The resulting suspension was heated to 35-45° C. then stirred at this temperature for 12 h. The reaction mixture was cooled to 25-35° C. then filtered, washing the cake with ethyl acetate (3 V). The wet cake was charged back to the reactor and slurried in ethanol (15 V) at 45-55° C. for 12 hours. The slurry was cooled to 25-35° C. then filtered, washing the cake with ethanol (3 V). The wet cake was dried at 50-60° C. for 24 hours to give the title compound as a off-white solid (15.6 kg, 78.4% yield.

Stage 13—Preparation of tert-butyl ((1r,3r)-3-(4-cyano-3-methoxyphenoxy)-2,2,4,4-tetramethylcyclobutyl)carbamate To a solution of tert-butyl ((1r,3r)-3-hydroxy-2,2,4,4-tetramethylcyclobutyl)carbamate (7.6 kg, 1.0 eq) in dimethylsulfoxide (3.2 V) and tetrahydrofuran (1.3 V) at 15-25° C. was added 4-fluoro-2-methoxybenzonitrile (5.0 kg, 1.05 eq.) followed by NaOH (2.1 eq.) in portions under $N_2$. The reaction mixture was stirred at 25-35° C. for 16-24h until the reaction was complete by HPLC. The mixture was quenched by addition of 10% aq. $H_3PO_4$ (2-V) below 25° C. to adjust the pH to 8-9. Process water (10V) was then added at 20-30° C. over 2 hours and the resulting mixture stirred for a further 4-8 hours. The product was collected by filtration, washing the cake washed with $H_2O$ (3 V) then at 45-55° C. to give the title compound as off-white solid (10.4 kg, 89.0% yield).

Stage 14—Preparation of 4-((1r,3r)-3-amino-2,2,4,4-tetramethylcyclobutoxy)-2-methoxybenzonitrile To a mixture of tert-butyl ((1r,3r)-3-(4-cyano-3-methoxyphenoxy)-2,2,4,4-tetramethylcyclobutyl)carbamate (20.4 kg, 1.0 eq) in methanol (8 V) was added 35% aq. Ha (2.3 wt., 8.0 eq) slowly at 20-30° C. under $N_2$. The mixture was warmed to 35-45° C. and stirred for 8-12 hours until the reaction was complete by HPLC. The solution was cooled to 15-25° C. and water (3 V) added. The mixture was treated with 10% aq. NaOH (8-12 V) below 25° C. to adjust the pH to 8-10. The resulting slurry was stirred at 15-25° C. for 4-8 hours then filtered, washing with water (3 V). The isolated solid was dried at 50° C. for 16-24 hours to give the title compound as an off-white solid (14.4 kg, 96.5% yield).

Stage 15—Preparation of N-((1r,3r)-3-(4-cyano-3-methoxyphenoxy)-2,2,4,4-tetramethylcyclobutyl)-3-fluoro-4-(4-(hydroxymethyl)piperidin-1-yl)benzamide To a stirred solution of 3-fluoro-4-(4-(hydroxymethyl) piperidin-1-yl)benzoic acid (14.1 kg, 1.05 eq) and 4-((1r, 3r)-3-amino-2,2,4,4-tetramethylcyclobutoxy)-2-methoxybenzonitrile (13.6 kg, 1.0 eq.) in N-methyl-2-pyrrolidone (5 V) at 15-25° C. was added diisopropylethylamine (1.5 eq) followed by O-(7-Azabenzotriazol-1-yl)-N,N,N',N'-tetramethyluronium hexafluorophosphate (HATU, 1.2 eq.). The reaction mixture was stirred for 2 hours until the reaction was complete by HPLC. Water (2.5 V) was added followed by seed crystals (0.03 kg, seed crystals may be prepared using this process without seeding) at 15-25° C. After stirring at 15-25° C. for 1-3 hours, water (9.5 V) was added over 2 hours at 20-30° C. and the resulting mixture stirred at 20-30° C. for 4-8 hours. The slurry was filtered and the filter cake washed with water (4 V). The wet cake was dried at 50° C. for 16-24 hours to give a crude solid.

The crude solid was suspended in ethyl acetate (5 V) and heated to 70-80° C. then held at this temperature for 6-10 hours. After cooling to −10-0° C. over 8 hours, the resulting slurry was stirred for a further 4 hours then filtered, washing the cake with 1:1 ethyl acetate:Methylcyclohexane (3 V). The isolated solid was dried at 40-50° C. to give the title compound as a light pink solid (20.9 kg, 82.7% yield).

Stage 16—Preparation of N-((1r,3r)-3-(4-cyano-3-methoxyphenoxy)-2,2,4,4-tetramethylcyclobutyl)-3-fluoro-4-(4-formylpiperidin-1-yl)benzamide To a mixture of N-((1r,3r)-3-(4-cyano-3-methoxyphenoxy)-2,2,4,4-tetramethylcyclobutyl)-3-fluoro-4-(4-(hydroxymethyl)piperidin-1-yl)benzamide (20.8 kg, 1.0 eq.) and N,N-diisopropylethylamine (6.0 eq) in acetonitrile (11 V) and dimethylsulfoxide (3 V) at −20 to −5° C., was added sulfur trioxide pyridine complex (3.0 eq) in portions over 2 hours. The reaction mixture was stirred at −20 to −5° C. for 2-4 hours, monitoring for reaction completion by HPLC. Water (2V) was added as quench into the reaction mixture below 0° C., then the mixture was adjusted to 20-30° C. and water (18 V) was added over 2 hours. The resulting slurry was stirred for 4-8 hours then filtered, washing the filter cake with water (3 V). The wet cake was dried at 40-50° C. to give the title compound as an off-white solid (19.1 kg, 92.2% yield).

Stage 17—Preparation of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide 1-(1-(Piperidin-4-yl)-1H-pyrazolo[4,3-c]pyridin-4-yl)dihydropyrimidine-2,4(1H,3H)-dione dihydrochloride (13.7 kg, 1.1 eq) and sodium acetate (1.2 eq) are suspended in dichloromethane (20 V) and methanol (4 V) at 20-30° C. N-((1r,3r)-3-(4-Cyano-3-methoxyphenoxy)-2,2,4,4-tetramethylcyclobutyl)-3-fluoro-4-(4-formylpiperidin-1-yl)benzamide (17.0 kg, 1.0 eq) is added to the suspension and the mixture is cooled to 0-10° C. Sodium triacetoxyborohydride (STAB, 2.0 eq) is added in >10 portions at 0-10° C. under $N_2$. The mixture is stirred for 2 hours at 0-10° C., monitoring for reaction completion by HPLC. After quenching by addition of purified water (5 V) at 0-10° C., the mixture is warmed to 20-30° C. and the layers allowed to separate. The organic phase was washed with 5% aq. $Na_2CO_3$ solution (7.6 wt.) at 20-30° C. The organic phase was diluted with DCM (9.7 V) and then methanol (1.0 V) followed by purified water (5 V) are added. After stirring the layers were separated, the organic phase transferred back to the reactor with a DCM (0.5 V) line wash, and methanol (0.8 V) added. The mixture is stirred at 20-30° C. to get a clear solution which is then clarified by filtration followed by with a DCM/methanol (18/1 v/v, 0.8 V) line wash. The solution is concentrated to 8-10 V under vacuum below 35° C. and DCM (2.0 V) is added to rinse the reactor wall. The suspension is heated to 30-40° C., stirred for 1.5 hours, then cooled to 20-30° C. and n-heptane (6.0 V) added at 20-30° C. over 2.5 hours. The resulting slurry is stirred at 20-30° C. for 11 hours, then filtered washing the cake with methanol (2.8 V). The wet cake is dried under vacuum at 45-55° C. for 66 hours to give the title compound as a white solid (24.1 kg, 89.3% yield).

Preparation of Crystalline N-((1r,3r)-3-(4-Cyano-3-methoxyphenoxy)-2,2,4,4-tetramethylcyclobutyl)-4-(4-((4-(4-(2,4-dioxotetrahydropyrimidin-1 (2H)-yl)-1H-pyrazolo[4,3-c]pyridin-1-yl) piperidin-1-yl) methyl) piperidin-1-yl)-3-fluorobenzamide Crude N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide was dissolved in dichloromethane (8.5V) and methanol (1V). The solution was filtered and the filtrate was washed with 5% $Na_2CO_3$ (5V) followed by water (3V). The organic phase was then stirred at 20-30° C. for 20 mins after which time material precipitated. The suspension was aged for 18 hours. n-Heptane (7.8V) was added and the suspension filtered and washed with n-heptane (2.9V). The wet cake was dried under vacuum at 45-55° C. for 76 hours. A portion of the purified material was crystallised from dichloromethane/methanol/n-heptane (20V/4V/8V).

Characterisation of Crystalline N-((1r,3r)-3-(4-Cyano-3-methoxyphenoxy)-2,2,4,4-tetramethylcyclobutyl)-4-(4-((4-(4-(2,4-dioxotetrahydropyrimidin-1 (2H)-yl)-1H-pyrazolo[4,3-c]pyridin-1-yl) piperidin-1-yl)methyl) piperidin-1-yl)-3-fluorobenzamide Crystalline N-((1r,3r)-3-(4-Cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide was characterised using X ray powder diffraction (XRPD). The XRPD data was acquired on a PANalytical Empyream X-ray powder diffractometer. The parameters were as follows:

X-ray reflection: Cu Kα

Scan range (°2theta): 2.0 to 40.0

Step size: (°2theta/step): 0.0263

Kα1 (Å): 1.540597, Kα2 (Å): 1.544426
Kα2/Kα1 Intensity ratio: 0.50
Voltage: 45 (WV)
Current: 40 (mA)

The XRPD spectrum of the material is shown in FIG. 1. Characteristic peaks for the diffractogram are:

| Pos. [°2θ] | d-spacing [Å] | Height [cts] |
|---|---|---|
| 6.4443 | 13.71596 | 24567.65 |
| 16.7139 | 5.30439 | 15309.35 |
| 17.357 | 5.10927 | 10941.25 |

Systemic Exposure of N-((1r,3r)-3-(4-Cyano-3-methoxyphenoxy)-2,2,4,4-tetramethylcyclobutyl)-4-(4-((4-(4-(2,4-dioxotetrahydropyrimidin-1 (2H)-yl)-1H-pyrazolo[4,3-c]pyridin-1-yl) piperidin-1-yl) methyl) piperidin-1-yl)-3-fluorobenzamide Systemic exposure of various forms of N-((1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl) piperidin-1-yl)-3-fluorobenzamide were assessed following oral administration of 30 mg/kg of a suspension formulation (1% methylcellulose (aq)) or following oral administration of 35 mg/kg of a suspension formulation (100% PEG400) in the male Wistar Han rat. Spray dried dispersions (SDD) with particular polymers and/or surfactants were included. The sampling period was 72 hours, and the data is reported in the attached table as mean±SD (n=3).

| Form | $C_{max}$ (ng/mL) | $T_{max}$ (h) | $AUC_{0-t}$ (ng · h/mL) | Dose Normalised $AUC_{0-t}$ (ng · h/mL)/ (mg/kg | *Estimated Bioavailability (%) |
|---|---|---|---|---|---|
| Formate Salt (30 mg/kg in 1% methylcellulose (aq.)) | 318 ± 50 | 8.0 ± 0.0 | 7220 ± 1220 | 240 ± 38 | 26 |
| Formate Salt (35 mg/kg in 100% PEG400) | 849 ± 98 | 8.7 ± 3.0 | 26200 ± 1750 | 744 ± 66 | 80 |
| Crystalline API (30 mg/kg in 1% methylcellulose (aq.)) | 185 ± 76 | 7.3 ± 1.2 | 4380 ± 1450 | 148 ± 49 | 16 |
| Crystalline API (35 mg/kg in 100% PEG400) | 420 ± 123 | 9.3 ± 2.3 | 10700 ± 3370 | 309 ± 98 | 33 |
| SDD 1:4 API:HPMCAS-LG[1] (30 mg/kg in 1% methylcellulose (aq.)) | 313 ± 54 | 6.9 ± 4.4 | 7940 ± 2940 | 263 ± 99 | 28 |
| SDD 1:3.5:0.5 API:HPMC-AS HG[2]:SLS[3] (30 mg/kg in 1% methylcellulose (aq.)) | 356 ± 134 | 5.3 ± 1.2 | 9260 ± 4120 | 312 ± 142 | 34 |

*comparison of dose normalised $AUC_{0-t}$ against an IV administered dose of 0.5 mg/kg
[1]HPMCAS-LG—Hypromellose acetate succinate, 1000 μm, soluble pH > 5.5
[2]HPMC-AS HG Hypromellose acetate succinate 1000 μm, soluble pH > 6.5
[3]SLS = sodium lauryl sulfate The table shows that the use of spray dried dispersions can increase exposure of N-(1r,3r)-3-(4-cyano-3-methoxyphenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide (the crystalline API). Oral exposure achieved using 30 mg/kg SDD 1:4 API:HPMCAS-LG or SDD 1:3.5:0.5 API:HPMC-AS HG:SLS in 1% methylcellulose (aq.) is broadly similar to that achieved with the 35 mg/kg crystalline API formulated in 1000/PEG400 (polyethylene glycol 400).

Biological Data

Androgen Receptor Degradation Assay Protocol

Degradation of Androgen Receptor protein in human LnCaP cells treated with PROTACs was quantified using the Nano-Glo® HiBiT Lytic Detection System (Promega) in 384 well assay plate format. A clonal LnCaP derived cell line was first established in which the AR gene was modified, using CRISPR/Cas9 editing, so the expressed AR protein included an 11 amino acid HiBiT tag at its amino-terminus. 10 mM DMSO stock solutions of PROTACs were prepared and diluted across an 11 concentration, 3 fold increment range, and 25 nL dispensed into a white opaque bottomed 384 well assay plate (Thermofisher) using an acoustic ECHO dispenser (Labcyte). Cells were grown in cell culture medium (RPMI 1640 supplemented with 15% FBS, penicillin 50U/mL and streptomycin 50 ug/mL (Thermofisher)). For the assay, cells were detached from flask and resuspended with assay medium (FluoroBrite™ DMEM supplemented with 10% heat inactivated FBS, penicillin 50U/mL and streptomycin 50 ug/mL (Thermofisher)). The cell suspension was centrifuged at 400 g for 5 min and the pellet resuspended in assay medium. 25 μL of cell suspension containing 10,000 cells was dispensed into each well of the assay plate containing a serial dilution of test compounds, which was then incubated for 18 h at 37° C./5% $CO_2$. Control wells were included on each assay plate, with assay medium without cells being the no AR remaining 100% effect control, and cells treated with DMSO vehicle only, without PROTAC, the 0% effect control. 25 μL of Nano-Glo® HiBiT lysis buffer supplemented with LgBiT protein and Nano-Glo® substrate (Promega) was added to each well and the plate shaken at 500 rpm for 10 min at room temperature. The intensity of luminescence was measured using a PHERAstar microplate reader (BMG Labtech) and the % AR protein remaining in each well calculated by normalising the raw luminescence value to the above control wells. Parameters corresponding to the potency and efficacy estimates of the PROTACs were obtained from these normalised luminescence values using software (IDBS ActivityBase). These included the $DC_{50}$ (concentration at which 50% of protein was degraded in M) and the $D_{max}$ (maximal degradation, in %) estimates. Two versions of the $DC_{50}$, called relative $DC_{50}$ and absolute $DC_{50}$, were generated. These are the inflection point of a fitted 4 parameter sigmoidal response curve and the interpolated concentration of PROTAC corresponding to 50% of the protein being degraded, respectively. The corresponding $pDC_{50}$ is reported as $-\log_{10}$(relative $DC_{20}$). The $D_{max}$ parameter was the maximum experimentally observed degradation and the asymptote max parameter the fitted response curve asymptote maximum.

The effects of PROTACs on cell viability were estimated by measuring cellular ATP levels using the CellTiter-Go® Luminescent Cell Viability Assay (Promega). ATP assays were conducted in parallel with AR HiBiT assays on a separate assay plate on the same day, following the same general procedure detailed above.

Results

Examples 1-51 were tested in the Androgen Receptor Degradation Assay.

Examples 1-51 exhibited a mean relative $pDC_{50}$ of ≥7.0.

Examples 2, 5-9, 11-13, 17-22, 26-34 and 36-51 exhibited a mean relative $pDC_{50}$ of ≥8.0.

Examples 1-51 exhibited a mean asymptote max of ≥50%.

Examples 1-2, 4-5, 7, 9-12, 14, 16-18, 20-26, 29, 35, 43 and 49 exhibited a mean asymptote max of ≥80%.

Example 6 exhibits a mean relative $pDC_{50}$ of 8.8 and a mean asymptote max of 78%.

Androgen Receptor Degradation-Imaging Assay

Degradation of Androgen Receptor (AR) protein in human prostate cancer cell lines (MDA-PCa-2b (AR T878A/L702H), LNCaP (AR T878A), VCaP (AR wild type and amplified) 22RV1 (AR H875Y) and PC3 (AR negative control)) treated with AR PROTACs was quantified using immunofluorescence. Prostate cancer cells were plated (MDA-PCa-2b, and VCaP 16,000 cells/well; LNCaP and 22RV1 32,000 cells/well, and PC3 8,000 cells/well) in an optical bottom 96-well cell culture plate and allowed to attach overnight. The prostate cancer cell lines were treated for 16 hours with a 10-point 3-fold dilution series (dose range=0.02 nM to 333 nM). PC3 is included as an AR negative control and not treated with compound. Cells are fixed and permeabilized with 4% formaldehyde, blocked with 10% goat serum in immunofluorescence (IF) buffer (130 mM NaCl, 7 mM Na2HPO4, 3.5 mM $NaH_2PO_4$, 7.7 mM $NaN_3$, 0.1% BSA, 0.2% Triton X, 0.05% Tween 20) prior to overnight incubation with rabbit antibody specific for C terminus of AR (commercially available from RevMaB Biosciences). Following washes with IF buffer, cells were incubated with fluorescent secondary antibody (Goat anti-rabbit Alexa 647; commercially available from Invitrogen) and Hoechst nuclear stain (commercially available from Themo Scientific) prior to quantification of nuclear AR levels via Opera Phenix high-content fluorescent imager using a 40× water objective. Image analysis was performed with Harmony software.

The averaged nuclear Alexa 647 median fluorescence intensity (MFI) of PC3 cells is subtracted from the nuclear Alexa 647 MFI of PROTAC treated and DMSO control treated cells. % AR remaining is calculated for PROTAC treatments as a percent of the DMSO control (MFI PROTAC treated/MFI DMSO control treated)*100). DC50 and the Dmax values, were obtained from these normalised values fitted with a 4-parameter sigmoidal response curve (Xlfit software). The DC50 is the interpolated concentration of PROTAC corresponding to 50% of the protein being degraded, and the Dmax parameter is the maximum experimentally observed degradation.

Results

Examples 6, 8, 15-17, 20, 28, 30, 32, 39, 47 and 48 were tested in the Androgen Receptor Degradation-Imaging Assay in the LNCaP cell line. Each of these examples exhibited a pDC50 of ≥8.0 and a Dmax of ≥80%.

Examples 5, 6, 8, 15-17, 20, 28, 30-32, 39, 40, 43 and 47-51 were tested in the Androgen Receptor Degradation-Imaging Assay in the 22RV-1 cell line. Each of these examples exhibited a pDC50 of ≥8.0 and a Dmax of ≥80%.

Examples 5, 6, 8, 15-17, 20, 28, 30-32, 39, 40, 43 and 47-51 were tested in the Androgen Receptor Degradation-Imaging Assay in the VCaP cell line. Each of these examples exhibited a pDC50 of ≥8.0 and a Dmax of ≥80%.

Examples 5, 6, 8, 15-17, 20, 28, 30-32, 39, 40, 43 and 47-51 were tested in the Androgen Receptor Degradation-Imaging Assay in the MDA-PCa-2b cell line. Each of these examples exhibited a pDC50 of ≥7.0 and a Dmax of ≥80%.

Figure 2:
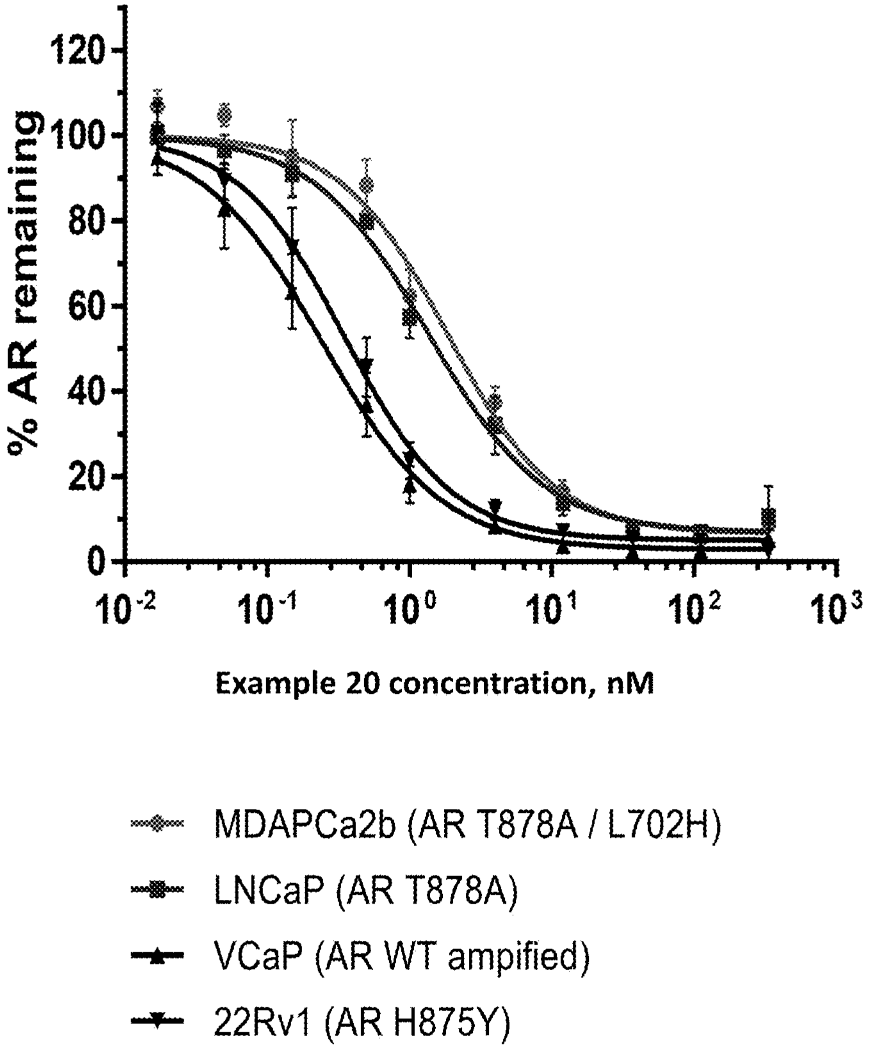
FIG. 2 is a graph showing the relationship between concentration of the compound of Example 20 versus percentage of Androgen Receptor remaining in human prostate cancer cell lines following 16 hours treatment.

FIG. 2 is a graph showing the relationship between concentration of the compound of example 20 versus percentage of Androgen Receptor remaining in human prostate cancer cell lines. Good reductions are observed in all prostate cancer cells lines showing that example 20 demonstrates broad activity across the different mutational forms of the Androgen Receptor observed in prostate cancer cell lines.

Dual Mutant (T878A/L702H) Androgen Receptor Degradation Assay Protocol

Degradation of Androgen Receptor dual T878A/L702H mutant protein in human MDA-PCa-2b (ATCC) cells treated with PROTACs was quantified using the HTRF Human Androgen Receptor Detection Kit (PerkinElmer) in 384 well assay plate format. 10 mM DMSO (Sigma-Aldrich) stock solutions of PROTACs were prepared and diluted across an 11 concentration, 3-fold increment range, and 25 nL dispensed into a white opaque bottomed 384 well assay plate (Thermofisher) using an acoustic ECHO dispenser (Labcyte). Cells were cultured in growth medium (BRFF—HPC-1 (Athena ES) supplemented with 20% FBS (Gibco), penicillin 50U/mL and streptomycin 50 µg/mL (Gibco, #15140-122)) in collagen I or poly-D-lysine coated T175 flasks (Corning, #356487 or #356539, respectively). For the assay, cells were harvested from the flask, centrifuged at 200 g for 5 min and then resuspended in the growth medium. 25 µl of cell suspension containing 10,000 cells was dispensed into each well of the assay plate containing the test compounds, which was then incubated for 18 h at 37° C./5% $CO_2$. Control wells were included on each assay plate, with assay medium without cells being the no AR remaining 100% effect control, and cells treated with DMSO vehicle only, without PROTAC, the 0% effect control. After 18 h incubation 8 µl of supplemented lysis buffer from HTRF kit was added to each well and the plate shaken at 500 rpm for 1 h at room temperature. 8 μl of antibody mix in Detection buffer from HTRF kit was added to each well and the plate was incubated for 2 h in dark at mom temperature. The fluorescence was measured at both 620 nm and 665 nm using an excitation wavelength of 337 nm with a PHER-Astar microplate reader (BMG Labtech) and the % AR protein remaining in each well was calculated by normalising the HTRF ratio (665 nm signal/620 nm signal) value to the control wells mentioned above. Parameters corresponding to the potency and efficacy estimates of the PROTACs were obtained from these normalised values using curve fitting software (IDBS ActivityBase). These included the DC50 and the Dmax estimates. Two versions of the DC50, called relative DC50 and absolute DC50, were typically generated. These are the inflection point of a fitted 4 parameter sigmoidal response curve and the interpolated concentration of PROTAC corresponding to 50% of the protein being degraded, respectively. The Dmax parameter was the maximum experimentally observed degradation and the asymptote max parameter the fitted response curve asymptote maximum.

The effects of PROTACs on cell viability were estimated by measuring cellular ATP levels using the CellTiter-Glo® Luminescent Cell Viability Assay (Promega). ATP assays were conducted in parallel with AR HTRF assays on a separate assay plate on the same day, following manufacturer's instructions and the same general procedure detailed above.

Results

Examples 1-16, 20-29 and 31-51 were tested in the dual mutant (T878A/L702H) Androgen Receptor Degradation Assay.

Examples 1-16, 20-29 and 31-51 exhibited a mean relative pDC50 of ≥6.0.

Examples 5-6, 9, 20-21, 25, 28-29, 36-37, 39, 43, 45-48 and 50 exhibited a mean relative $pDC_{50}$ of ≥7.0.

Examples 1-16, 20-29 and 31-35 and 37-44 and 46-51 exhibited a mean asymptote max of ≥50%.

Example 36 exhibits a mean asymptote max of 41% and Example 45 exhibits a mean asymptote max of 49%.

Examples 1-2, 5, 8-16, 20-25, 29, 32, 37-39, 41, 43, and 49-51 exhibited a mean asymptote max of ≥70%.

Example 6 exhibits a mean relative pDC50 of 7.07 and a mean asymptote max of 67%.

Example 20 exhibits a mean relative pDC50 of 7.20 and a mean asymptote max of 74%.

Degradation of Overexpressed Wild Type and Mutant Forms of the Androgen Receptor in A549 Cell Lines A549 cells were transduced to express wild type androgen receptor and Androgen receptor containing the following mutations (L702H, H875Y W742C W742L F877L, T878A and T878A/H875Y) with HiBiT tags. Transduced cells following puromycin selection were maintained in a humidified incubator (at 37° C. and 5% CO2 in the DMEM medium supplemented with 1% (v/v) Pen/Strep, 1% (v/v) Glutamax and 10% (v/v) FBS. A549 cells expressing each AR construct were detached from plate and counted. Cell suspensions at density 0.2 million per mL were prepared. Cell suspension was supplemented with 100 μg/mL of cycloheximide to block protein synthesis. Cells were preincubated with cycloheximide for 1 hr before seeding. Cells were seeded onto 384-well plate at density of 5,000 in 25 μL per well. A two fold serial dilution of test compounds, starting from 1 μM (row A) in 2-fold serial dilution series across the column using Tecan D300e dispenser. Technical replicates of four well were made on the plate for HiBiT assay and replicates of two well for CTG assay. The plates was incubated at 37° C., 5% $CO_2$ for 24 hours.

Nano-Glo HiBiT Lytic reagent was prepared by adding LgBiT protein and Nano-Glo® substrate to lytic buffer pre-equilibrated at room temperature following manufacturer protocol (https://www.promega.co.uk/resources/protocols/technical-manuals/101/nanoglo-luciferase-assay-system-protocol). 25 μL reagent was added to each well. The plates were then centrifuged (100×G, 1 min) and incubated on shaker for 10 mins before taking readings on Pherastar Luminescence microplate reader.

Raw data was processed in Excel with signal from each compound treatment normalised to vehicle control (0.1% DMSO treatment). Normalised response was plotted in Prism Graphpad (v 5.0.4). Curves were fitted using sigmoidal dose-response model ("log[compound] vs response") with no constraints on top and bottom of curves. XC50 was determined as mid-point of the dose response curve.

Results

The ability of compound of example 20 to degrade Androgen Receptor was assessed in cell lines overexpressing both wild type and disease relevant mutant forms. The data is summarised below. Note that, due to differences in expression levels, the pXC50 values will not be directly comparable across cell lines. The values however, demonstrate degradation of all mutant forms tested.

| AR mutant | Summary pXC50 |
|---|---|
| L702H | 9.00 |
| H875Y | 8.83 |
| W742C | 8.57 |
| W742L | 8.93 |
| F877L | 8.84 |
| T878A | 8.81 |
| T878A.H875Y | 8.57 |
| WT | 8.95 |

The invention claimed is:

1. A compound of formula (V), a tautomer of a compound of formula (V), or a salt thereof (V)

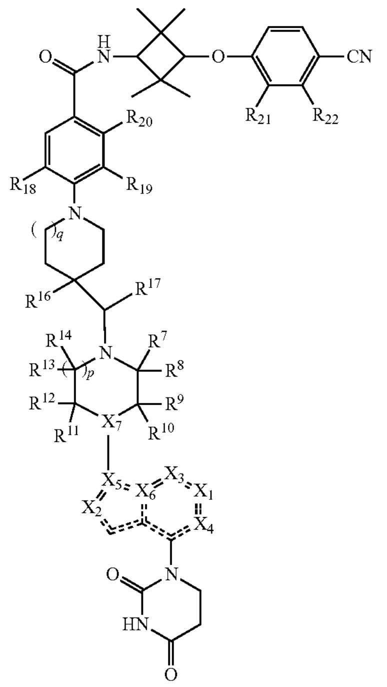

wherein:

$X_1$ is N or C—$R^1$ wherein $R^1$ is selected from the group consisting of H, halo, and $C_{1-4}$haloalkyl;

$X_4$ is C—$R^2$ or N wherein $R^2$ is selected from the group consisting of H, halo and $C_{1-3}$haloalkyl;

$X_2$ and $X_3$ are independently selected from N or CH;

$X_6$ and $X_5$ are independently selected from N or C, wherein when $X_6$ is N, $X_5$ is C;

p and q are independently 0 or 1;

$X_7$ is $CR^6$;

$R^6$, $R^7$, $R^8$, $R^9$, $R^{10}$, $R^{11}$, $R^{12}$, $R^{13}$, $R^{14}$ and $R^{17}$ are independently selected from H or halo;

$R^{16}$ is H, OH or halo;

$R^{18}$, $R^{19}$ and $R^{20}$ are independently H, halo or $C_{1-3}$haloalkyl;

$R^{22}$ is selected from the group consisting of halo and $OR^{23}$ $R^{21}$ is independently H or methyl, and $R^{23}$ is $C_{1-3}$alkyl.

2. The compound of formula (V), the tautomer of the compound of formula (V), or the salt thereof according to claim 1, wherein:

$X_5$ is N, $X_2$ and $X_3$ are each CH, $X_6$ is C, $X_1$ is C—$R^1$ and $X_4$ is C—$R^2$; or $X_5$ and $X_2$ are each N, $X_3$ is CH, $X_6$ is C, $X_1$ is C—$R^1$ and $X_4$ is C—$R^2$; or $X_5$ and $X_4$ are each N, $X_2$ and $X_3$ are each CH, $X_5$ is C and $X_1$ is C—$R^1$; or $X_5$ and $X_3$ are each N, $X_2$ is CH, $X_6$ is C, $X_1$ is C—$R^1$ and $X_4$ is C—$R^2$; or $X_5$, $X_2$ and $X_3$ are each N, $X_6$ is C, $X_1$ is C—$R^1$ and $X_4$ is C—$R^2$; or $X_5$, $X_2$ and $X_4$ are each N, $X_3$ is CH, $X_6$ is C and $X_1$ is C—$R^1$; or $X_5$, $X_3$ and $X_4$ are each N, $X_2$ is CH, $X_5$ is C and $X_1$ is C—$R^1$.

3. The compound of formula (V), the tautomer of the compound of formula (V), or the salt thereof according to claim 2, wherein $R^1$ is H, halogen or —$CF_3$.

4. The compound of formula (V), the tautomer of the compound of formula (V), or the salt thereof according to claim 2, wherein $R^2$ is H or fluoro.

5. The compound of formula (V), the tautomer of the compound of formula (V), or the salt thereof according to claim 2, wherein $R^{10}$ is H or halo and $R^7$, $R^8$, $R^9$, $R^{11}$, $R^{12}$, $R^{13}$ and $R^{14}$ are each H.

6. The compound of formula (V), the tautomer of the compound of formula (V), or the salt thereof according to claim 2, wherein $R^{18}$, $R^{19}$ and $R^{20}$ are each independently H or halo.

7. The compound of formula (V), the tautomer of the compound of formula (V), or the salt thereof according to claim 6, wherein:

$R^{18}$ is fluoro, and $R^{19}$ and $R^{20}$ are each H; or $R^{18}$ is chloro, and $R^{19}$ and $R^{20}$ are each H; or $R^{18}$ and $R^{20}$ are each fluoro, and $R^{19}$ is H; or $R^{18}$ and $R^{19}$ are each fluoro, and $R^{20}$ is H.

8. The compound of formula (V), the tautomer of the compound of formula (V), or the salt thereof according to claim 2, wherein:

$R^{22}$ is selected from the group consisting of halo and —$OR^{23}$;

$R^{21}$ is independently H or methyl; and $R^{23}$ is $C_{1-3}$alkyl.

9. The compound of formula (V), the tautomer of the compound of formula (V), or the salt thereof according to claim 8, wherein $R^{22}$ is selected from the group consisting of chloro, methoxy and ethoxy.

10. The compound of formula (V), the tautomer of the compound of formula (V), or the salt thereof according to claim 8, wherein $R^{21}$ is H.

11. The compound of formula (V), the tautomer of the compound of formula (V), or the salt thereof according to claim 2, wherein $R^{16}$ is H.

12. The compound of formula (V), the tautomer of the compound of formula (V), or the salt thereof according to claim 2, wherein $R^{17}$ is H.

13. The compound of formula (V), the tautomer of the compound of formula (V), or the salt thereof according to claim 2, wherein q is 1.

14. The compound of formula (V), the tautomer of the compound of formula (V), or the salt thereof according to claim 2, wherein q is 0.

15. A compound that is N-((1r,3r)-3-(4-cyano-3-methoxy-phenoxy)-2,2,4,4-tetramethylcyclobutyl)-4-(4-((4-(4-(2,4-dioxotetrahydropyrimidin-1(2H)-yl)-1H-pyrazolo[4,3-c]pyridin-1-yl)piperidin-1-yl)methyl)piperidin-1-yl)-3-fluorobenzamide or a tautomer, or a pharmaceutically acceptable salt thereof.

16. A pharmaceutically acceptable salt, comprising the compound, the tautomer, or the pharmaceutically acceptable salt thereof according to claim 15 in salt form, wherein the pharmaceutically acceptable salt is a benzenesulfonate (besylate), ethanesulfonate (esylate), hydrochloride, methanesulfonate (mesylate), naphthalene-1,5-disulfonate (napadisylate), or p-toluenesulfonate (tosylate) salt.

17. A compound or tautomer, comprising the compound, the tautomer, or the pharmaceutically acceptable salt thereof according to claim 15 in free base or tautomer form.

18. The compound, the tautomer, or the pharmaceutically acceptable salt thereof according to claim 15, in a free base crystalline form having an X-ray powder diffraction pattern using CuKα radiation comprising characteristic peaks at 2°theta values of 6.4°±0.2°, 16.7°±0.2° and 17.4°±0.2°.

19. A pharmaceutical composition comprising the compound, tautomer or salt thereof according to claim 1 and a pharmaceutically acceptable excipient.

20. A pharmaceutical composition comprising the compound, tautomer or pharmaceutically acceptable salt thereof according to claim 15 and a pharmaceutically acceptable excipient.

21. A pharmaceutical composition comprising the pharmaceutically acceptable salt according to claim 16 and a pharmaceutically acceptable excipient.

22. A pharmaceutical composition comprising the compound or tautomer according to claim 17 and a pharmaceutically acceptable excipient.

23. A method of treating prostate cancer, comprising administering to a subject in need thereof a therapeutically effective amount of the compound, tautomer or salt thereof as defined in claim 15.

24. The method according to claim 23, wherein the prostate cancer is metastatic castration resistant prostate cancer.

25. A method of treating prostate cancer, comprising administering to a subject in need thereof a therapeutically effective amount of the pharmaceutically acceptable salt as defined in claim 16.

26. The method according to claim 25, wherein the prostate cancer is metastatic castration resistant prostate cancer.

27. A method of treating prostate cancer, comprising administering to a subject in need thereof a therapeutically effective amount of the compound or tautomer as defined in claim 17.

28. The method according to claim 27, wherein the prostate cancer is metastatic castration resistant prostate cancer.

* * * * *